United States Patent [19]

Lewis et al.

[11] Patent Number: 5,840,918
[45] Date of Patent: Nov. 24, 1998

[54] ISOPRENYL TRANSFERASE INHIBITORS

[75] Inventors: Michael D. Lewis; James J. Kowalczyk, both of Andover; Amy E. Christuk, Newbury; Rulin Fan, Andover; Edmund M. Harrington, Medford; Xiaoning C. Sheng, Andover; Hu Yang, North Andover; Ana Maria Garcia, Belmont, all of Mass.; Ieharu Hishinuma, Moriya-Machi, Japan; Takeshi Nagasu, Nagakuni-Machi, Japan; Kentaro Yoshimatsu, Tsuchiura, Japan

[73] Assignee: Eisai Co., Ltd., Tokyo, Japan

[21] Appl. No.: 704,664

[22] PCT Filed: Mar. 15, 1995

[86] PCT No.: PCT/US95/03387

§ 371 Date: Mar. 19, 1997

§ 102(e) Date: Mar. 19, 1997

[87] PCT Pub. No.: WO95/25086

PCT Pub. Date: Sep. 21, 1995

Related U.S. Application Data

[63] Continuation-in-part of Ser. No. 214,793, Mar. 15, 1994, abandoned, which is a continuation of Ser. No. 277,201, Jul. 19, 1994, abandoned.

[51] Int. Cl.$^6$ .................... C07D 333/22; C07D 307/02; C07C 321/00; C07C 233/00
[52] U.S. Cl. .................... 549/77; 549/321; 549/496; 560/9; 562/426; 546/329; 544/162; 564/204; 564/197; 564/198; 564/162; 564/163; 564/193; 564/199
[58] Field of Search .................... 564/204, 197, 564/198, 162, 163, 193, 199; 549/77, 496, 321; 560/9; 562/426; 546/329; 544/162; 514/438, 471, 473, 534, 359, 277.5

[56] References Cited

U.S. PATENT DOCUMENTS

| | | | |
|---|---|---|---|
| 5,134,123 | 7/1992 | Branca et al. | 514/18 |
| 5,141,851 | 8/1992 | Brown et al. | 435/15 |
| 5,238,922 | 8/1993 | Graham et al. | 514/18 |
| 5,245,061 | 9/1993 | Singh | 554/121 |
| 5,250,564 | 10/1993 | Hirschmann et al. | 514/414 |
| 5,260,465 | 11/1993 | Singh et al. | 554/134 |
| 5,260,479 | 11/1993 | Singh | 560/190 |
| 5,283,256 | 2/1994 | Dufresne et al. | 514/452 |
| 5,286,895 | 2/1994 | Harris et al. | 560/60 |
| 5,288,707 | 2/1994 | Metternich | 514/19 |
| 5,326,773 | 7/1994 | de Solms et al. | 514/336 |
| 5,340,828 | 8/1994 | Graham et al. | 514/357 |
| 5,350,867 | 9/1994 | Singh | 554/121 |
| 5,352,705 | 10/1994 | Deana et al. | 514/630 |
| 5,362,906 | 11/1994 | Anthony et al. | 562/23 |

FOREIGN PATENT DOCUMENTS

| | | |
|---|---|---|
| 0 534 546 A1 | 3/1990 | European Pat. Off. . |
| 0 523 873 A1 | 1/1993 | European Pat. Off. . |
| 0 528 486 A2 | 2/1993 | European Pat. Off. . |
| 0 535 730 A2 | 4/1993 | European Pat. Off. . |
| 0 537 007 A1 | 4/1993 | European Pat. Off. . |
| 0 540 782 A1 | 5/1993 | European Pat. Off. . |
| 0 547 671 A2 | 6/1993 | European Pat. Off. . |
| 227 0312 | 3/1994 | United Kingdom . |
| WO 93/16980 | 9/1993 | WIPO . |
| WO 9400419 | 1/1994 | WIPO . |
| WO 9403597 | 2/1994 | WIPO . |
| WO 9404561 | 3/1994 | WIPO . |
| WO 9407485 | 4/1994 | WIPO . |
| WO 9408575 | 4/1994 | WIPO . |
| WO 9409766 | 4/1994 | WIPO . |
| WO 94/10137 | 11/1994 | WIPO . |

OTHER PUBLICATIONS

Reiss et al., "Inhibition of Purified p21ras Farnesyl:Protein Transferase by Cys–AAX Tetrapeptides", Cell 62:81–88 (1990).

Reiss et al., "Sequence Requirement for Peptide Recognition by Rat Brain p21ras Protein Farnesyltransferase", Proc. Natl. Acad. Sci. USA 88:732–736 (1991).

James et al., "Benzodiazepine Peptidomimetics: Potent Inhibitors of Ras Farnesylation in Animal Cells", Science 260:1937–1942 (1993).

Kohl et al., "Selective Inhibition of ras–Dependent Transformatoin by a Farnesyltransferase Inhibitor", Science 260:1934–1937 (1993).

Garcia et al., "Peptidomimetic Inhibitors of Ras Farnesylation and Function in Whole Cells", J. Biol. Chem. 268:18415–18418 (1993).

Bhide R.S. et al., "Rational Design of Potent Carboxylic Acid Based Bisubstrate Inhibitors of Ras Farnesyl Protein Transferase", Bioorg. Med. Chem. Lett. 4:2107–2112 (1994).

Cox A.D. et al., "The CAAX Peptidomimetic Compound B581 Specifically Blocks Farnesylated, But Not Geranylgeranylated or Myristylated, Oncogenic Ras Signaling and Transformation", J. Biol. Chem. 269:19203–6 (1994).

Nigam M. et al., "Potent Inhibition of Human Tumor P21ras Farnesyltransferase by $A_1A_2$–Lacking P21ras $CA_1A_2X$ Peptidomimetics", J. Biol. Chem. 268:20695–8 (1993).

Patel D.V. et al., "Phenol Based Tripeptide Inhibitors of Ras Farnesyl Protein Transferase", Bioorg. Med. Chem. Lett. 4:1883–1888 (1994).

Qian Y. et al., "Design and Structural Requirements of Potent Peptidomimetic Inhibitors of P21ras Farnesyltransferase", J. Biol. Chem. 269:12410–13 (1994).

Singh S.B. et al., "Fusidienol: A Novel Inhibitor of Ras Farnesyl–Protein Transferase from Fusidium Griseum", Tetrahedron Lett. 35:4693–6 (1994).

Sebti S.M. et al., "Lovastatin, A Chloresterol Biosynthesis Inhibitor, Inhibits the Growth of Human H–Ras Oncogene Transformed Cells in Nude Mice", Cancer Comm. 3:141–147 (1991).

Primary Examiner—Deborah C. Lambkin
Attorney, Agent, or Firm—Clark & Elbing LLP

[57] ABSTRACT

Peptidomimetic compounds useful in the treatment of Ras-associated human cancers, and other conditions mediated by farnesylated or geranylgeranylated proteins; and synthetic intermediates thereof.

19 Claims, No Drawings

ISOPRENYL TRANSFERASE INHIBITORS

This application is a 371 of U.S. Pat. No. 5/03387 filed Mar. 15, 1995 which is a CIP of 08/214,793 filed Mar. 15, 1994, abandoned, which is a continuation of 08/277,201 filed Jul. 19, 1994, abandoned.

BACKGROUND OF THE INVENTION

This invention concerns peptidomimetics useful in the treatment of human cancers.

Ras is an oncogene prevalent in over 20% of all human cancers. In particular, ras oncogenes are found in approximately 30% of all lung cancer, 30% of all myeloid leukemia, 50% of all colorectal carcinoma, and 90% of all pancreatic carcinoma. Barbacid, M., *Ann. Rev. Biochem.,* 56:779 (1987), Bos, J. L., *Cancer Res.* 49:4682 (1989). Examples of ras mutations include H-ras, K-ras, and N-ras.

Like other members of the superfamily of small GTP-hydrolyzing proteins, ras-encoded proteins require post-translational processing for membrane association and biological function. Maltese, W. A., *FASEB Journal,* 4:3319 (1990), Hancock, J. F. et al., *Cell,* 57:1167 (1989).

The post-translational processing of the ras protein is signalled by a short carboxy terminus consensus sequence, a CAAX box, indicating which isoprenyl group (farnesyl or geranylgeranyl) is to be attached. For farnesylated proteins, such as Ras, lamin B, and γ-transducin, C is cysteine, A is an aliphatic amino acid, and X is methionine, serine, or glutamine. Geranylgeranylated proteins such as Rap, Rab, Rho and other small GTP-binding proteins, have similar CAAX sequences in which X is usually leucine, or occasionally phenylalanine.

Post-translational processing of the ras-encoded protein includes at least three steps. First, reaction with farnesyl pyrophosphate attaches a farnesyl group to the $Cys^{186}$ residue. Second, a specific protease cleaves the three carboxy-terminal amino acids. Third, the carboxylic acid terminus is methylated to a methyl ester. The farnesyl transferase enzyme (FTase) mediates the attachment of the farnesyl group to a protein. The geranylgeranyl transferase I enzyme (GGTase) mediates the attachment of the geranylgeranyl group to a protein.

Post-translational processing, particularly farnesylation, of ras proteins is critical for in vivo ras protein function. Upstream of FTase, farnesylation of a ras protein can be inhibited by mevalonate synthesis inhibitors such as lovastatin or compactin, which are HMG-CoA reductase inhibitors. Direct inhibition of FTase by short peptides or peptide-like substrates has also been demonstrated.

SUMMARY OF THE INVENTION

This invention features peptidomimetics useful in the treatment of ras-associated human cancers. The compounds of the invention inhibit post-translational modification of ras proteins by FTase, thereby down-regulating ras protein function. Substitution at the $R^7$, $R^2$, $R^4$ or $R^5$ positions (see, e.g., formula I below) modulates the specificity and selectivity of a compound of the invention for FTase and GGTase. The compounds of the invention inhibit post-translational modification of ras proteins by the related GGTase, which also results in down-regulation of ras protein function. Certain compounds of the invention are selective or specific for FTase, in preference over GGTase.

In general, the invention features a compound of the formula:

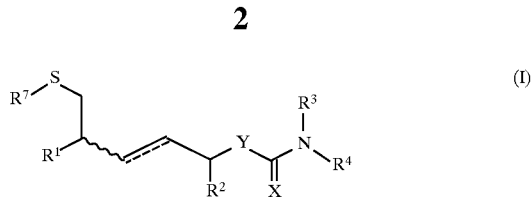

wherein $R^1$ is H, $NHR^8$, or $NR^8R^9$, wherein $R^8$ is H, $C_{1-6}$ alkyl, $C_{1-6}$ acyl, $C_{2-14}$ alkyloxycarbonyl or any other amino-protecting group, and $R^9$ is $C_{1-6}$ alkyl, $C_{1-6}$ acyl, or $C_{2-14}$ alkyloxycarbonyl; or, when taken together with $R^7$, a bifunctional organic moiety of fewer than 50 carbon atoms; $R^2$ is H, $C_{1-8}$ alkyl, ($C_{6-40}$ aryl) ($C_{0-6}$ alkyl), or ($C_{3-10}$ heteroaryl) ($C_{0-6}$ alkyl); $R^3$ is H, $C_{1-6}$ alkyl, or ($C_{6-40}$ aryl) ($C_{0-6}$ alkyl); $R^4$ is $C_{3-16}$ cycloalkyl, ($C_{3-16}$ heterocyclic radical)($C_{0-6}$ alkyl), ($C_{6-12}$ aryl)-($C_{0-6}$ alkyl), ($C_{3-16}$ heteroaryl) ($C_{0-6}$ alkyl), $C_{2-14}$ alkoxycarbonyl (or, where X is 2 singly-bonded H, any other amino-protecting group), $R^5(CH-)(C=O)R^6$ $R^5(CH-)(C=S)R^6$, $R^5(CH-)(CH_2)R^6$, or $R^5(CH_2-)$, wherein $R^5$ is $C_{1-6}$ alkyl, ($C_{3-10}$ heterocyclic radical) ($C_{0-6}$ alkyl),($C_{3-10}$ heteroaryl)($C_{1-6}$ alkyl), hydroxymethyl, $-(CH_2)_n-A$ $-(CH_2)_m-CH_3$, $-(CH_2)_n(C=O)NH_2$, or $-(CH_2)_n(C=O)NH(CH_2)_mCH_3$ (wherein A is O, S, SO, or $SO_2$, n is 0, 1, 2 or 3, and m is 0, 1, or 2), or any other side chain of a naturally occurring amino acid; and $R^6$ is H, $NH_2$, NHOH, $C_{3-16}$ heterocyclic radical, $C_{3-16}$ heteroaryl, $NR^{10}R^{11}$, $OR^{12}$, $NR^{10}OR^{11}$, $NHOR^{13}$, or any other carboxyl-protecting group (e.g., where $R^4$ is $R^5(CH-)$ $(C=O)R^6$, and $R^6$ is, e.g., $OR^{12}$) or any other hydroxyl protecting group (e.g., where $R^4$ is $R^5(CH-)(CH_2)OR^{12}$); wherein each of $R^{10}$ and $R^{11}$, independently, is H, $C_{1-6}$ alkyl, ($C_{3-16}$ heterocyclic radical) ($C_{0-6}$ alkyl), or ($C_{3-16}$ heteroaryl) ($C_{0-6}$ alkyl), $R^{12}$ is H, $C_{1-6}$ alkyl, ($C_{1-12}$ acyl) $oxy(C_{1-12}$ alkyl), ($C_{1-12}$ alkyl)oxy($C_{1-12}$ alkyl), $C_{2-14}$ alkyloxycarbonyl, or where $R^4$ is $R^5(CH-)$ $(CH_2)R^6$, any other amino-protecting group, and $R^{13}$ is H, $C_{1-6}$ alkyl, or ($C_{6-40}$ aryl) ($C_{0-6}$ alkyl); X is =O, =S, or two singly-bonded H; Y is selected from the following five formulae:

wherein $R^{14}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

wherein $R^{15}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

wherein $R^{16}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

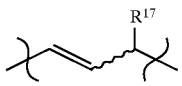

(iv)

wherein $R^{17}$ is H, $C_{1-8}$ alkyl, ($C_{6-40}$ aryl) ($C_{0-6}$ alkyl), ($C_{3-10}$ heteroaryl) ($C_{0-6}$ alkyl), or ($C_{3-10}$ heterocyclic radical) ($C_{0-6}$ alkyl); and

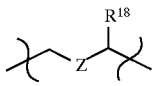

(v)

wherein $R^{18}$ is H, $C_{1-8}$ alkyl, ($C_{6-40}$ aryl) ($C_{0-6}$ alkyl), ($C_{3-10}$ heterocyclic radical) ($C_{0-6}$ alkyl), or ($C_{3-10}$ heteroaryl)($C_{0-6}$ alkyl), and Z is O, S, SO, $SO_2$, or $NR^{19}$ wherein $R^{19}$ is H, $C_{1-6}$ alkyl, $C_{1-6}$ acyl, ($C_{6-40}$ aryl)-($C_{0-6}$ alkyl), $C_{3-10}$ heterocyclic radical, ($C_{3-10}$ heteroaryl)-($C_{0-6}$ alkyl), or $C_{2-14}$ alkyloxycarbonyl; or wherein $R^{18}$ and $NR^{19}$ taken together form a bifunctional $C_{6-40}$ aryl, a bifunctional $C_{3-12}$ heterocyclic radical, or a bifunctional $C_{3-12}$ heteroaryl; and $R^7$ is an organic moiety having fewer than 50 carbon atoms or, when taken together with $R^1$, a bifunctional organic moiety having fewer than 50 carbon atoms; or a pharmaceutically acceptable salt thereof.

Compounds of the invention include, for example, compounds PD301, PD311, PD321, PD331, PD341, PD351, PD361, PD371, PD381, PD391, PD401, PD411, PD421, PD431, PD441, PD451, PD461, PD012, PD022, PD032, PD042, PD052, PD062, PD072, PD082, PD092, PD102, PD112, PD132, PD142, PD152, PD162, PD172, PD182, PD192, PD202, PD212, PD222, PA011, PA021, PA031, PA041, PA051, PA061, PA071, PA081, PA091, PA101, PA111, PA121, PA131, PA141, PE011, PE021, PE031, PE041, PE051, PE061, PT011, PM011, PM021, PM031, PM041, PM051, PM061, PM071, PM081, PM091, PM101, PM111, PM121, PM131, PM141, PM151, PM161, PM012, PM022, PM032, PM042, PM052, PM062, PM072, PM082, PM092, PM102, PM112, PM122, PM132, PM142, PM152, PM162, PM172, PM182, PM192, PM202, PM212, and PM222.

In one aspect of the invention, compounds of the invention inhibit post-translational modification of the oncogenic ras protein by FTase, GGTase, or both. Such inhibition reduces or blocks the ability of the ras protein to transform normal cells to cancer cells. Compounds of formulae I–VI and VIII–XI, therefore, are for use in medicine (e.g., treatment of conditions mediated by farnesylated or geranylgeranylated proteins, such as treatment of ras-associated tumors, in mammals, e.g., humans).

Examples of ras-associated tumors include: tumors of the bladder, breast, colon, kidney, liver, lung, ovary, pancreas, and stomach; hematopoietic tumors of lymphoid (acute lymphocytic leukemia, B-cell lymphoma, Burkitt's lymphoma) and myeloid (acute and chronic myelogenous leukemias, promyelocytic leukemia) origins; in tumors of mesenchymal origin (such as fibrosarcomas and rhabdomyosarcomas); and melanomas, teratocarcinomas, neuroblastomas, gliomas, and keratoacanthomas (see supra, Barbacid, 1987).

In another aspect, the invention encompasses methods of treating ras-associated tumors in a patient by administering an effective amount of a pharmaceutical formulation of one or more compounds of the invention to the patient.

In another aspect, the invention encompasses synthetic intermediates of the disclosed inhibitor compounds such as compounds R007D, R011D, R019D, R020D, R029D, R003E, R005E, R004T, R003M–R006M, R025M, R027M, R023D, R017M, R006A, R004A, R003A, R012A, R014D, R023M, R024D, R007E, R001A, R007T, R013D, R018M, and Wittig reagent R012M.

Other features and advantages of the present invention will be apparent from the following drawings and detailed description, and also from the appending claims.

DETAILED DESCRIPTION

A. Abbreviations

Abbreviations used herein unless otherwise specified are: BOC or t-BOC (t-butoxycarbonyl); $BOC_2O$ or $tBOC_2O$ (di-t-butyldicarbonate); CMC (1-cyclohexyl-3-(2-morpholinoethyl)carbodiimide metho-p-toluenesulfonate); COD (1,5-cyclooctadiene); DCC (dicyclohexylcarbodiimide); DIBAL (diisobutylaluminum hydride); DMAP (4-dimethylaminopyridine); DME (1,2-dimethoxyethane); DMF (dimethylformamide); EDC (1-(3-dimethylaminopropyl)-3-ethylcarbodiimide); FC (flash chromatography on silica gel); HMDS (hexamethyldisilazide, also known as bis(trimethylsilyl) amide); HOBT (hydroxybenzotriazole hydrate); HPLC (high pressure liquid chromatography); MTT ([3-(4,5-dimethylthiazol-2-yl)-2,5-diphenyl-2H-tetrazolium bromide]); NMM (N-methylmorpholine); PNB (p-nitrobenzyl); RP (reversed phase); TBAF (tetrabutylammonium fluoride); TBS (t-butyldimethylsilyl); TFA (trifluoroacetic acid); Tf (trifluoromethanesulfonyl); $Tf_2O$ (trifluoromethanesulfonic anhydride); THF (tetrahydrofuran); TsCl (p-toluenesulfonyl chloride); and TsOH (p-toluenesulfonic acid monohydrate).

B. Terms

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, sec-hexyl, isohexyl, and tert-hexyl. Substituted alkyl groups may have one, two, three, or more substituents, which may be the same or different, each replacing a hydrogen atom. Substituents are halide, hydroxyl, protected hydroxyl, amino, protected amino, carboxy, protected carboxyl, cyano, methylsulfonylamino, alkoxy, acyloxy, nitro, and lower haloalkyl.

Similarly, cycloalkyl, aryl, arylalkyl, alkylaryl, heteroaryl, and heterocyclic radical groups may be substituted with one or more of the above substituting groups. Examples of cycloalkyl groups are cyclopropyl, cyclopentyl, cyclohexyl, and cycloactyl. An aryl group is a $C_{6-40}$ aromatic ring, wherein the ring is made of carbon atoms (e.g., $C_{6-20}$, or $C_{6-12}$ aryl groups).

A heterocyclic radical contains at least one ring structure which contains carbon atoms and at least one heteroatom such as N, O, or S. A heteroaryl is an aromatic heterocyclic radical. Examples of heterocyclic radicals and heteroaryl groups include: thiazolyl, 2-thienyl, 3-thienyl, 3-furyl, furazanyl, 2H-pyran-3-yl, 1-isobenzofuranyl, 2H-chromen-3-yl, 2H-pyrrolyl, N-pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, phthalazinyl, cinnolinyl, and pteridinyl.

A heterocyclic radical may be attached to another moiety via a carbon atom or a heteroatom of the heterocyclic radical. In formulae I—III where $R^6$ is a heterocyclic radical or heteroaryl, $R^6$ is preferably attached to a thionyl or carbonyl of $R^4$ via a heteroatom of $R^6$. This preference extends analogously to generic formulae IV–VI where $R^{26}$ is a heterocyclic radical or heteroaryl, $R^{26}$ is preferably attached to a thionyl or carbonyl of $R^{24}$ via a heteroatom of $R^{26}$. This preference also extends analogously to formulae VIII–XI.

In certain embodiments, $R^4$ (and analogous groups such as $R^{24}$) may be a lactone or lactam (or the thiocarbonyl or thioester equivalents). For example, $R^4$ includes radicals of homoserine lactone and homocysteine lactone.

An acyl group has the formula R(C=O)— and an acyloxy group has the formula R(C=O)—O—, wherein R is H, $C_{1-12}$ alkyl, $C_{6-20}$ aryl, or $C_{7-20}$ arylalkyl. Thus, a $C_{1-14}$ acyl includes R being, for example, H, $C_{1-6}$ alkyl, $C_{6-12}$ alkyl, and $C_{7-13}$ arylalkyl. An alkyloxyalkyl group has the formula R—O—R'—, wherein each of R and R', independently, is $C_{1-12}$ alkyl (e.g., R is $C_{1-8}$ or $C_{1-6}$). An acyloxyalkyl group has the formula R—(C=O)—O—R'—, wherein each of R and R', independently, is $C_{1-12}$ alkyl, $C_{6-20}$ aryl, or $C_{7-20}$ arylalkyl (e.g., is $C_{1-8}$ or $C_{1-6}$). An alkyloxycarbonyl group has the formula R—O—(C=O)—, wherein R is $C_{2-14}$ alkyl (eg., $C_{2-6}$). A preferred alkyloxycarbonyl group is t-butoxycarbonyl (BOC). A carbamoyl group has the formula RR'N—(C=O)—, wherein each of R and R', independently, is H, $C_{1-12}$ alkyl, or $C_{6-20}$ aryl.

An activated leaving group (L, $L^n$) departs from a substrate with the pair of electrons of the covalent bond between the leaving group and the substrate; preferred leaving groups stabilize those electrons via the presence of electron-withdrawing groups, aromaticity, resonance structures, or a combination thereof. Examples of activated (or electron-withdrawing) leaving groups include halide (iodide and bromide are preferred); hydroxy; $C_{1-12}$ alkylsulfonyloxy such as mesylate and trifluoromethanesulfonate; $C_{6-20}$ arylsulfonyloxy such as p-toluenesulfonate, p-nitrobenzenesulfonate; benzoate and benzoate derivatives such as p-nitrobenzoate; $C_{7-40}$ arylalkyl such as p-nitrobenzyl; $C_{7-20}$ arylalkyloxy; $C_{1-12}$ alkoxy; $C_{2-12}$ alkyloxycarbonyl such as BOC; $C_{1-12}$ acyloxy, $C_{1-12}$ carbamoyl, and $C_{2-5}$ haloalkylcarbonyloxy such as trifluoroacetate. Examples of electron-withdrawing groups include halides, halogenated alkyls, carboxylate, and nitro groups.

Numerous thiol-, amino- and carboxyl-protecting groups are well-known to those in the art. In general, the species of protecting group is not critical provided that it is stable to the conditions of any subsequent reaction(s) on other positions of the compound and can be removed at the appropriate point without adversely affecting the remainder of the molecule. In some embodiments, $R^1$ and $R^7$ taken together are preferably a bifunctional thiol-protecting group, having two points of attachment instead of one, such as —(C=O)—and isopropylidene (—C(CH$_3$)$_2$—) which form particularly stable products.

Similarly, in some embodiments, $R^{18}$ and $NR^{19}$ taken together are a bifunctional aryl, heteroaryl, or heterocyclic radical. Examples of preferred thiol-protecting groups include thioethers, sulfenyl derivatives, disulfides, and bifunctional protecting groups such as dithiols, aminothiols, thioaminals, and thioacetals, such as thiazolidines and thiazolidinones. A preferred thiol-protecting group, such as a disulfide, will be cleaved under mild reductive conditions.

Examples of disulfides include S-ethyl, S-t-butyl, and substituted S-phenyl. In addition, symmetrical and asymmetrical disulfides are discussed further below.

Examples of thioethers include (i) S-benzyl and derivatives thereof such as S-4-methyl- and 5-3,4-dimethylbenzyl, S-p-methoxybenzyl, S-o- or p-hydroxybenzyl (or acetoxybenzyl), S-p-nitrobenzyl, S-4-picolyl, S-2-picolyl N-oxide, and S-9-anthrylmethyl; (ii) S-diphenylmethyl, substituted S-diphenylmethyl, and S-triphenylmethyl (S-trityl) thioethers such as S-diphenyl-4-pyridylmethyl, S-5-dibenzosuberyl, and S-bis(4-methoxyphenyl)methyl, and (iii) substituted S-methyl derivatives such as S-methoxymethyl, S-isobutoxymethyl, S-2-tetrahydropyranyl, S-benzylthiomethyl, thiazolidines, S-acetamidomethyl, S-benzamidomethyl, S-acetyl-, S-carboxy-, and S-cyanomethyl; and (iv) substituted S-ethyl derivatives such as S-2-nitro-1-phenylethyl, S-t-butyl, S-2,2-bis (carboethoxy)ethyl, and S-1-m-nitrophenyl-2-benzoylethyl.

Thioesters including S-acetyl, S-benzoyl, thiocarbonates (e.g., S-benzyloxycarbonyl, S-t-butoxy-carbonyl), and thiocarbamates (e.g., S-(N-ethyl)) and S-(N-methoxymethyl) are less preferred for use in the synthetic pathway shown. For example, some of these thioesters and thiocarbamates may not be resistant to the LiOH/MeOH/H$_2$O hydrolysis in Scheme VIII. However, an organic chemist of ordinary skill can make suitable modifications to the synthetic pathway, such as using an ester other than methyl, to improve the compatibility of these thiol-protecting groups.

In addition, a protecting group may be substituted for another after substantive synthetic transformations are complete. Clearly, where a compound differs from a compound disclosed herein only in that one or more protecting groups of the disclosed compound has been substituted with a different protecting group (e.g., carbamate), that compound is within the invention. Further examples and conditions for thiol-, amino-, and carboxyl-protecting group chemistry are found in T. W. Greene, *Protective Groups in Organic Synthesis,* (1st ed., 1981, 2nd ed., 1991).

The invention also encompasses isotopically-labelled counterparts of compounds disclosed herein. An isotopically-labelled compound of the invention has one or more atoms replaced with an isotope having a detectable particle-emitting (radioactive) nucleus or a magnetogyric nucleus. Examples of such nuclei include but are not limited to $^2$H, $^3$H, $^{13}$C, $^{14}$N, $^{19}$F, $^{29}$Si, $^{31}$P, and $^{32}$P. Isotopically-labelled compounds of the invention are particularly useful as probes or research tools for spectrometric analyses, radioimmunoassays, binding assays based on γ- or β-scintillation, autoradiography, and kinetic studies such as the determination of primary and secondary isotope effects.

C. Embodiments

It will be apparent to those in the art that formulae I and IV are closely related, having substituents which are analogous. For example, $R^1$, $R^5$ and $R^7$ in formula I are analogous to $R^{21}$, $R^{25}$, and $R^{27}$ in formula IV, respectively. Thus, in this description, general guidance and preferred embodiments described for $R^1$ are understood to apply to $R^{21}$, those for $R^7$ are understood to apply to $R^{27}$, and so on. In addition, those in the art will recognize other relationships, such as that formula I is closely related to formulae II and III; that formulae (i)–(v) are closely related to formulae (vi)–(x); and that formulae VII–XI are related to formulae I and IV.

In one aspect, the invention is a compound having a formula selected from formulae I–III (or IV–VI), where $R^7$ (or an analogous group such as $R^{27}$ in formula IV) is any moiety compatible with the intended use of the compound. In one aspect, a compatible moiety is an organic moiety having fewer than 100 carbon atoms, such as fewer than 50, 35, 30 or 20 carbon atoms. In another aspect, a compatible moiety is a polymer backbone or matrix for drug release or delivery, which may contain 100, 150, or more carbon atoms, due to its polymeric nature.

A compatible organic moiety must not interfere with the intended use of the compound. For example, where the use is inhibition of one or more isoprenyl transferase enzymes, the remainder moiety may enhance the inhibition; perform a supplementary ras-associated function; perform a complementary different function; or perform no particular function, including undergoing chemical cleavage from the inhibitor moiety of the compound in the body.

Examples of an organic moiety include mono- or bifunctional thiol-protecting groups; detectable or bioimaging agents; systemic or specific anti-cancer agents; targeting agents intended to localize delivery of a compound of the invention to a selected class of cells, a tissue, or an organ; directing agents intended to selectively discourage uptake of a compound of the invention by a selected class of cells, a tissue, or an organ; other competitive, noncompetitive, uncompetitive or mixed inhibition inhibitors of an isoprenyl transferase enzyme. Such inhibitors include inhibitors of ras-associated enzymes, including suicide substrates of ras-associated enzymes.

In one aspect, the compound of the invention is a disulfide. An asymmetrical disulfide is a moiety set forth in a formula selected from the formulae I–III wherein $R^7$ (or an analogous group such as $R^{27}$ in formulae IV–VI) is deleted, the free sulfur atom being bonded to any moiety having a second reactive sulfur atom to form a disulfide. Preferably, "any moiety" is an organic moiety having fewer than 100 carbon atoms, such fewer than 50, 40, 30 or 20 carbon atoms. Examples of such organic moieties include but are not limited to the other moieties listed in a previous paragraph (such as detectable or bioimaging agents, anti- cancer agents, and drug-targeting agents) and the moieties defined by $R^7$, or $R^7$ and $R^1$ when taken together.

Another embodiment of this aspect relates to an asymmetrical disulfide, wherein the organic moiety is itself a (different) moiety set forth in a formula selected from the formulae I–VI wherein $R^7$ (or an analogous group such as $R^{27}$ in formula IV) is deleted. In another embodiment, the invention relates to a symmetrical disulfide dimer, wherein $R^7$ is a moiety of the same formula with $R^7$ deleted, such as PD212, PE041, PE051, PM141, and PM022. Due to the reactivity of an unprotected thiol group, it may be desirable to store or handle a compound of the invention in the form of a symmetrical disulfide dimer or an asymmetrical disulfide.

Chemically-linked (e.g., disulfide) or formulated (mixture) combinations of two different compounds of the invention are useful not only to prevent premature sequestration in the patient, but also to formulate and deliver a dual-acting drug. For example, a first compound may be a more potent FTase inhibitor than a second compound and the second may be a more potent GGTase inhibitor than the first. Thus, to the extent that some farnesylated proteins may be alternatively geranylgeranylated, a GGTase inhibitor will also be available in the patient via the same drug dose.

Certain compounds (in fact a majority) of the invention are dual-acting compounds, wherein the compound has some degree of activity for both GGTase and FTase. The relative selectivity and specificity can be modulated by substitution (e.g., at the $R^7$, $R^2$, $R^4$, $R^5$, and Y positions). Therefore, to the extent that some farnesylated proteins may be alternatively geranylgeranylated, a GGTase inhibitor will also be available in the patient via the same compound.

In general, the preferred stereochemistry for the —$CH_2$—S—$R^7$ moiety and for each of $R^2$ and $R^5$, independently, (and analogous groups such as $R^{22}$, $R^{52}$, and $R^{76}$; and $R^{25}$, respectively) is shown below. Note that a preferred species may have the indicated preferred stereochemistry at one, both, or neither of the $R^2$ and $R^5$ positions. Furthermore, while the invention encompasses both cis and trans geometries, trans is preferred at the carbon-carbon double bond shown below.

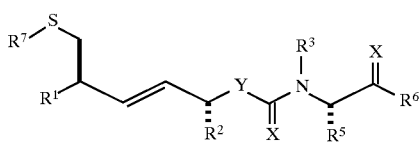

$R^{14}$, $R^{15}$, and $R^{16}$ (and analogous groups such as $R^{34}$, $R^{35}$, and $R^{36}$, respectively) may be ortho, meta, or para relative to a phenylene point of attachment.

The enzyme specificity of the inhibitor compounds of the invention is determined, in part, by the amino acid defined by the side chain of substituent $R^5$ (or analogous groups such as $R^{25}$). Generally, where the amino acid is one of the preferred amino acids (methionine, glutamine, or serine), the inhibitor is specific for FTase. Where the amino acid defined by the side chain of substituent $R^5$ is another amino acid, in particular leucine and phenylalanine, the inhibitor will generally inhibit GGTase. Compounds which inhibit FTase are preferred for their specificity. Potency and specificity for FTase and GGTase can be measured by methods well known in the art, including those disclosed herein, such as the in vitro inhibition assays in Example A below.

Preferred embodiments include compounds of formulae I–III (or IV–VI), wherein $R^1$ (or $R^{21}$) is $NH_2$ or $NHR^8$ (or $NHR^{28}$); $R^8$ (or $R^{28}$) is $C_{1-6}$ acyl, $C_{1-6}$ alkyl, or $C_{2-8}$ alkyloxycarbonyl; $R^2$ (or $R^{22}$) is H, $C_{1-8}$ alkyl, ($C_{6-10}$ aryl)($C_{0-3}$ alkyl), or ($C_{3-10}$ heteroaryl) ($C_{0-3}$ alkyl); $R^{17}$ (or $R^{37}$) is H, $C_{1-8}$ alkyl, ($C_{6-20}$ aryl) ($C_{0-3}$ alkyl), ($C_{3-10}$ heteroaryl) ($C_{0-3}$ alkyl), or ($C_{3-10}$ heterocyclic radical) ($C_{0-3}$ alkyl); $R^3$ (or $R^{23}$) is H, $C_{1-6}$ alkyl, or ($C_{6-12}$ aryl) ($C_{0-3}$ alkyl); $R^4$ (or $R^{24}$) is is $C_{3-8}$ cycloalkyl, ($C_{3-9}$ heterocyclic radical)($C_{0-3}$ alkyl), ($C_{6-12}$ aryl)-($C_{0-3}$ alkyl), or ($C_{3-9}$ heteroaryl) ($C_{0-3}$ alkyl), $R^5$(CH—)(C=O)$R^6$ (or $R^{25}$ (CH—)(C=O)$R^{26}$); wherein $R^5$ (or $R^{25}$) is $C_{1-6}$ alkyl, ($C_{3-9}$ heterocyclic radical) ($C_{0-3}$ alkyl), ($C_{3-9}$ heteroaryl) ($C_{0-3}$ alkyl), ($C_{0-3}$ alkyl) sulfonyl($C_{0-3}$ alkyl), ($C_{0-3}$ alkyl)sulfoxide($C_{0-3}$ alkyl) or a side chain of an amino acid selected from the group glycine, alanine, valine, leucine, isoleucine, serine, threonine, aspartic acid, asparagine, lysine, glutamic acid, glutamine, arginine, cysteine, methionine, phenylalanine, and proline; $R^6$ (or $R^{26}$) is H, $NH_2$, NHOH, $NHR^{10}$ (or $NHR^{30}$), $OR^{12}$ (or $OR^{32}$), $C_{3-9}$ heterocyclic radical, $C_{3-9}$ heteroaryl; wherein $R^{10}$ (or $R^{30}$) is $C_{1-6}$ alkyl; $R^{12}$ (or $R^{32}$) is H, $C_{1-6}$ alkyl, or ($C_{1-6}$ acyl)oxy($C_{1-6}$ alkyl); $R^{14}$ (or $R^{34}$) is H, halide, hydroxy, $C_{1-6}$ alkyl, $C_{2-6}$ alkenyl, $C_{2-6}$ alkynyl, $C_{1-6}$ alkoxy, ($C_{6-10}$ aryl)($C_{0-3}$ alkyl), ($C_{3-9}$ heterocyclic radical)-($C_{0-3}$ alkyl), ($C_{3-9}$ heteroaryl) ($C_{0-3}$ alkyl); $R^{18}$ (or $R^{38}$) is H. $C_{1-6}$ alkyl, ($C_{3-9}$ heterocyclic radical) ($C_{0-3}$ alkyl), ($C_{3-9}$ heteroaryl) ($C_{0-3}$ alkyl), or ($C_{6-12}$ aryl) ($C_{0-3}$ alkyl); $R^7$ (or $R^{27}$) is an organic moiety having fewer than 30 carbon atoms, and more preferably, H, a thiol-protecting group, or a moiety set forth in one of the formulae I–III (or IV–VI) wherein $R^7$ (or $R^{37}$) is deleted; or combinations of the above.

Certain embodiments include compounds of formulae I–III (or IV–VI), wherein $R^1$ (or $R^{21}$) is $NH_2$ or NH-($C_{1-6}$ acyl); $R^2$ (or $R^{22}$) is H, 2-butyl, t-butyl, isopropyl, or benzyl; $R^3$ (or $R^{23}$) is H or methyl; $R^{17}$ (or $R^{37}$) is isopropyl or benzyl; $R^4$ (or $R^{24}$) is 2-butanolidyl, 2-pyridinyl, 4-oxa-pyrazin-N-yl, or $R^5$(CH—)(C=O)$R^6$ (or $R^{25}$(CH—)(C=O)$R^{26}$); wherein $R^5$ (or $R^{25}$) is (2-thiophenyl)methyl, methylsulfonylethyl, or a side chain of methionine (2-(methylmercapto)ethyl), glutamine (—$CH_2$—$CH_2$—(C=O)—$NH_2$), serine (hydroxymethyl), or leucine (isobutyl), and $R^6$ (or $R^{26}$) is $NHR^{10}$ (or $NHR^{30}$), $OR^{12}$ (or $OR^{32}$); $R^{10}$ (or $R^{30}$) is t-butyl; $R^{12}$ (or $R^{32}$) is H, methyl, ethyl, or isobutyl; $R^{14}$ (or $R^{34}$) is methyl, ethyl, ethenyl, methoxy, ethoxy, propenyl, phenyl, benzyl, 2-furyl, 3-furyl, o-, m- or p-methoxyphenyl, m- or p-(trifluoromethyl)phenyl, 2-thienyl, 3-thienyl; $R^{18}$ (or $R^{38}$) is 2-thienylmethyl, 2-butyl, or benzyl; $R^7$ (or $R^{27}$) is an organic moiety having fewer than 30 carbon atoms, and more preferably, H, a thiol-protecting group, or a moiety set forth in one of the formulae I–III (or IV–VI) wherein $R^7$ (or $R^{37}$) is deleted; or combinations of the above.

In certain embodiments, leaving group $L^n$ is halide (iodide and bromide are preferred); hydroxy; $C_{1-12}$ alkylsulfonyloxy such as mesylate and trifluoromethanesulfonate; $C_{6-20}$ arylsulfonyloxy such as p-toluenesulfonate, p-nitrobenzenesulfonate; benzoate and benzoate derivatives such as p-nitrobenzoate; $C_{1-12}$ carbamoyl; $C_{1-12}$ acyloxy; $C_{7-40}$ aryl-alkyl such as p-nitrobenzyl; $C_{7-20}$ arylalkyloxy; $C_{1-12}$ alkoxy; $C_{2-12}$ alkyloxycarbonyl such as BOC; and $C_{2-5}$ haloalkylcarbonyloxy such as trifluoroacetate.

One embodiment is a compound of formula II:

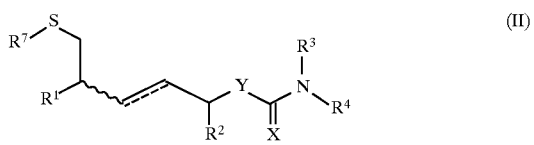

(II)

wherein $R^1$ is H, $NHR^8$, or $NR^8R^9$, wherein $R^8$ is H, $C_{1-6}$ alkyl, $C_{1-6}$ acyl, $C_{2-14}$ alkyloxycarbonyl or any other amino-protecting group, and $R^9$ is $C_{1-6}$ alkyl, $C_{1-6}$ acyl, $C_{2-14}$ alkyloxycarbonyl or, when taken together with $R^7$, a bifunctional thiol-protecting group; and $R^7$ is H; a thiol protecting group or, when taken together with $R^9$, a bifunctional thiol-protecting group; or a moiety set forth in the above generic formula (II) wherein $R^7$ is deleted, said compound being a symmetrical disulfide dimer or an asymmetrical disulfide; or a pharmaceutically acceptable salt thereof.

Another embodiment is a compound of formula III:

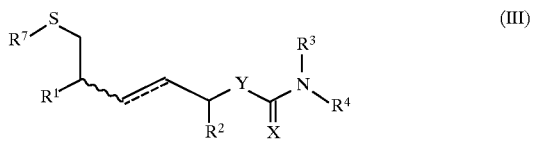

(III)

wherein $R^1$ is $NHR^8$ or $NR^8R^9$, wherein $R^8$ is $C_{1-6}$ alkyl, $C_{1-6}$ acyl, $C_{2-14}$ alkyloxycarbonyl, or any other amino-protecting group, and $R^9$ is $C_{1-6}$ alkyl, $C_{1-6}$ acyl, $C_{2-14}$ alkyloxycarbonyl or, when taken together with $R^7$, a bifunctional thiol-protecting group; $R^6$ is H, $NH_{21}$ NHOH, $C_{3-10}$ heterocyclic radical, $C_{3-10}$ heteroaryl, $NHR^{10}$, $NR^{10}R^{11}$, $OR^{12}$, $NR^{10}OR^{11}$, or $NHOR^{13}$, (wherein each of $R^{10}$ and $R^{11}$, independently, is $C_{1-6}$ alkyl, ($C_{3-16}$ heterocyclic radical) ($C_{0-6}$ alkyl), $C_{2-14}$ alkyloxycarbonyl, or ($C_{3-16}$ heteroaryl) ($C_{1-6}$ alkyl)), $R^{12}$ is $C_{1-6}$ alkyl, ($C_{1-12}$ acyl)oxy($C_{1-12}$ alkyl), ($C_{1-12}$ alkyl)oxy($C_{1-12}$ alkyl), $C_{2-14}$ alkyloxycarbonyl, or where $R^4$ is $R^5(CH—)(C=O)OR^{12}$, any other carboxyl-protecting group, or where $R^4$ is $R^5(CH—)(CH_2)OR^{12}$, any other hydroxyl-protecting group, and $R^{13}$ is H, $C_{1-6}$ alkyl, or ($C_{6-40}$ aryl) ($C_{0-6}$ alkyl); $R^7$ is a thiol-protecting group, or, when taken together with $R^9$, a bifunctional thiol-protecting group; or a moiety set forth in the above generic formula (III) wherein R7 is deleted, said compound being a symmetrical disulfide dimer or an asymmetrical disulfide.

Another embodiment is a compound of formula IV:

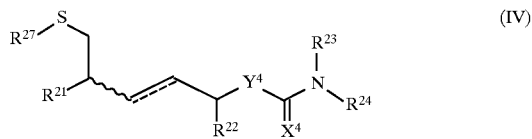

(IV)

wherein $R^{21}$ is H, $NH_2$, $NHR^{28}$, or $NR^{28}R^{29}$, wherein each $R^{28}$ and $R^{29}$, independently, is $C_{1-6}$ alkyl, $C_{1-6}$ acyl, or $C_{2-12}$ alkyloxycarbonyl; $R^{22}$ is H, $C_{1-8}$ alkyl, ($C_{6-40}$ aryl)-($C_{0-6}$ alkyl), or ($C_{3-10}$ heteroaryl) ($C_{0-6}$ alkyl); $R^{23}$ is H, $C_{1-8}$ alkyl, or ($C_{6-40}$ aryl) ($C_{0-6}$ alkyl) ; $R^{24}$ is $C_{3-16}$ cycloalkyl, ($C_{6-12}$ aryl) ($C_{0-6}$ alkyl), ($C_{3-6}$ heterocyclic radical)($C_{0-6}$ alkyl), ($C_{3-10}$ heteroaryl)-($C_{0-6}$ alkyl), $R^{25}(CH—)$ $(C=O)R^{26}$, $R^{25}$ $(CH—)$ $(C=S)R^{26}$, $R^{25}(CH—)(CH_2)R^{26}$, or $R^{25}(CH_2—)$, wherein $R^{25}$ is $C_{1-6}$ alkyl, ($C_{6-12}$ aryl)($C_{0-6}$ alkyl), ($C_{3-10}$ heterocyclic radical)-($C_{0-6}$ alkyl), ($C_{3-10}$ heteroaryl) ($C_{0-6}$ alkyl), hydroxymethyl, $—(CH_2)_n—A^4$ $—(CH_2)_m—CH_3$, $—(CH_2)_n(C=O)NH_2$, or $—(CH_2)_n(C=O)NH-(CH_2)_mCH_3$ (wherein $A^4$ is O, S, SO, or $SO_2$, n is 0, 1, 2 or 3, and m is 0, 1, or 2), or any other side chain of a naturally occurring amino acid; and $R^{26}$ is H, $NH_2$, NHOH, $C_{3-16}$ heterocyclic radical, $C_{3-16}$ heteroaryl, $NHR^{30}$, $NR^{30}R^{31}$, $OR^{32}$, $NR^{30}OR^{33}$, or $NHOR^{33}$, wherein each of $R^{30}$ and $R^{31}$, independently, is $C_{1-6}$ alkyl, ($C_{6-12}$ aryl) ($C_{0-6}$ alkyl), ($C_{3-16}$ heterocyclic radical) ($C_{0-6}$ alkyl), ($C_{3-16}$ heteroaryl) ($C_{0-6}$ alkyl), $C_{2-14}$ alkyloxycarbonyl, or where $R^{24}$ is $R^{25}(CH—)$ $(CH_2)R^{26}$, any amino-protecting group, $R^{32}$ is H, $C_{1-6}$ alkyl, ($C_{1-12}$ acyl)oxy($C_{1-12}$ alkyl), or ($C_{1-12}$ alkyl)oxy($C_{1-12}$ alkyl), and $R^{33}$ is H, $C_{1-6}$ alkyl, or ($C_{6-40}$ aryl) ($C_{0-6}$ alkyl); $X^4$ is $=O$, $=S$, or two singly-bonded H; $Y^4$ is selected from the following five formulae:

(vi)

wherein $R^{34}$ is H, halide, hydroxy, $C_{1-6}$ alkyl, $C_{2-6}$ alkenyl, $C_{2-6}$ alkynyl, $C_{1-2}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

(vii)

wherein $R^{35}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

(viii)

wherein $R^{36}$ is H, halide, hydroxy, $C_{1-6}$ alkyl, $C_{2-6}$ alkenyl, $c_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

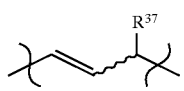

(ix)

wherein $R^{37}$ is H, $C_{1-8}$ alkyl, $(C_{6-40}$ aryl) $(C_{0-6}$ alkyl), or $(C_{3-10}$ heteroaryl) $(C_{0-6}$ alkyl), $(C_{3-10}$ heterocyclic radical) $(C_{0-6}$ alkyl); and

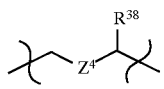

(x)

wherein $R^{38}$ is H, $C_{1-8}$ alkyl, $(C_{6-40}$ aryl) $(C_{0-6}$ alkyl) $(C_{3-10}$ heterocyclic radical) $(C_{0-6}$ alkyl), or $(C_{3-10}$ heteroaryl) $(C_{0-6}$ alkyl); and $Z^4$ is O, S, SO, $SO_2$, or $NR^{39}$ wherein $R^{39}$ is H, $C_{1-6}$ alkyl, $C_{1-6}$ acyl, $(C_{6-40}$ aryl)-$(C_{0-6}$ alkyl), $(C_{3-12}$ heterocyclic radical) $(C_{0-6}$ alkyl), $(C_{3-10}$ heteroaryl) $(C_{0-6}$ alkyl), or $C_{2-14}$ alkyloxycarbonyl; or wherein $R^{38}$ and $NR^{39}$ taken together form a bifunctional $C_{6-40}$ aryl, a bifunctional $C_{3-12}$ heterocyclic radical, or a bifunctional $C_{3-12}$ heteroaryl; and $R^{27}$ is H; a thiol protecting group; or a moiety set forth in the above generic formula (IV) wherein $R^{27}$ is deleted, said compound being a symmetrical disulfide dimer or an asymmetrical disulfide; or a pharmaceutically acceptable salt thereof.

Another embodiment of the invention is a compound of formula V:

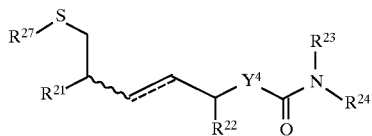

(V)

wherein $R^{21}$ is H, $NH_2$, or $NHR^{28}$, wherein $R^{28}$ is $C_{1-6}$ alkyl, $C_{1-6}$ acyl, or $C_{2-14}$ alkyloxycarbonyl; $R^{23}$ is H or methyl; $R^{24}$ is $R^{25}(CH-)(C=O)R^{26}$, $R^{25}(CH-)(C=S)R^{26}$, or $R^{25}(CH_2-)$; and $Y^4$ is selected from the following three formulae:

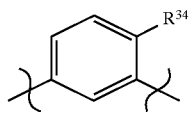

(xi)

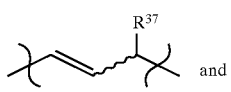

and (xii)

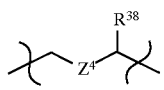

(xiii)

wherein $Z^4$ is O, S, or $NR^{39}$, wherein $R^{39}$ is H, $C_{1-6}$ alkyl, or $C_{1-6}$ acyl; or wherein $R^{38}$ and $NR^{39}$ taken together form a bifunctional $C_{6-40}$ aryl, a bifunctional $C_{3-12}$ heterocyclic radical, or a bifunctional $C_{3-12}$ heteroaryl.

Another embodiment is a compound of formula VI:

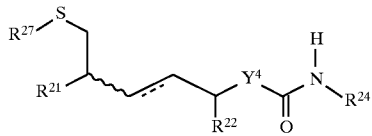

(VI)

wherein $R^{21}$ is $NH_2$ or $NHR^{28}$, wherein $R^{28}$ is $C_{1-6}$ alkyl, $C_{1-6}$ acyl, or $C_{2-14}$ alkyloxycarbonyl; $R^{22}$ is H or $C_{1-8}$ alkyl; $R^{24}$ is $C_{3-16}$ heterocyclic radical, $C_{3-16}$ heteroaryl, $R^{25}(CH-)(C=O)R^{26}$, or $R^{25}(CH-)(C=S)R^{26}$, wherein $R^{25}$ is $C_{1-6}$ alkyl, hydroxymethyl, $-(CH_2)_n-A^4-(CH_2)_m-CH_3$, $-(CH_2)_n(C=O)NH_2$, or $-(CH_2)_n(C=O)NH(CH_2)_mCH_3$ (wherein $A^4$ is O, S, SO, or $SO_2$, n is 0, 1, or 2, and m is 0 or 1), or any other side chain of a naturally occurring amino acid, and $R^{32}$ is H, $C_{1-6}$ alkyl, or $(C_{1-12}$ acyl)oxy$(C_{1-12}$ alkyl); and $Y^4$ is selected from the following three formulae:

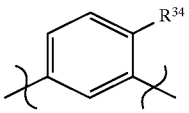

(xiv)

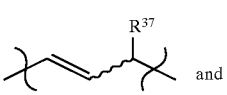

and (xv)

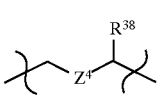

(xvi)

wherein $Z^4$ is O, S, or $NR^{39}$, wherein $R^{39}$ is H, $C_{1-6}$ alkyl, or $C_{1-6}$ acyl; or wherein $R^{38}$ and $NR^{39}$ taken together form a bifunctional $C_{6-40}$ aryl, a bifunctional $C_{3-12}$ heterocyclic radical, or a bifunctional $C_{3-12}$ heteroaryl.

Another embodiment is a compound of formula VII:

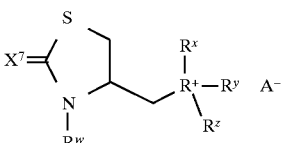

(VII)

wherein $X^7$ is O or S; $R^w$ is H, $C_{1-8}$ alkyl, $C_{1-8}$ acyl, or $C_{2-14}$ alkyloxycarbonyl; each of $R^x$, $R^y$, and $R^z$, independently, is $C_{1-12}$ alkyl, $C_{3-12}$ cycloalkyl, $C_{6-20}$ aryl, $(C_{6-20}$ aryl) $(C_{1-12}$ alkyl), or $(C_{3-12}$ alkyl) $(C_{6-20}$ aryl); and $A^-$ is a counter-ion. In certain embodiments, $A^-$ is bromide, iodide, or chloride; $X^7$ is O; $R^w$ is H or methyl; and each of $R^x$, $R^y$, and $R^z$, independently, is $(C_{6-10}$ aryl) $(C_{0-6}$ alkyl), and preferably each of $R^x$, $R^y$, and $R^z$ is phenyl.

Another embodiment is a compound of formula VIII:

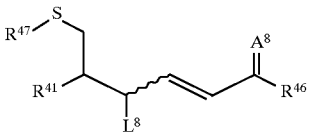

(VIII)

wherein:

$R^{41}$ is H, $NH^2$, $NHR^{42}$, or $NR^{42}R^{43}$, wherein $R^{42}$ is $C_{1-6}$ alkyl, $C_{1-6}$ acyl, $C_{2-14}$ alkyloxycarbonyl, or any other amino-protecting group, and $R^{43}$ is $C_{1-6}$ alkyl, $C_{1-6}$ acyl, $C_{2-14}$ alkyloxycarbonyl or, when taken together with $R^{47}$, is a bifunctional thiol-protecting group; $L^8$ is halide, hydroxy, $C_{1-12}$ alkoxy, $C_{1-12}$ alkylsulfonyloxy, $C_{6-20}$ arylsulfonyloxy, $C_{1-12}$ acyloxy, $C_{1-12}$ carbamoyl, or any other activated leaving group; $A^8$ is =O, =S, or two singly-bonded H; $R^{46}$ is H, $NH_2$, NHOH, $C_{3-10}$ heterocyclic radical, $C_{3-10}$ heteroaryl, $NHR^{44}$, $NR^{44}R^{45}$, $OR^{48}$, $NR^{44}OR^{45}$, $NHOR^{49}$, or any other carboxyl-protecting group, wherein each of $R^{44}$ and $R^{45}$, independently, is $C_{1-6}$ alkyl, $(C_{6-12}$ aryl) $(C_{0-6}$ alkyl), $(C_{3-16}$ heterocyclic radical) $(C_{0-6}$ alkyl), $(C_{3-16}$ heteroaryl) $(C_{0-6}$ alkyl), or $C_{2-14}$ alkyloxycarbonyl, $R^{48}$ is H, $C_{1-6}$ alkyl, $(C_{1-12}$ acyl)oxy$(C_{1-12}$ alkyl), $(C_{1-12}$ alkyl)oxy-$(C_{1-12}$ alkyl), or any other carboxyl- or hydroxyl-protecting group, and $R^{49}$ is H, or $C_{1-6}$ alkyl, provided that where $A^8$ is two singly-bonded H, $R^{46}$ is such that the C atom bonded to both $A^8$ and $R^{46}$ is bonded to either a N or O atom of $R^{46}$;

and $R^{47}$ is H; a thiol-protecting group or, when taken together with $R^{43}$, a bifunctional thiol-protecting group; or a moiety set forth in the above generic formula (VIII) wherein $R^{47}$ is deleted, said compound being a symmetrical disulfide dimer or an asymmetrical disulfide.

Another embodiment is a compound of formula IX:

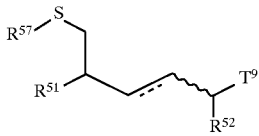
(IX)

wherein: $R^{51}$ is H, $NHR^{53}$, or $NR^{53}R^{54}$, wherein $R^{53}$ is H, $C_{1-6}$ alkyl, $C_{1-6}$ acyl, $C_{2-14}$ alkyloxycarbonyl, or any other amino-protecting group, and $R^{54}$ is $C_{1-6}$ alkyl, $C_{1-6}$ acyl, $C_{2-14}$ alkyloxycarbonyl or, when taken together with $R^{57}$, a bifunctional thiol-protecting group; $R^{52}$ is H, $C_{1-8}$ alkyl, $(C_{6-40}$ aryl$)(C_{0-6}$ alkyl$)$, or $(C_{3-10}$ heteroaryl$)(C_{0-6}$ alkyl$)$; $T^9$ is selected from the following four formulae:

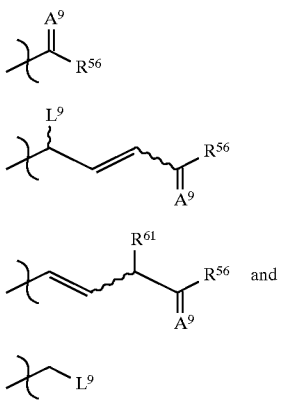

(xvii)

(xviii)

(xix) and (xx)

wherein $L^9$ is halide, hydroxy, $C_{1-12}$ alkoxy, $C_{1-12}$ alkylsulfonyloxy, $C_{6-12}$c arylsulfonyloxy, $C_{1-12}$ acyloxy, $C_{1-12}$ carbamoyl, or any other activated leaving group; $A^9$ is =O, =S, or two singly-bonded H; $R^{56}$ is H, $NH_2$, NHOH, $C_{3-10}$ heterocyclic radical, $C_{3-10}$ heteroaryl, $NHR^{55}$, $NR^{55}R^{58}$, $OR^{59}$, $NR^{55}OR^{58}$, $NHOR^{60}$, or any other carboxyl-protecting group, wherein each $R^{55}$ and $R^{58}$, independently, is $C_{1-6}$ alkyl, $(C_{6-12}$ aryl$)$ $(C_{0-6}$ alkyl$)$, $(C_{3-16}$ heterocyclic radical$)$ $(C_{0-6}$ alkyl$)$, $(C_{3-16}$ heteroaryl$)$-$(C_{0-6}$ alkyl$)$, or $C_{2-14}$ alkyloxycarbonyl, $R^{59}$ is H, $C_{1-6}$ alkyl, $(C_{1-12}$ acyl$)$oxy$(C_{1-12}$ alkyl$)$, or $(C_{1-12}$ alkyl$)$oxy-$(C_{1-12}$ alkyl$)$, and $R^{60}$ is H or $C_{1-6}$ alkyl; provided that where $A^9$ is two singly-bonded H, $R^{56}$ is selected such that the carbon atom bonded to both $A^9$ and $R^{56}$ is bonded to either a nitrogen or oxygen atom of $R^{56}$; $R^{61}$ is H, $C_{1-8}$ alkyl, $(C_{6-40}$ aryl$)$ $(C_{0-6}$ alkyl$)$, or $(C_{3-10}$ heteroaryl$)$-$(C_{0-6}$ alkyl$)$; and $R^{57}$ is H; a thiol-protecting group or, taken together with $R^{54}$, a bifunctional thiol-protecting group; or a moiety set forth in the above generic formula (IX) wherein $R^{57}$ is deleted, said compound being a symmetrical disulfide dimer or an asymmetrical disulfide.

Another embodiment is a compound of formula X:

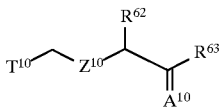
(X)

wherein: $T^{10}$ is selected from the following three formulae:

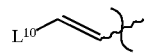
(xxi)

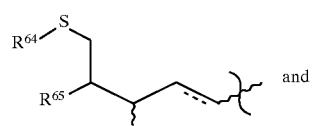
(xxii)

and

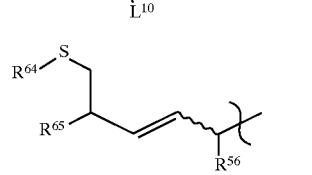
(xxiii)

wherein $L^{10}$ is halide, $C_{1-12}$ alkoxy, $C_{1-12}$ alkylsulfonyloxy, $C_{6-20}$ arylsulfonyloxy, $C_{1-12}$ acyloxy, $C_{1-12}$ carbamoyl, or any other activated leaving group; $R^{65}$ is H, $NH_2$, $NHR^{67}$, or $NR^{67}R^{68}$, wherein $R^{67}$ is $C_{1-6}$ alkyl, $C_{1-6}$ acyl, $C_{2-14}$ alkyloxycarbonyl or any other amino-protecting group, and $R^{68}$ is $C_{1-6}$ alkyl, $C_{1-6}$ acyl, $C_{2-14}$ alkyloxycarbonyl or, when taken together with $R^{64}$, a bifunctional thiol-protecting group; $R^{64}$ is H; a thiol-protecting group or, when taken together with $R^{68}$, a bifunctional thiol-protecting group; or a moiety set forth in the above generic formula (X) wherein $R^{64}$ is deleted, said compound being a symmetrical disulfide dimer or an asymmetrical disulfide; $R^{66}$ is H, $C_{1-8}$ alkyl, $(C_{6-40}$ aryl$)$ $(C_{0-6}$ alkyl$)$, or $C_{3-10}$ heteroaryl$)$ $(C_{0-6}$ alkyl$)$; $R^{63}$ is H, $NH_2$, NHOH, $C_{3-10}$ heterocyclic radical, $C_{3-10}$ heteroaryl, $NHR^{69}$, $NR^{69}R^{70}$, $OR^{71}$, $NR^{69}OR^{70}$, $NHOR^{72}$, or any other carboxyl-protecting group, wherein each of $R^{69}$ and $R^{70}$, independently, is $C_{1-6}$ alkyl, $(C_{3-16}$ heterocyclic radical$)(C_{0-6}$ alkyl$)$, or $(C_{3-16}$ heteroaryl$)(C_{0-6}$ alkyl$)$, $R^{71}$ is H, $C_{1-6}$ alkyl, $(C_{1-12}$ acyl$)$oxy$(C_{1-12}$ alkyl$)$, or $(C_{1-12}$ alkyl$)$ oxy$(C_{1-12}$ alkyl$)$, and $R^{72}$ is H or $C_{1-6}$ alkyl; provided that where $A^{10}$ is two singly-bonded H, $R^{63}$ is selected such that the carbon atom bonded to both $A^{10}$ and $R^{63}$ is bonded to either a nitrogen or oxygen atom of $R^{63}$; $A^{10}$ is O, S, or two singly-bonded H; and $R^{62}$ is H, $C_{1-8}$ alkyl, $(C_{6-40}$ aryl$)(C_{0-6}$ alkyl$)$, $(C_{3-10}$ heterocyclic radical$)(C_{0-6}$ alkyl$)$, or $(C_{3-10}$ heteroaryl$)$ $(C_{0-6}$ alkyl$)$; and $Z^{10}$ is O, S, SO, $SO_2$, or $NR^{73}$ wherein $R^{73}$ is H, $C_{1-6}$ alkyl, $C_{1-6}$ acyl, $(C_{6-40}$ aryl$)$ $(C_{0-6}$ alkyl$)$, $(C_{3-10}$ heteroaryl$)$-$(C_{0-6}$ alkyl$)$, or $C_{2-14}$ alkyloxycarbonyl.

Another embodiment is a compound of formula XI:

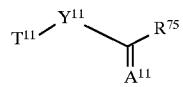
(XI)

wherein: $T^{11}$ is selected from H—(C=O)—, H—(C=O)—CH($R^{76}$)—,

(xxiv)

and

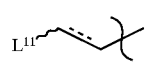
(xxv)

wherein $R^{75}$ is H, $NH_2$, NHOH, $C_{3-16}$ heterocyclic radical, $C_{3-16}$ heteroaryl, $NHR^{81}$, $NR^{81}R^{82}$, $OR^{83}$, $NR^{81}OR^{82}$, $NHOR^{84}$ or any other carboxyl-protecting group, wherein each $R^{81}$ and $R^{82}$, independently, is $C_{1-6}$ alkyl, $(C_{6-12}$ aryl$)$ $(C_{0-6}$ alkyl$)$, $(C_{3-16}$ heterocyclic radical$)$ $(C_{0-6}$ alkyl$)$, or $(C_{3-16}$ heteroaryl$)(C_{0-6}$ alkyl$)$, $R^{83}$ is H, $C_{1-6}$ alkyl, $(C_{1-12}$ acyl)oxy($C_{1-12}$ alkyl), or ($C_{1-12}$ alkyl)oxy-($C_{1-12}$ alkyl), and $R^{84}$ is H, or $C_{1-6}$ alkyl; $R^{76}$ is H, $C_{1-8}$ alkyl, ($C_{6-40}$ aryl)($C_{0-6}$ alkyl), or ($C_{3-10}$ heteroaryl) ($C_{0-6}$ alkyl); $R^{77}$ is H; a thiol-protecting group or, when taken together with $R^{80}$, a bifunctional thiol-protecting group; or a moiety set forth in the above generic formula (XI) wherein $R^{77}$ is deleted, said compound being a symmetrical disulfide dimer or an asymmetrical disulfide; $R^{78}$ is H, $NH_2$, $NHR^{79}$, or $NR^{79}R^{80}$, wherein $R^{79}$ is $C_{1-6}$ alkyl, $C_{1-6}$ acyl, $C_{2-14}$ alkyloxycarbonyl or any other amino-protecting group, and $R^{80}$ is $C_{1-6}$ alkyl, $C_{1-6}$ acyl, $C_{2-14}$ alkyloxycarbonyl or, when taken together with $R^{77}$, a bifunctional thiol-protecting group; $L^{11}$ is halide, $C_{1-12}$ alkylsulfonyloxy, $C_{6-20}$ arylsulfonyloxy, $C_{2-12}$ alkylcarbonyloxy, or any other activated leaving group; $y^{11}$ is selected from the following three formulae:

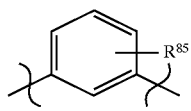

(xxvi)

wherein $R^{85}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

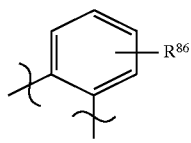

(xxvii)

wherein $R^{86}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy; and

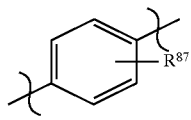

(xxviii)

wherein $R^{87}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy; and $A^{11}$ is O, S, or two singly-bonded H.

Another embodiment is a compound of formula VIII, wherein $R^{41}$ is H, $NH_2$, $NHR^{42}$, or $NR^{42}R^{43}$, wherein $R^{42}$ is $C_{1-6}$ alkyl, $C_{1-6}$ acyl, $C_{2-14}$ alkyloxycarbonyl, or any other amino-protecting group, and $R^{43}$ is $C_{1-6}$ alkyl, $C_{1-6}$ acyl, $C_{2-14}$ alkyloxycarbonyl or, when taken together with $R^{47}$, is a bifunctional thiol-protecting group; $L^8$ is halide, hydroxy, $C_{1-7}$ alkoxy, $C_{1-7}$ alkylsulfonyloxy, $C_{6-12}$ arylsulfonyloxy, $C_{1-12}$ acyloxy, $C_{1-12}$ carbamoyl, or any other activated leaving group; $A^8$ is =O, =S, or two singly-bonded H; $R^{46}$ is H, $NH_2$, NHOH, $C_{3-10}$ heterocyclic radical, $C_{3-10}$ heteroaryl, $NHR^{44}$, $NR^{44}R^{45}$, $OR^{48}$, $NR^{44}OR^{45}$, $NHOR^{49}$, or any other carboxyl-protecting group, wherein each of $R^{44}$ and $R^{45}$, independently, is $C_{1-6}$ alkyl, ($C_{6-10}$ aryl)($C_{0-3}$ alkyl), ($C_{3-10}$ heterocyclic radical)($C_{0-3}$ alkyl), or ($C_{3-10}$ heteroaryl)($C_{0-3}$ alkyl), $R^{48}$ is H, $C_{1-6}$ alkyl, ($C_{1-7}$ acyl)oxy($C_{1-6}$ alkyl), ($C_{1-6}$ alkyl)oxy($C_{1-6}$ alkyl), or any other carboxyl- or hydroxyl-protecting group, and $R^{49}$ is H, or $C_{1-6}$ alkyl, provided that where $A^8$ is two singly-bonded H, $R^{46}$ is such that the C atom bonded to both $A^8$ and $R^{46}$ is bonded to either a N or O atom of $R^{46}$; and $R^{47}$ is H; a thiol-protecting group or, when taken together with $R^{43}$, a bifunctional thiol-protecting group; or a moiety set forth in the above formula (VIII) wherein $R^{47}$ is deleted, said compound being a symmetrical disulfide dimer or an asymmetrical disulfide.

Another embodiment is a compound of formula IX, wherein $R^{51}$ is H, $NHR^{53}$, or $NR^{53}R^{54}$, wherein $R^{53}$ is H, $C_{1-6}$ alkyl, $C_{1-6}$ acyl, $C_{2-14}$ alkyloxycarbonyl, or any other amino-protecting group, and $R^{54}$ is $C_{1-6}$ alkyl, $C_{1-6}$ acyl, $C_{2-14}$ alkyloxycarbonyl or, when taken together with $R^{57}$, a bifunctional thiol-protecting group; $R^{52}$ is H, $C_{1-8}$ alkyl, ($C_{6-10}$ aryl)($C_{0-3}$ alkyl), or ($C_{3-10}$ heteroaryl)($C_{0-3}$ alkyl); wherein $L^9$ is halide, hydroxy, $C_{1-7}$ alkoxy, $C_{1-6}$ alkylsulfonyloxy, $C_{6-10}$ arylsulfonyloxy, $C_{1-7}$ acyloxy, $C_{1-7}$ carbamoyl, or any other activated leaving group; $A^9$ is =O, =S, or two singly-bonded H; $R^{56}$ is H, $NH_2$, NHOH, $C_{3-8}$ heterocyclic radical, $C_{3-8}$ heteroaryl, $NHR^{55}$, $NR^{55}R^{58}$, $OR^{59}$, $NR^{55}OR^{58}$, $NHOR^{60}$, or any other carboxyl-protecting group, wherein each $R^{55}$ and $R^{58}$, independently, is $C_{1-6}$ alkyl, ($C_{6-10}$ aryl) ($C_{0-3}$ alkyl), ($C_{3-10}$ heterocyclic radical) ($C_{0-3}$ alkyl), or ($C_{3-10}$ neteroaryl) ($C_{0-3}$ alkyl), $R^{59}$ is H, $C_{1-6}$ alkyl, ($C_{1-7}$ acyl)oxy($C_{1-7}$ alkyl), or ($C_{1-7}$ alkyl)-oxy($C_{1-7}$ alkyl), and $R^{60}$ is H or $C_{1-6}$ alkyl; provided that where $A^9$ is two singly-bonded H, $R^{56}$ is selected such that the carbon atom bonded to both $A^9$ and $R^{56}$ is bonded to either a nitrogen or oxygen atom of $R^{56}$; and $R^{61}$ is H, $C_{1-8}$ alkyl, ($C_{6-20}$ aryl)-($C_{0-3}$ alkyl), or ($C_{3-10}$ heteroaryl)-($C_{0-3}$ alkyl); $R^{57}$ is H; a thiol-protecting group or, taken together with $R^{54}$, a bifunctional thiol-protecting group; or a moiety set forth in the above formula (IX) wherein $R^{57}$ is deleted, said compound being a symmetrical disulfide dimer.

Another embodiment is a compound of formula X, wherein $L^{10}$ is halide, $C_{1-7}$ alkoxy, $C_{1-7}$ alkylsulfonyloxy, $C_{6-10}$ arylsulfonyloxy, $C_{1-7}$ acyloxy, $C_{1-7}$ carbamoyl, or any other activated leaving group; $R^{65}$ is H, $NH_2$, $NHR^{67}$, or $NR^{67}R^{68}$, wherein $R^{67}$ is $C_{1-6}$ alkyl, $C_{1-6}$ acyl, $C_{2-14}$ alkyloxycarbonyl or any other amino-protecting group, and $R^{68}$ is $C_{1-6}$ alkyl, $C_{1-6}$ acyl, $C_{2-14}$ alkyloxycarbonyl or, when taken together with $R^{64}$, a bifunctional thiol-protecting group; $R^{64}$ is H; a thiol-protecting group or, when taken together with $R^{68}$, a bifunctional thiol-protecting group; or a moiety set forth in the above generic formula (X) wherein $R^{64}$ is deleted, said compound being a symmetrical disulfide dimer or an asymmetrical disulfide; $R^{66}$ is H, $C_{1-8}$ alkyl, ($C_{6-20}$ aryl) ($C_{0-3}$ alkyl), or ($C_{3-10}$ heteroaryl) ($C_{0-3}$ alkyl); $R^{63}$ is H, $NH_2$, NHOH, $C_{3-10}$ heterocyclic radical, $C_{3-10}$ heteroaryl, $NHR^{69}$, $NR^{69}R^{70}$, $OR^{71}$, $NR^{69}OR^{70}$, $NHOR^{72}$, or any other carboxyl-protecting group, wherein each of $R^{69}$ and $R^{70}$, independently, is $C_{1-6}$ alkyl, ($C_{3-10}$ heterocyclic radical) ($C_{0-3}$ alkyl), or ($C_{3-10}$ heteroaryl) ($C_{0-3}$ alkyl), $R^{71}$ is H, $C_{1-6}$ alkyl, ($C_{1-7}$ acyl)oxy($C_{1-6}$ alkyl), or ($C_{1-6}$ alkyl)oxy($C_{1-6}$ alkyl), and $R^{72}$ is H or $C_{1-6}$ alkyl; provided that where $A^{10}$ is two singly-bonded H, $R^{63}$ is selected such that the carbon atom bonded to both $A^{10}$ and $R^{63}$ is bonded to either a nitrogen or oxygen atom of $R^{63}$; and $R^{62}$ is H, $C_{1-8}$ alkyl, ($C_{6-20}$ aryl) ($C_{0-3}$ alkyl), ($C_{3-10}$ heterocyclic radical) ($C_{0-3}$ alkyl), or ($C_{3-10}$ heteroaryl)($C_{0-3}$ alkyl); and $Z^{10}$ is O, S, SO, $SO_2$, or $NR^{73}$ wherein $R^{73}$ is H, $C_{1-6}$ alkyl, $C_{1-6}$ acyl, ($C_{6-20}$ aryl)-($C_{0-3}$ alkyl), ($C_{3-10}$ heteroaryl) ($C_{0-3}$ alkyl), or $C_{2-14}$ alkyloxycarbonyl.

Another embodiment is a compound of formula XI, wherein: $R^{75}$ is H, $NH_2$, NHOH, $C_{3-10}$ heterocyclic radical, $C_{3-10}$ heteroaryl, $NHR^{81}$, $NR^{81}R^{82}$, $OR^{83}$, $NR^{81}OR^{82}$, $NHOR^{84}$ or any other carboxyl-protecting group, wherein each $R^{81}$ and $R^{82}$, independently, is $C_{1-6}$ alkyl, ($C_{6-10}$ aryl) ($C_{0-3}$ alkyl), ($C_{3-10}$ heterocyclic radical) ($C_{0-3}$ alkyl), or ($C_{3-10}$ heteroaryl) ($C_{0-3}$ alkyl), $R^{83}$ is H, $C_{1-6}$ alkyl, ($C_{1-7}$ acyl)oxy($C_{1-6}$ alkyl), or ($C_{1-6}$ alkyl)oxy($C_{1-6}$ alkyl), and $R^{84}$ is H, or $C_{1-6}$ alkyl; $R^{76}$ is H, $C_{1-8}$ alkyl, ($C_{6-20}$ aryl) ($C_{0-3}$ alkyl), or ($C_{3-10}$ heteroaryl) ($C_{0-3}$ alkyl); $R^{77}$ is H; a thiol-protecting group or, when taken together with $R^{80}$, a bifunctional thiol-protecting group; or a moiety set forth in the above formula (XI) wherein $R^{77}$ is deleted, said compound being a symmetrical disulfide dimer; $R^{78}$ is H, $NH_2$, $NHR^{79}$, or $NR^{79}R^{80}$, wherein $R^{79}$ is $C_{1-6}$ alkyl, $C_{1-6}$ acyl, $C_{2-14}$ alkyloxycarbonyl or any other amino-protecting group, and $R^{80}$ is $C_{1-6}$ alkyl, $C_{1-6}$ acyl, $C_{2-14}$ alkyloxycarbonyl or, when taken together with $R^{77}$, a bifunctional thiol-protecting group; $L^{11}$ is halide, $C_{1-6}$ alkoxy, $C_{1-6}$ alkylsulfonyloxy, $C_{6-10}$ arylsulfonyloxy, $C_{1-7}$ acyloxy, $C_{1-7}$ carbamoyl, or any other activated leaving group; and $R^{85}$ is H. halide, hydroxy, $C_{1-6}$ alkyl, $C_{2-6}$ alkenyl, $C_{2-6}$ alkynyl, $C_{1-7}$ alkoxy, $C_{1-6}$ acyloxy, $C_{1-6}$ acyl, $C_{6-20}$ aryl, $C_{3-16}$ heterocyclic radical, $C_{3-16}$ heteroaryl, $C_{1-6}$ alkylsulfonyloxy, $C_{1-6}$ haloalkylsulfonyloxy, $C_{6-20}$ arylsulfonyloxy, or $C_{6-20}$ aryloxy.

Where any of the terms any other amino-protecting group, any other hydroxyl-protecting group, any other carboxyl-protecting group, or any other thiol-protecting group, is used, the term applies only where the designated amino, hydroxyl, carboxyl, or thiol group is evident. For example in formula (I), where $R^4$ is $R^5(CH{-})(C{=}O)R^6$, and $R^6$ is $OR^{12}$, $R^{12}$ can be a $C_{1-6}$ alkyl (to form an ester) or $R^{12}$ can be any other carboxyl-protecting group. Where $R^4$ is $R^5(CH{-})(CH_2)R^6$, a carboxyl group is not possible, although if $R^6$ is $NR^{10}OR^{11}$, then $R^{10}$ can be an amino-protecting group.

This invention is based, in part, on the structure-function data disclosed herein. Therefore another aspect of the invention encompasses any compound, including metabolic precursors of the inhibitor compounds of the invention, that contains an essential recognition moiety and an essential inhibitory moiety as disclosed herein. These essential moieties may also be in a masked form which is released by metabolic or other processes after administration to a patient. When metabolized or unmasked, these compounds inhibit the post-translational processing of ras proteins by FTase, GGTase, or both.

D. Synthesis

The invention also relates to methods of making the compounds disclosed herein. Schemes I–XI are synthetic pathways that have been used to make compounds PD331; PD331; R030D; PA041; PA091; PE021; PT011; PM061; R012M; PM031 and PM121; and R031M, respectively. These synthetic pathways can easily be modified by an organic chemist of ordinary skill to make the other related compounds disclosed herein.

One aspect of this invention is a method of making the disclosed compounds via any of the disclosed intermediates. These intermediates include synthetic intermediates (e.g., R007D, R011D, R019D, R020D, R023D, R029D, R003E, R005E, R004T, R003M–R006M, R017M, R025M, and R027M); partially-protected therapeutic compounds (e.g., R006A, R004A, R003A, R012A, R014D, and R023M); fully-protected therapeutic compounds (e.g., R024D, R007E, R001A, R007T, R013D, and R018M); and the disclosed Wittig reagents (e.g., R012M). The intermediates and inhibitor compounds of the invention can also be made by other methods known or easily developed by those in the art.

In another aspect of the invention, the intermediates disclosed herein (e.g., Wittig reagent R012M and related compounds) are used in a method of making compounds (particularly but not limited to inhibitors of isoprenyl transferases) which are not disclosed herein.

Synthetic experimental details and/or 400 MHz $^1$H NMR data are provided below in Examples 1–175 for over 95 inhibitor compounds which have been prepared. The number of inhibitor compounds does not include the many corresponding partially- and fully-protected intermediate compounds of the invention.

Scheme I

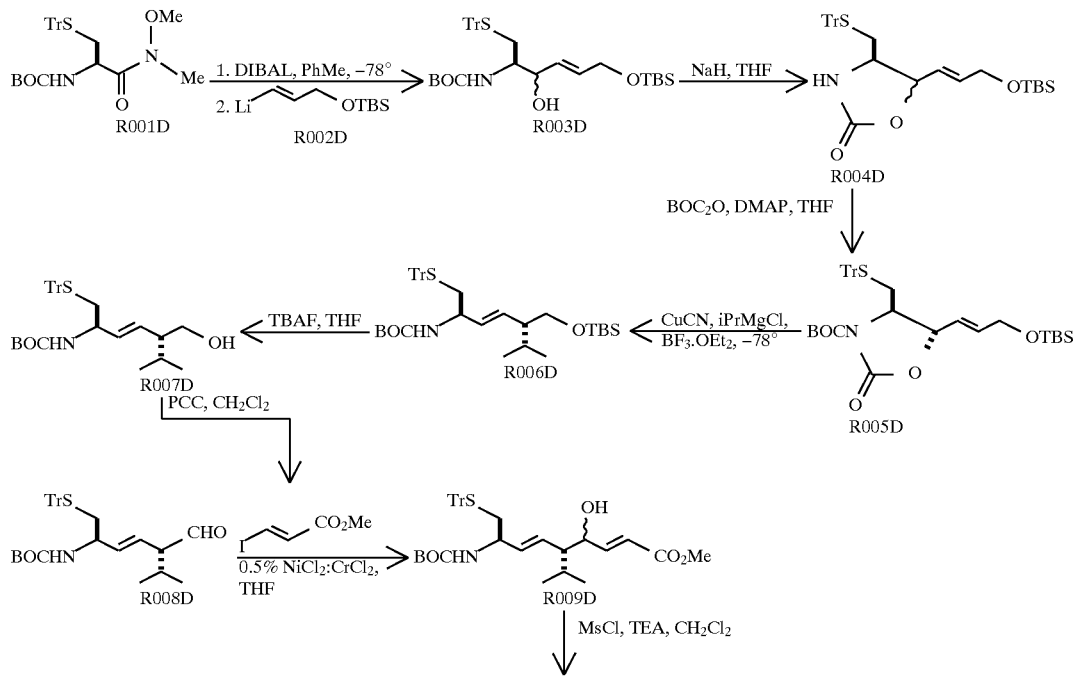

-continued
Scheme I
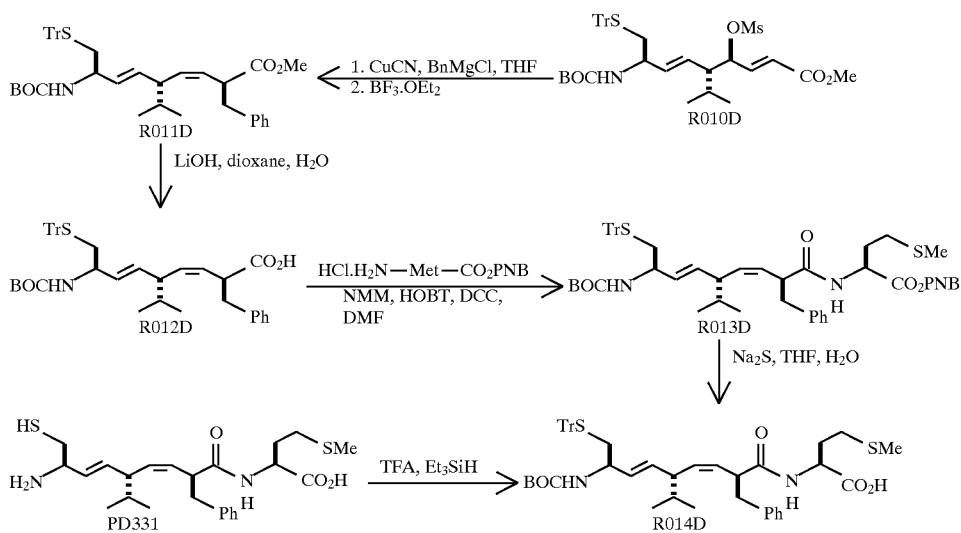
Scheme II
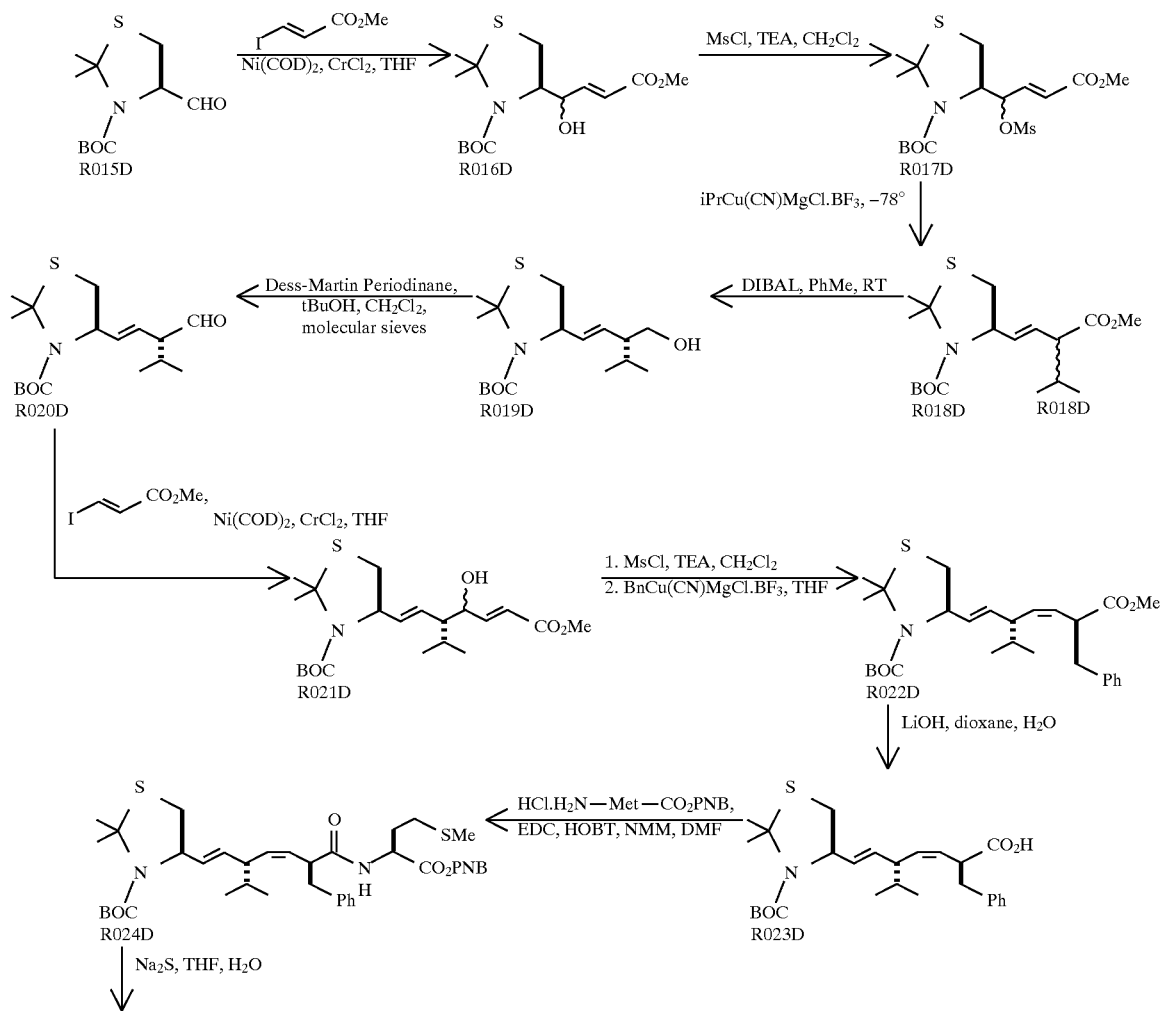

-continued
Scheme II
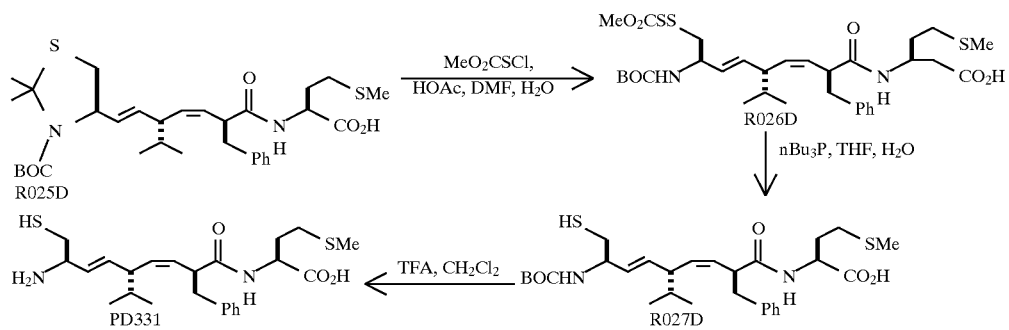
Scheme III
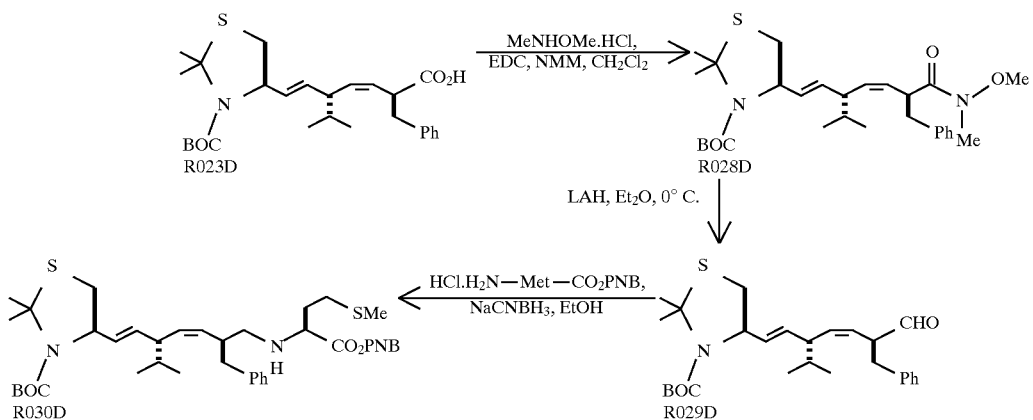
Scheme IV
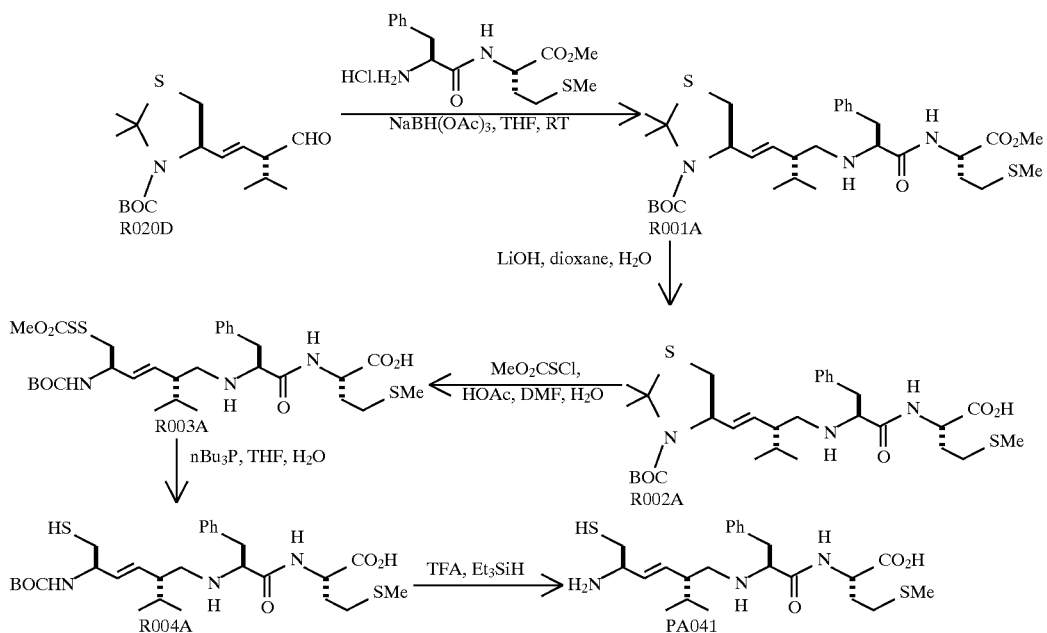

Scheme V
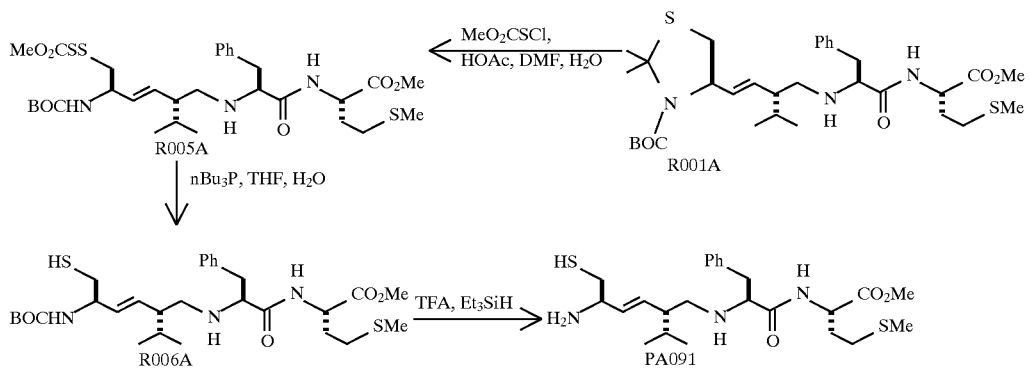
Scheme VI
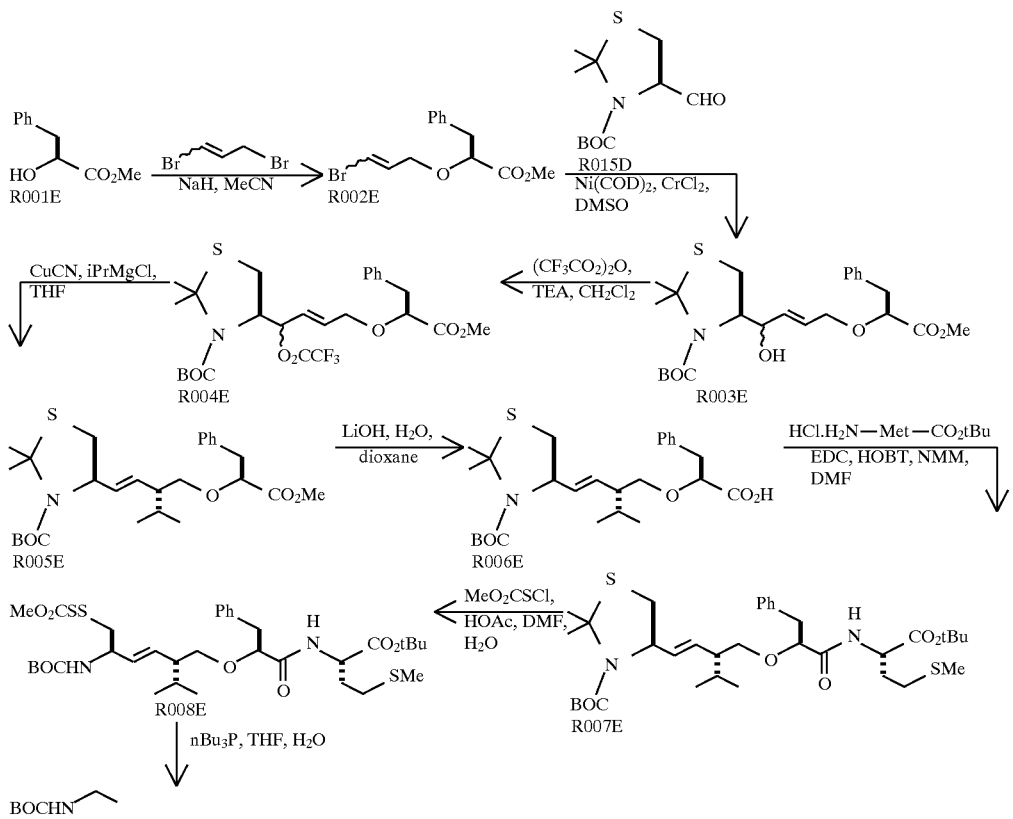
Scheme VII
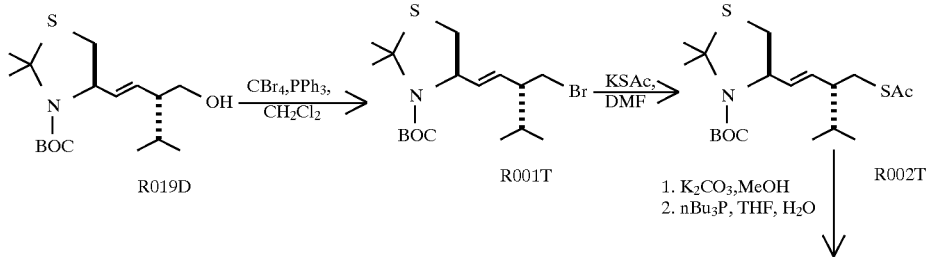

-continued
Scheme VII
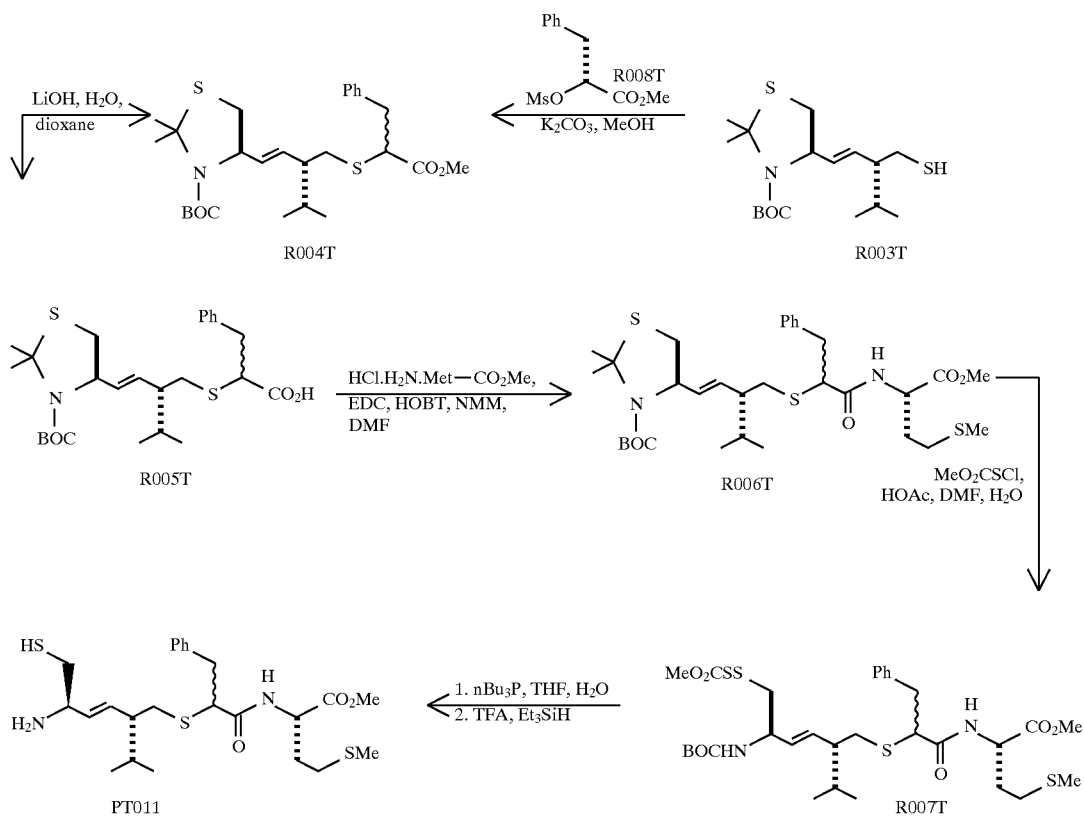
Scheme VIII
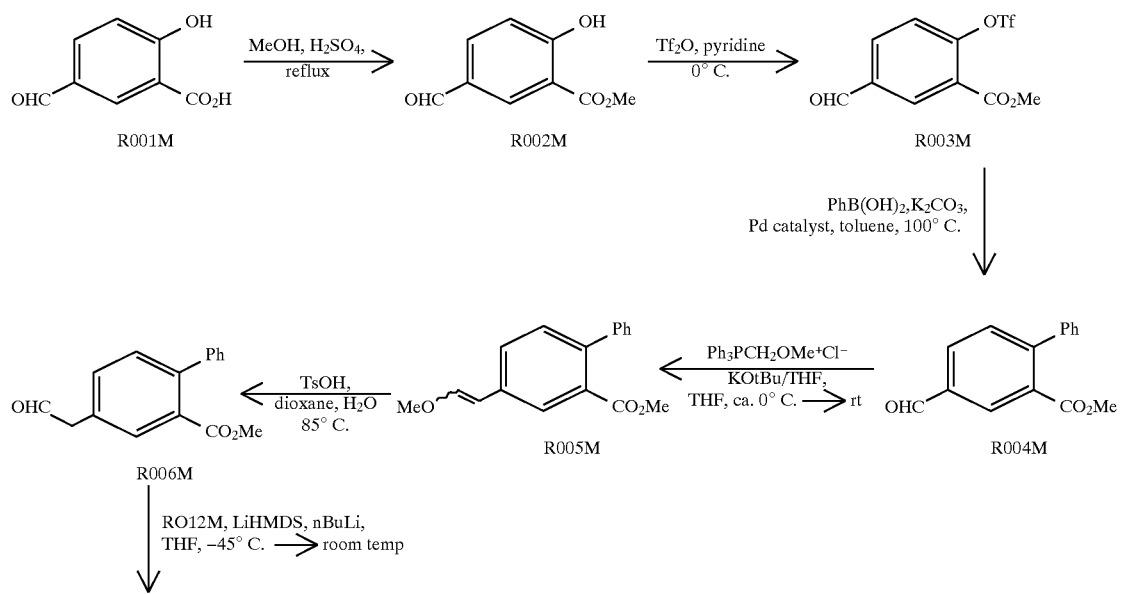

-continued
Scheme VIII
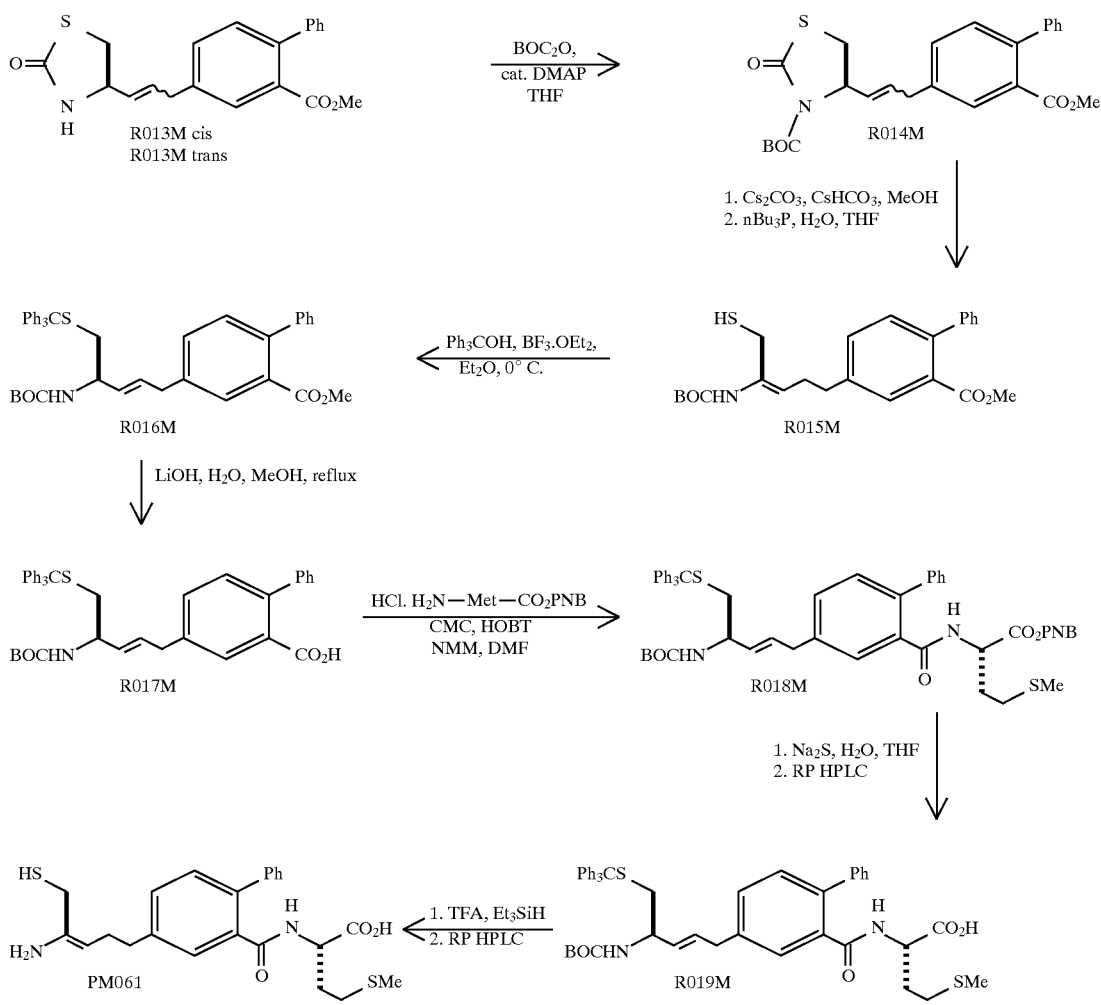
Scheme IX
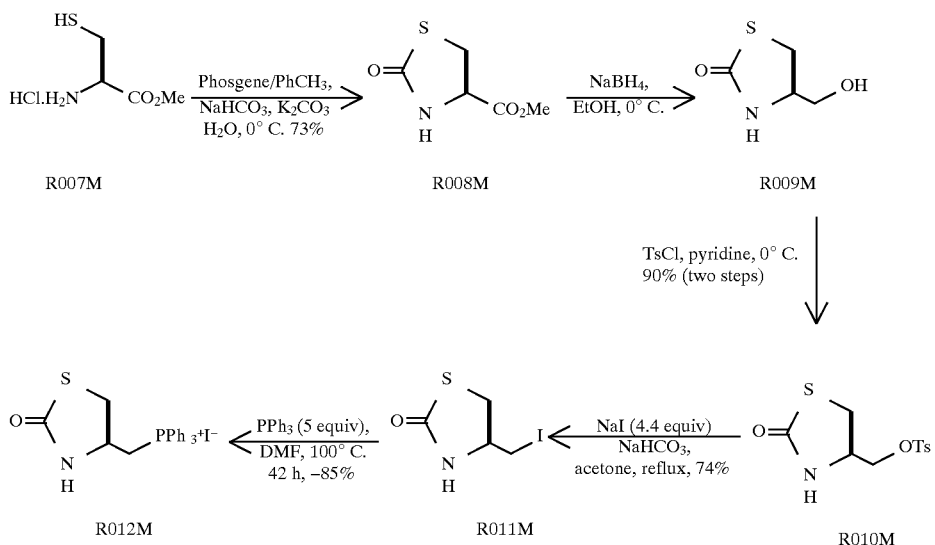

Scheme X
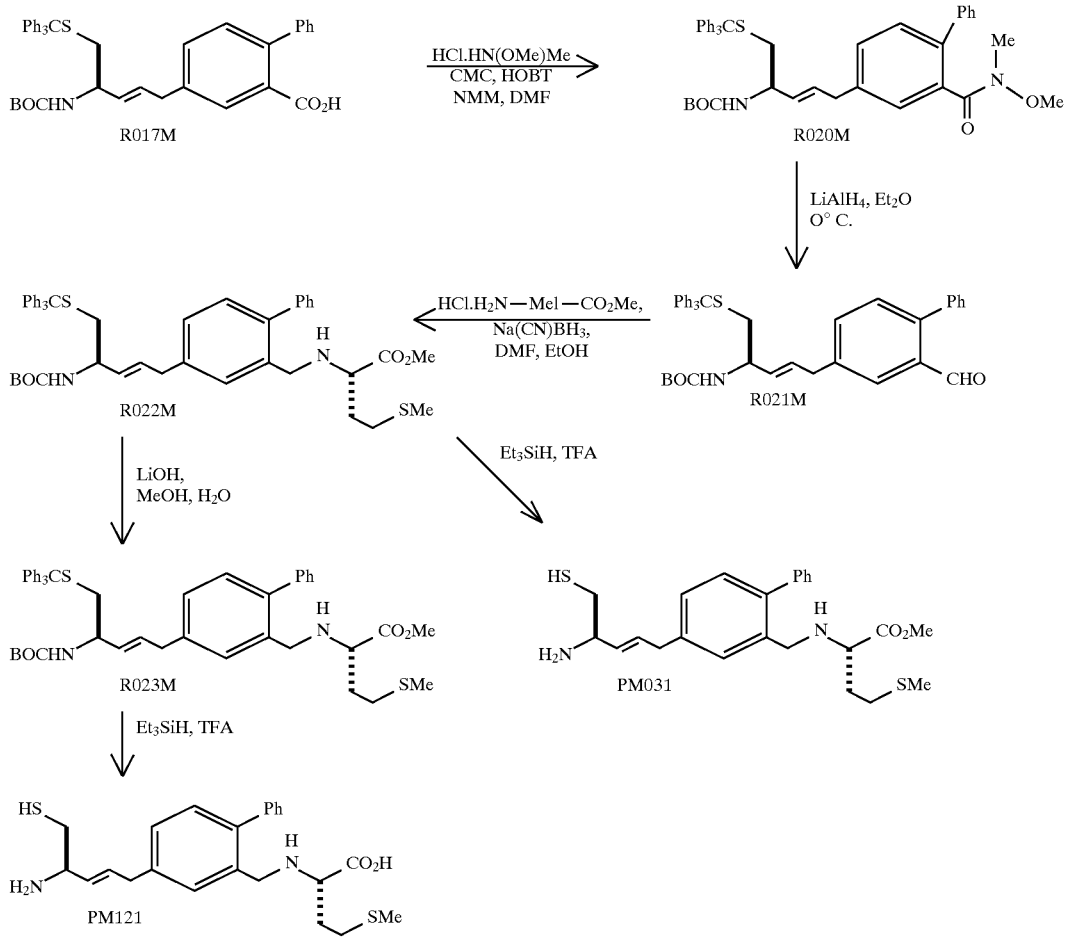
Scheme XI
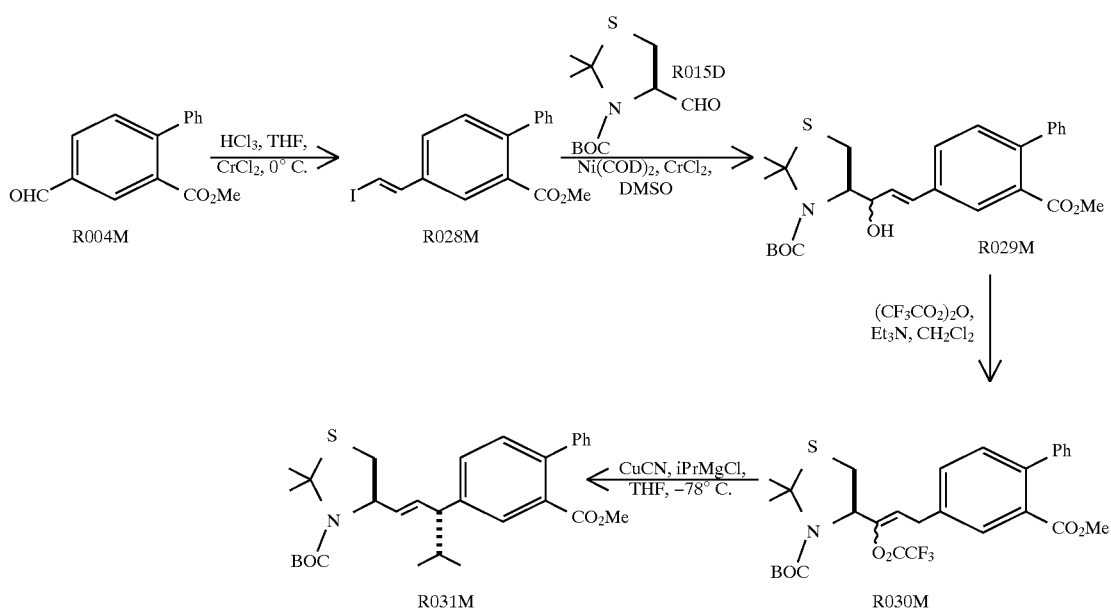

E. In vitro and in vivo data demonstrating utility

Ras proteins mediate the transformation of normal cells to cancer cells in many human cancers. Before becoming membrane associated and fully functional, ras proteins require post-translational processing. Compounds which inhibit prenylation will, therefore, inhibit the growth of ras-related cancers.

Compounds of the invention were screened in four art-accepted in vitro assays. First, each of over 60 tested inhibitor compounds was shown to inhibit FTase-mediated prenylation (Table 1). Second, each of over 60 tested compounds was shown to inhibit GGTase-mediated prenylation (Table 1). Third, each of over 60 tested compounds was shown to inhibit ras protein processing in whole cells (Table 2). Clearly, the compounds of the invention inhibit the prenylating activity of FTase, GGTase, or in most cases, both enzymes, with different potencies.

Furthermore, the compounds of the invention inhibit the anchorage-independent growth of ras-related tumor cell lines. For example, PD331 was shown to inhibit the growth of five tumor cell lines (Table 3). HT1080 is a neurofibrosarcoma with a N-ras mutation. MIApaca-2 is a pancreatic carcinoma and Sw620 is a colonic carcinoma; each of these has a K-ras mutation. T24 is a bladder carcinoma with a H-ras mutation; and zH1 is a H-ras-transformed NIH/3T3 mouse fibroblast. Additional compounds have been tested and have yielded positive results in these organ-specific or ras-protein specific anchorage-independent tumor cell models.

More importantly, an in vivo experiment demonstrated that compound PD331 effectively inhibited the growth of ras-associated tumors in mice (Table 4). The results of a second in vivo experiment demonstrated that another compound (PM061) effectively inhibited the growth of ras-associated tumors in mice (Table 5).

Thus, the ability of the compounds of the invention to inhibit protein processing has been demonstrated in three separate in vitro assays. The ability of the compounds of the invention to inhibit ras-related cancer growth has been demonstrated in an in vitro assay and two separate in vivo experiments. The compounds of the invention are effective inhibitors of ras-related cancers.

As Inhibition of FTase and GGTase Prenylation

The ability of the disclosed inhibitor compounds to inhibit FTase was measured according to a published prenylation assay (Moores et al., *J. Biol. Chem.* 266:14603 (1991). Partially purified FTase with 3 $\mu$M recombinant H-ras and 440 nM [$^3$H]FPP (FTase) were used. The inhibitors were diluted in assay buffer, and each assay mixture was incubated 15 min. at 37° C. Where inhibition of GGTase was measured, partially purified GTTase with 5 $\mu$M recombinant H-ras (61L, CAIL) and 1 $\mu$M [$^3$H] geranylgeranyl diphosphate were used.

The $IC_{50}$ (concentration of compound needed to cause 50% inhibition) values are presented in Table 1. Nanomolar concentrations of the indicated compounds were sufficient to inhibit farnesylation of ras proteins in vitro. For screening candidate compounds useful for the treatment of ras-associated tumors, the FTase assay is preferred. One embodiment of the invention selectively inhibits FTase. Substitutions which confer GGTase specificity as taught herein also produced potent inhibitors of GGTase.

TABLE 1

| Compound | $IC_{50}$ $\mu$M FTase | $IC_{50}$ $\mu$M GGTase |
|---|---|---|
| PA011 | 0.140 | 11.0 |
| PA021 | 0.028 | 7.1 |
| PA031 | 0.0036 | 0.215 |
| PA041 | 0.0025 | 0.056 |
| PA051 | 0.020 | 0.076 |
| PA061 | 0.0021 | 0.048 |
| PA071 | 0.022 | 0.5 |
| PA081 | 0.102 | 2.66 |
| PA091 | 0.170 | 2.38 |
| PA101 | 0.170 | 1.30 |
| PA111 | 0.013 | 0.27 |
| PA121 | 0.015 | 0.38 |
| PA131 | 0.028 | 1.8 |
| PA141 | 0.095 | 0.880 |
| PD012 | 0.038 | 0.62 |
| PD022 | 0.0052 | 3.065 |
| PD032 | 0.45 | 2.86 |
| PD042 | 0.005 | 1.62 |
| PD052 | 2.81 | 8.05 |
| PD062 | 0.2 | 1.76 |
| PD072 | 0.042 | 0.68 |
| PD082 | 1.57 | >10 |
| PD092 | 0.052 | 3.2 |
| PD102 | 0.394 | >10 |
| PD112 | 2.22 | 8.05 |
| PD122 | 0.003 | 0.010 |
| PD132 | 0.245 | 4.77 |
| PD142 | 0.042 | 2.12 |
| PD152 | 0.023 (12) | 0.044 (5) |
| PD162 | 0.26 | 4.57 |
| PD172 | 0.007 | 0.75 |
| PD182 | <0.001 | 0.0633 (4) |
| PD192 | 0.296 | 2.99 |
| PD202 | 0.017 | 1.12 (3) |
| PD212 | 0.003 | 0.0045 |
| PD222 | 0.71 | 3.04 |
| PD301 | 0.002 | 0.0037 |
| PD311 | 0.069 (6) | 0.57 |
| PD321 | 0.025 | 0.014 |
| PD331 | 0.011 (22) | 0.013 (11) |
| PD341 | 0.0002 | 0.0076 |
| PD351 | 0.32 | 2.49 |
| PD361 | 0.0001 | 0.016 |
| PD371 | 0.038 | 0.112 |
| PD381 | 0.080 | 0.0710 |
| PD391 | 0.0290 | 0.0550 |
| PD401 | 0.028 | 1.40 |
| PD411 | 0.56 | 8.4 |
| PD421 | 0.57 | 3.4 |
| PD431 | 0.006 | 1.08 |
| PD441 | 0.026 | 0.17 |
| PD451 | 0.146 | 1.11 |
| PE011 | 0.043 | 1.030 |
| PE021 | 0.009 | 0.092 |
| PE031 | 0.020 | 0.14 |
| PE041 | 0.027 | 0.160 |
| PE051 | 0.29 | 2.30 |
| PE061 | 0.060 | 6.30 |
| PM011 | 1.13 | 1.6 |
| PM012 | 0.002 | 0.520 |
| PM021 | 0.017 | 0.075 |
| PM022 | 0.018 | 0.130 |
| PM031 | 0.115 | 1.40 |
| PM032 | 0.093 | 6.59 |
| PM041 | 0.18 | 1.4 |
| PM042 | 3.1 | 0.32 |
| PM051 | 0.00085 | 1.55 |
| PM052 | 0.0003 | 0.19 |
| PM061 | 0.007 (12) | 0.144 (3) |

TABLE 1-continued

| Compound | IC$_{50}$ μM FTase | GGTase |
|---|---|---|
| PM062 | 0.009 | 0.42 |
| PM071 | 0.71 | 0.95 |
| PM072 | 0.16 | 3.96 |
| PM081 | 0.17 | 1.68 |
| PM082 | 0.03 | 0.148 |
| PM091 | 0.002 | >1.0 |
| PM092 | 0.215 | 3.50 |
| PM101 | 0.024 (8) | 0.793 (3) |
| PM102 | 0.29 | 4.85 |
| PM111 | 0.024 | 0.246 |
| PM112 | 0.0012 | 1.66 |
| PM121 | 0.022 | 1.72 |
| PM122 | 0.003 | 2.2 |
| PM131 | 0.605 | 0.0024 |
| PM132 | 0.119 | 1.63 |
| PM141 | 0.0001 | 0.016 |
| PM142 | 0.008 | 0.072 |
| PM151 | 0.605 | 3.87 |
| PM152 | 0.038 | 0.270 |
| PM161 | 0.0009 | 2.14 |
| PM162 | 0.0018 | 0.12 |
| PM172 | 0.056 | 0.123 |
| PM182 | 0.017 | 0.52 |
| PM192 | 0.280 | 3.79 |
| PM202 | 0.016 (2) | 7.42 (2) |
| PM212 | 0.056 | 1.84 |
| PT011 | 0.043 | 0.638 |

B. Inhibition of Prenylation in Whole Cells

The ability of compounds of the invention to inhibit H-ras farnesylation and rap1 geranylgeranylation in whole cells was determined. H-ras (61L) transformed NIH3T3 fibroblasts were generously provided by C. Der, Univ. N. Carolina. These fibroblasts were treated for 24 h with 50 μM lovastatin (control) or the indicated concentrations of inhibitor. The cells were lysed in 1% NP-40, 5 mM Tris-HCl (pH 8.0), 5 mM EDTA, 0.1 mM N-tosyl-L-phenylalanine chloromethyl ketone, 0.1 mM N-tosyl-L-lysine chloromethyl ketone, and 1 mM phenylmethylsulfonyl fluoride. The lysate was centrifuged (15000×g, 5 min.) and the supernatant was used as a cell extract. Total protein was separated by SDS-PAGE in 15% acrylamide gel. After transfer to IMMO-BILON P™ membrane (Millipore), the blots were probed with LA069 mouse monoclonal antibody to H-ras (Quality Biotech), or rabbit polyclonal antibody to rap1/Krev (Santa Cruz Biotechnology). All Western blots were developed using ECL chemiluminescent reagents (Amersham).

The IC$_{50}$ values for H-ras are presented in Table 2. Sub-micromolar concentrations of the indicated compounds are sufficient to inhibit farnesylation of ras proteins in whole cells. In contrast, inhibition of geranylgeranylation of rap1 required compound concentrations in excess of 100 μM (data not shown). Thus, many compounds of the invention inhibit farnesylation more specifically than geranylgeranylation.

TABLE 2

| Analog | H-ras IC$_{50}$ μM |
|---|---|
| PA011 | 0.1 |
| PA021 | 0.08 |
| PA031 | 1.0 |
| PA041 | 3.5 |
| PA051 | 1.9 |

TABLE 2-continued

| Analog | H-ras IC$_{50}$ μM |
|---|---|
| PA061 | 0.58 |
| PA071 | 3.1 |
| PA081 | 0.025 |
| PA091 | 0.1 |
| PA101 | 0.24 |
| PA111 | 0.13 |
| PA121 | 0.58 |
| PA131 | 0.039 |
| PA141 | 0.017 |
| PD012 | 72 |
| PD022 | 0.4 |
| PD032 | 1.95 |
| PD042 | 1.95 |
| PD062 | 21 |
| PD072 | 7.4 |
| PD092 | 0.78 |
| PD102 | 75 |
| PD112 | 193 |
| Pd122 | 0.4 |
| PD132 | 2.6 |
| PD142 | 7.3 |
| PD152 | 0.32 |
| PD162 | 326 |
| PD172 | 13.1 |
| PD182 | 2.8 |
| PD192 | 0.18 |
| PD202 | 1.95 |
| PD212 | 0.11 |
| PD222 | >50 |
| PD301 | 4.5 |
| PD311 | 0.1–1 |
| PD321 | 0.1–1 |
| PD331 | 0.4 |
| PD341 | 0.29 |
| PD351 | 3.3 |
| PD361 | 3.5 |
| PD371 | 0.09 |
| PD381 | –1 |
| PD391 | 16.4 |
| PD401 | 0.1–1 |
| PD411 | 0.22 |
| PD421 | 1.90 |
| PD441 | 4.2 |
| Pd451 | 0.4 |
| PE011 | 0.01 |
| PE021 | 0.28 |
| PE031 | 0.33 |
| PE041 | 0.19 |
| PE051 | 0.11 |
| PE061 | 1.1 |
| PM011 | >100 |
| PM012 | 2.7 |
| PM021 | 2.1 |
| PM022 | 13.1 |
| PM031 | 25 |
| PM032 | 19.5 |
| PM041 | 2.3 |
| PM042 | >500 |
| PM051 | 23.5 |
| PM052 | 2.6 |
| PM061 | 4.8 |
| PM062 | 0.36 |
| PM071 | >100 |
| PM072 | 2.4 |
| PM081 | 23.4 |
| PM082 | 21 |
| PM091 | 474 |
| PM092 | 2.7 |
| PM101 | 14.6 |
| PM102 | 26 |
| PM111 | >100 |
| PM112 | 4.0 |
| PM121 | 23.4 |
| PM122 | 23.4 |
| PM131 | >250 |
| PM132 | 1.6 |
| PM141 | 9.7 |

TABLE 2-continued

| Analog | H-ras IC$_{50}$ μM |
|---|---|
| PM142 | 1.1 |
| PM151 | 2.9 |
| PM152 | 40.3 |
| PM161 | 18.9 |
| PM162 | 13.1 |
| PM172 | >100 |
| PM182 | 2.7 |
| PM192 | 0.23 |
| PM202 | 1.2 |
| PM212 | 0.045 |
| PT011 | 0.023 |

C. Inhibition of Anchoraae-Independent Tumor Cell Growth

Five tumor cell lines were seeded at 600 cells/well (12-well plates) in 0.6 mL of 0.3% Noble agar in culture medium over a bottom agar layer (0.5% Noble agar in culture medium). The culture medium was Dulbecco's modified Eagle's medium (Nissui Pharmaceutical Co., Ltd., Tokyo, Japan), supplemented with 10% heat-inactivated calf serum (GIBCO, Grand Island, N.Y.). A 10 mM stock solution of inhibitor compound PD331 in DMSO was diluted with culture medium to 3x the final concentration and 0.6 mL of the diluted inhibitor solution was overlayed on each well. Controls contained the same amount of DMSO as inhibitor samples. Plates were incubated at 37° C. in 5% $CO_2$ for 14 days. Colonies were counted by replacement of the overlaying medium with 0.6 mL of 2 mg/mL MTT in PBS, incubation for 30 min, and quantitation of scanned photographs. IC$_{50}$ concentrations for each cell line are shown below in Table 3.

TABLE 3

| Cell Line | IC$_{50}$ (μM) |
|---|---|
| HT1080 | 1.8 |
| MIApaca-2 | 19 |
| Sw620 | 22 |
| T24 | 0.3 |
| zH1 | 0.6 |

D. Inhibition of Human Tumor Xenoaraft in Mice

H-ras (61L) transformed NIH3T3 fibroblasts were grown in Dulbecco's modified Eagle's medium supplemented with 10% heat-inactivated calf serum. 100 U/mL penicillin, 100 μg/mL streptomycin, and 0.75 mg/mL G418 (GIBCO) and incubated at 37° C. in 5% $CO_2$. Cells were harvested from exponential-phase maintenance cultures (T-225 cm$^2$ culture flasks, Corning Inc., Corning, N.Y.) with trypsin-EDTA (GIBCO), centrifuged at 160 xg for 5 min, washed once with 10 mL cold Hank's balanced salt solution (HBSS, GIBCO), and resuspended at a concentration of 1×10$^6$ cells/mL.

Five week old female athymic nude mice were obtained from SLC (3371-8, Kotoummachi, Hamamatsu-shi, Shizuoka 431-11, Japan) and maintained under pathogen-free conditions. The mice were subcutaneously injected in the lateral flank with 1×10$^5$ H-ras transformed cells/mouse.

Inhibitor compound PD331 was suspended in saline containing 2% Tween-80 in a total injection volume of 0.2 mL. Two dosage concentrations were prepared, 0.3 mg/mouse or 1.0 mg/mouse. Compound PD331 was subcutaneously injected daily at the site of tumor cell implantation for 5 consecutive days, starting approximately 8 h after the implantation (day 0). The control group was injected with vehicle only. Body weight and tumor dimensions were measured at days 7, 10, and 14. Tumor volume was estimated by the following calculation: tumor volume =(0.5)(length×width×width). At day 14, each mouse was euthanized with $CO_2(g)$, and each tumor was excised and weighed. The statistical significance was estimated by the Student's T-test. Final tumor volumes are presented in Table 4.

TABLE 4

| Sample | Dosage | Tumor volume (μl) | T/C (%) Volume |
|---|---|---|---|
| Control | vehicle | 1634.40 ± 527.93 | 100 |
| PD331 | 0.3 mg/mouse | 871.28 ± 526.90 | 53.3 |
| PD331 | 1.0 mg/mouse | 269.55 ± 292.95 | 16.5 |

Compound PD331 has a significant effect on H-ras tumor growth in mice. At every concentration, both the weight and the volume of the tumors from the treated group were less than the weight and volume of tumors from the control group. These data clearly demonstrate that the compounds of the invention inhibit the formation and growth of in vivo tumors caused by the ras oncogene.

E. Inhibition of Human Tumor Xenoaraft in Mice

The same in vivo experiment as Example D above was performed, using compound PM061. Instead of 0.3 mg/mouse and 1.0 mg/mouse, three injection concentrations were prepared (0.5 mg/mouse, 1.0 mg/mouse, and 2.0 mg/mouse). Body weight and tumor size were measured at days 7, 10, and 15. Tumors were excised at day 15. Final tumor volumes are presented in Table 5.

Compound PM061 had a significant effect on H-ras tumor growth in mice. An injection of 2.0 mg of compound PM061 decreased the tumor volume to 53.2% of the tumor volume in the control mouse. These data clearly demonstrate that the compounds of the invention inhibit the formation and growth of in vivo tumors caused by the ras oncogene.

| Sample | Dosage | Tumor Volume (μl) | T/C (%) Volume |
|---|---|---|---|
| Control | vehicle | 2613.6 ± 462.8 | 100 |
| PM061 | 0.5 mg/mouse | 2360.4 ± 645.0 | 90.3 |
| PM061 | 1.0 mg/mouse | 2660.3 ± 756.4 | 101.8 |
| PM061 | 2.0 mg/mouse | 1400.6 ± 703.2 | 53.6 |

F. Use

The disclosed compounds are used to treat ras-associated tumors in mammals, and particularly humans. The disclosed compounds are also used to treat tumors or other conditions mediated by (i) a farnesylated protein, such as ras, lamin B, or γ-transducin, (ii) a geranylgeranylated protein, such as Rap, Rab, or Rho, or (iii) a combination thereof.

The claimed pharmaceutically acceptable salts may be formed, for example, with 1, 2, 3, or more equivalents of hydrogen chloride, hydrogen bromide, trifluoroacetic acid, and others known to those in the art of drug formulation. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-cancer agents. Another aspect of the invention is a packaged drug, containing a pharmaceutical composition formulated into individual dosages and printed instructions for self-administration.

Compounds of the invention may be prepared for use in parenteral administration, particularly in the form of solutions or liquid suspensions; for oral administrations, particularly in the form of tablets or capsules; or intranasally, particularly in the form of powders, gels, oily solutions, nasal drops, aerosols, or mists. A compound of the invention may be administered in unit dosage form, and may be prepared by any of the methods well known in the pharmaceutical art, for example, as described in *Remington's Pharmaceutical Sciences* (Mack Pub. Co., Easton, Pa., 1980).

Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene. Additional parental delivery systems include ethylene-vinyl acetate copolymer particles, osmotic pumps, implantable infusion systems, and liposomes.

Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 0.1 to 10% w/v of compound for parenteral administration. Typical dose ranges are from about 0.1 to about 250 mg/kg of body weight per day, given in 2–4 divided doses. Each divided dose may contain the same or different compounds of the invention. The dosage will be an effective amount depending on several factors including the type and extent of cancer metastasis, the overall health of a patient, and the formulation and route of administration of the selected compound(s).

Without further elaboration, it is believed that one skilled in the art can, based on the description herein, utilize the present invention to its fullest extent. The following specific examples are, therefore, to be construed merely as illustrative, and not limitative of the remainder of the disclosure in any way whatsoever. Publications mentioned herein are hereby incorporated by reference.

Example 1
Synthesis of Alcohols R003D

A 1.0 M solution of DIBAL in hexanes (87 mL, 87 mmol) was added dropwise to a solution of amide R001D (17.7 g, 34.9 mmol, prepared from condensation of N-BOC, S-trityl cysteine and N,O-dimethyl hydroxylamine hydrochloride using hydroxybenzotriazole hydrate [HOBT], dicyclohexylcarbodiimide [DCC], and N-methylmorpholine [NMM] in dimethylformamide [DMF]) in anhydrous toluene (230 mL). The reaction mixture was stirred at −78° C. for 30 min, quenched with methanol (80 mL), and then allowed to warm to room temp. Saturated aqueous sodium potassium tartrate (100 mL) was added and the resulting two-phase mixture stirred rapidly at room temp for 45 min. CELITE® was added, the mixture was filtered through a pad of CELITE®, and the filter pad then was washed well with ethyl acetate. The aqueous phase was extracted with ethyl acetate. The combined organic phases were dried with brine, dried over $MgSO_4$, filtered, concentrated, and azeotroped two times with anhydrous toluene (15 mL) to afford the protected cysteine aldehyde.

To a solution of E-4-tertbutyldimethylsilyloxy-tri-n-butylstannylpropene (65.0 g, 14.09 mmol) in anhydrous tetrahydrofuran (THF) (230ml) at −78° C. was added a 2.5 M solution of n-butyllithium in hexanes (58.6 mL, 146.5 mmol) dropwise. After the addition was complete, the reaction mixture was stirred an additional 1 h at −78° C. to complete transmetalation to lithiated olefin R002D. A solution of the protected cysteine aldehyde, described above, in anhydrous THF (50 mL, precooled to −78° C.) was added to olefin R002D by cannula. The orange-red reaction mixture was allowed to stir for an additional 15 min. after completion of the addition. The solution then was quenched by addition of saturated aqueous $NH_4Cl$ (60 mL), and allowed to warm to room temp. After extraction with ethyl acetate, the organic phases were dried with brine, dried over $MgSO_4$, filtered, and concentrated to a yellow liquid (~90 g). The crude product was partially purified by chromatography on silica, eluting with a (10–30%) ethyl acetate-hexanes gradient to afford the alcohols R003D (9.53 g, 44%). The following characteristic values may be obtained by nuclear magnetic resonance spectroscopy:

$^1$H NMR (CDCl$_3$) δ: 7.1–7.5 m, 5.72 m, 5.53 dd (one isomer, J=6.1, 14.3 Hz), 5.45 dd (J=6.1, 14.3 Hz), 4.11 dd (J=6.4, 7.9 Hz), 1.43 s (one isomer), 1.40 s (one isomer), 0.89 s, 0.04 s.

Example 2
Synthesis of Oxazolidinones R004D

Alcohols R003D (11.7 g, 18.9 mmol) were added to a suspension of hexane washed NaH (1.03 g, 42.8 mmol) in anhydrous THF (100 mL) by cannula, and the resulting mixture was stirred overnight. The reaction was quenched with saturated aqueous $NH_4Cl$ and diluted with both water and ethyl acetate. After separation of the phases, the organic phase was washed with phosphate buffer (pH 7.2). The combined aqueous phases were extracted with ethyl acetate. The combined organic phases were dried once with brine, dried over $Na_2SO_4$, filtered, and then concentrated to a dark foam (10.51 g). The dark foam was purified by flash chromatography on silica gel (FC), eluting with 25% ethyl acetate-hexanes. Oxazolidinones R004D (6.59 g, 64%) were obtained as a yellow foam. The following characteristic values may be obtained by nuclear magnetic resonance spectroscopy:

$^1$H NMR (CDCl$_3$) δ: 7.1–7.5 m, 5.85 dt (one isomer, J=4.7, 14.8 Hz), 5.77 (one isomer, J=4.7, 14.8 Hz), 5.55 m, 4.84 t (one isomer, J=7.3 Hz), 4.43 t (one isomer, J=6.2 Hz), 4.16 m, 3.08 q (one isomer, J=7.5 Hz), 2.96 q (one isomer, J=4.7 Hz), 0.91 s (one isomer), 0.89 s (one isomer), 0.07 s, 0.04 s.

Example 3
Synthesis of Oxazolidinone R005D

Di-t-butyldicarbonate (3.95 g, 18.1 mmol) was added to a solution of oxazolidinone R004D (6.59 g, 12.1 mmol) and DMAP (300.4 mg, 1.46 mmol) in anhydrous THF (100 mL) that was maintained at 0° C. After 15 min, the reaction mixture was allowed to warm to room temp and stirred for an additional 45 min. After dilution with ethyl acetate and water, the phases were separated, and the aqueous phase was extracted with ethyl acetate. The combined organic phases were dried with brine, dried over $Na_2SO_4$, filtered, and concentrated to a yellow oil. The mixture of oxazolidinones was purified and separated by FC, eluting with 15% ethyl acetate-hexanes to afford first the a alkoxy isomer (2.30 g, 36%) followed by the desired oxazolidinone R005D (3.71 g, 47%). The following characteristic values may be obtained by nuclear magnetic resonance spectroscopy:

$^1$H NMR (CDCl$_3$) δ: 7.1–7.4 m, 5.91 dt (J=15.4, 3.9 Hz), 5.81 ddt (J=6.8, 15.5, 3.5 Hz), 4.29 m, 4.19 m, 2.53 dd (J =7.5, 12.1 Hz), 2.22 dd (J=3.7, 12.2), 1.48 s, 0.88 s, 0.44 s.

Example 4
Synthesis of Olefin R006D

To a slurry of CuCN (2.06, 23.0 mmol) in anhydrous THF (75 mL) at −40° C. was added a 2M solution of i-PrMgCl in THF (11.50 mL, 23.0 mmol). The reaction mixture was stirred at −40° C. for 10 min and then at 0° C. for 20 min. The resulting black mixture was cooled to −78° C. and $BF_3 \cdot OEt_2$ (2.80 mL, 22.8 mmol), added dropwise. After stirring for 5 min, a solution of oxazolidinone R005D (3.71 g, 5.74 mmol) in anhydrous THF (25 mL) was added by cannula, and the resulting mixture was stirred for 1 h at −78° C. A mixture of a saturated aqueous solution of $NH_4Cl$ (70 mL) and $NH_4OH$ (35 mL) was added by cannula, and the reaction mixture was allowed to warm to room temp. Ethyl acetate was added, and the biphasic mixture was stirred vigorously for 15 min then extracted with ethyl acetate. The organic phase was washed with water, phosphate buffer (pH 7.2), and the combined aqueous phases were back-extracted with ethyl acetate. The combined organic phases were dried with brine, dried over $Na_2O_4$, filtered, and concentrated to a yellow oil. The crude product was purified by FC, eluting with 10% ethyl acetate-hexanes to afford the desired olefin R006D as yellow foam (2.64 g, 71%). The following characteristic values may be obtained by nuclear magnetic resonance spectroscopy:

$^1$H NMR ($CDCl_3$) δ: 7.42 d (J=8.0 Hz), 7.29 t (J=7.3 Hz), 7.22 t (J=7.2 Hz), 5.39 dd (J=8.7, 15.2 Hz), 5.27 dd (J=5.9, 15.4 Hz), 4.57 bs, 4.18 bs, 3.54 ab q, 2.38 bm, 2.33 bm, 1.92 m. 1.79 octet (J~7 Hz), 1.43 s, 0.87 S, 0.80 d (J=6.8 Hz), 0.01 s.

Example 5
Synthesis of Alcohol R007D

A solution of silyl ether R006D (2.64 g, 4.09 mmol) and tetrabutylammonium fluoride (TBAF) (2.69 g, 10.28 mmol) in anhydrous THF (40 mL) was stirred for 5 h at room temp. The reaction mixture was diluted with ethyl acetate and washed with pH 7.2 phosphate buffer. The organic layer was dried with brine, dried over $Na_2SO_4$, filtered, and concentrated to afford a dark oil. The crude product was purified by FC, eluting with 25% ethyl acetate-hexanes to afford the desired alcohol R007D as a yellow oil (2.24 g, >100%). The following characteristic values may be obtained by nuclear magnetic resonance spectroscopy:

$^1$H NMR ($CDCl_3$) δ: 7.41 d (J=7.0 Hz), 7.28 t (J=7.5 Hz), 7.21 t (J=6.5 Hz), 5.33 dd (J=5.5, 15.2 Hz), 5.27 dd (J=8.2, 15.5 Hz), 4.60 bs, 4.10 bs, 3.63 dd (J=4.6, 10.8 Hz), 3.34 dd (J=9.10, 10.5 Hz), 2.43 bm, 2.27 bm, 1.93 m. 1.60 octet (J~7 Hz), 1.41 s, 0.87 d (J=6.8 Hz), 0.85 d (J=6.8 Hz).

Example 6
Synthesis of Aldehyde R008D

A solution of alcohol R007D (2.24 g, 4.09 mmol) and PCC (1.754 g, 8.14 mmol) was stirred in $CH_2Cl_2$ (40 mL) at room temp for 4 h. Solvent was removed under vacuum, and the residual material was slurried in $CH_2Cl_2$-methanol. This slurry was pipetted into a rapidly stirring suspension of CELITE® in ether, and the mixture was filtered. The filtrate was concentrated, and the residue was precipitated as before, but without the use of methanol. After filtration and concentration, a yellow-green oil was obtained which was promptly purified by FC, eluting with 15% ethyl acetate-hexanes. The aldehyde R008D (2.39 g, >100%) was obtained as a pale yellow oil. The following characteristic values may be obtained by nuclear magnetic resonance spectroscopy:

$^1$H NMR ($CDCl_3$) δ: 7.41 d (J=7.0 Hz), 7.28 t (J=7.5 Hz), 7.21 t (J=6.5 Hz), 5.33 dd (J=5.5, 15.2 Hz), 5.27 dd (J=8.2, 15.5 Hz), 4.60 bs, 4.10 bs, 3.63 dd (J=4.6, 10.8 Hz), 3.34 dd (J=9.10, 10.5 Hz), 2.43 bm, 2.27 bm, 1.93 m, 1.60 octet (J~7 Hz), 1.41 s, 0.87 d (J=6.8 Hz), 0.85 d (J=6.8Hz).

Example 7
Synthesis of Alcohols R009D

Aldehyde R008D (2.39 g, <4.09 mmol) and methyl E-3-iodo-acrylate were placed in a flask, flushed with argon, capped, and transferred to a dry box. Anhydrous freshly distilled THF (20 mL) was added, followed by slow, portionwise addition of 0.5% $NiCl_2$:$CrCl_2$ (1.52 g, 12.4 miol). After 4 h, the dark mixture was removed from the dry box and diluted with saturated aqueous $NH_4Cl$ and $CHCl_3$. The resulting slurry was stirred rapidly overnight. After separation of the phases, the organic phase was washed once with water and once with phosphate buffer (pH 7.2) which resulted in an emulsion. After removal of the emulsion by filtration through CELITE® and clean separation of the resulting two phases, the organic phase was dried once with brine, dried over $Na_2SO_4$, filtered, and concentrated to a yellow-green semisolid. Repeated purification by FC, eluting with 15% ethyl acetate-hexanes afforded the desired alcohols R009D as colorless oils (524 mg, 21% overall from R006D). The following characteristic values may be obtained by nuclear magnetic resonance spectroscopy:

$^1$H NMR ($CDCl_3$) δ isomer I: 7.40 d (J=7.5 Hz), 7.29 t (J=7.5 Hz), 7.21 t (J=7.3 Hz), 6.98 dd (J=4.4, 15.6 Hz), 6.02 dd (J=1.7, 15.6 Hz), 5.32 dd (J=6.1, 15.2 Hz), 5.16 dd (J=10.1, 15.3 Hz), 4.58 bs, 4.34 bs, 4.02 bs, 3.70 s, 2.46 dd (J=5.5, 11.5 Hz), 2.34 bd (J=9.7 Hz), 2.20 bs, 1.98 dt (J=4.8, 15.2 Hz), 1.68 bm, 1.40 s, 0.96 d (J=6.6 Hz), 0.84 d (J=6.6 Hz).

Example 8
Synthesis of Mesylates R010D

A solution of $Et_3N$ (246 µL, 1.77 mmol) was added to a solution of alcohol R009D (229.6 mg, 0.37 mmol) in anhydrous $CH_2Cl_2$ (7.5 mL) at 0° C. under $N_2$. A solution of methanesulfonyl chloride (129 µL, 1.68 mmol) then was added to the mixture, and the reaction was allowed to warm to room temp. After dilution with ethyl acetate (25 mL) and saturated aqueous $NH_4Cl$, the organic phase was separated, dried with brine, dried over $MgSO_4$, filtered, and concentrated to a yellow oil. This oil was purified by FC, eluting with a 15–25% ethyl acetate-hexanes gradient. Mesylates R010D (252 mg, 98%) were obtained as a colorless oil. The following characteristic values may be obtained by nuclear magnetic resonance spectroscopy:

$^1$H NMR ($CDCl_3$) δ: 7.39 d (J=7.2 Hz), 7.28 t (J=7.4 Hz), 7.21 t (J=6.7 Hz), 6.80 dd (J=6.4, 15.7 Hz), 6.06 bd (J=15.6 Hz), 5.31 dd (J=6.1, 15.2 Hz), 5.21 b, 4.58 bs, 4.11 q (J=7.0 Hz), 3.68 s, 2.90 s, 2.43 bs, 2.22 bm, 1.82 m, 1.40 s, 0.92 d (J=6.5 Hz), 0.85 d (J=6.5 Hz).

Example 9
Synthesis of Diene R011D

A 2M solution of benzyl magnesium chloride (335 µL, 2.72 mmol) in THF was added dropwise to a suspension of CUCN (256.5 mg, 2.86 mmol) in anhydrous THF (7.5 mL) maintained at −40° C. under Argon. The reaction mixture was stirred for 20 min at −40° C., and then warmed to 0° C. for 20 min. The resulting dark, opaque mixture was cooled to −78° C. and $BF_3 \cdot OEt_2$ (335 µL, 2.72 mmol) was added dropwise. After 5 min, a solution of mesylates R010D (186.1 mg, 0.27 mmol) in anhydrous THF (2 mL+2 mL rinse) was added. After 15 min, the reaction was quenched with saturated aqueous $NH_4Cl$ and $NH_4OH$ (1:1 v/v) and allowed to warm to room temp. It then was diluted with ethyl acetate, stirred vigorously for 15 min, diluted further with both ethyl acetate and water, and the phases were separated in a separatory funnel. The organic phase was washed with pH 7.2 phosphate buffer. The aqueous phase was back extracted with ethyl acetate, and the combined organic phases were dried with brine, dried over $MgSO_4$, filtered, and concentrated to a yellow oil. After purification by FC, eluting with 10% ethyl acetate-hexanes, a mixture of the benzyl isomers of diene R001D (157.7 mg, 85%) was obtained. The isomers were separated after further purification by HPLC on silica, eluting with 5% ethyl acetate-hexanes to afford pure major β isomer R001D (~80 mg, 43%) as well the minor α isomer (43 mg, 23%). The following characteristic values may be obtained by nuclear magnetic resonance spectroscopy:

$^1$H NMR ($CDCl_3$) δ major isomer: 7.09–7.40 m, 5.46 t (J=10.4 Hz), 5.35 t (J=10.5 Hz), 5.27 ddd (J=1.2, 7.5, 15.4 Hz), 4.91 dd (J=5.0, 15.2 Hz), 4.47 bs, 4.09 bs, 3.60 s, 3.55 q (J=8.3 Hz), 3.00 dd (J=7.5, 13.5 Hz), 2.75 dd (J=7.4, 13.5 Hz), 2.64 q (J=8.1 Hz), 2.29 bm, 2.25 bm, 1.52 o (J=7.5 Hz), 1.42 s, 0.81 d (J=6.7 Hz), 0.78 d (J=6.7 Hz).

$^1$H NMR ($CDCl_3$) δ minor isomer: 7.04–7.43 m, 5.34 m, 4.97 ddd (J=0.6, 6.3, 15.3 Hz), 4.51 bs, 4.12 bs, 3.61 s, 3.28 q (J=7.8 Hz), 3.07 dd (J=7.2, 13.6 Hz), 2.76 dd (J=8.0, 13.6 Hz), 2.39 q (J=6.9 Hz), 2.34 bm, 2.29 bm, 1.54 o (J=6.6 Hz), 1.44 s, 0.75 d (J=6.7 Hz).

Example 10
Synthesis of Acid R012D

A solution of LiOH (11.5 mg, 480 gmol) in water (5.0 mL) was added to a solution of methyl ester R011D (110 mg, 160 μmol) in dioxane (5.0 mL), and the reaction was stirred for 12 h at room temp under $N_2$. Additional LiOH (11.5 mg, 480 μmol) then was added, and the reaction was stirred for an additional 3 h. The reaction was acidified to pH 2 with 1M $KHSO_4$, and then extracted with ethyl acetate. The combined organic phases were washed with brine, dried over $Na_2SO_4$, filtered, and then concentrated to acid R012D (85 mg, 79%) which was obtained as a clear oil. The following characteristic values may be obtained by nuclear magnetic resonance spectroscopy:

$^1$H NMR ($CD_3OD$) δ: 6.97–7.37 m, 6.53 m, 5.45 t (J=10.4 Hz), 5.33 t (J=10.4 Hz), 5.24 dd (J=7.8, 15.7 Hz), 4.94 dd (J=6.9, 15.3 Hz), 3.86 bs, 3.48 bm, 2.91 dd (J=7.9, 13.4 Hz), 2.67 dd (J=6.8, 13.4 Hz), 2.64 m, 2.33 q (J=10.5 Hz), 2.10 dd (J=5.9, 12.1 Hz), 1.5 m, 1.41 s, 0.82 d (J=6.0 Hz), 0.80 d (J=6.5 Hz).

Example 11
Synthesis of Amide R013D

Acid R012D (127.3 mg, 190 μmol), p-nitrobenzyl methionine hydrochloride (obtained by HCl deprotection of 110 mg of N-BOC p-nitrobenzyl methionine, 290 μmol), HOBT (31.3 mg, 230 μmol), DCC (83.5 mg, 400 μmol), and NMM (25 μL, 230 μmol) were dissolved in anhydrous DMF (2.0 mL) and then stirred at room temp overnight. The reaction mixture was filtered, and the solid residue was washed well with ethyl acetate. The combined filtrates then were washed with water and phosphate buffer (pH 7.2). The aqueous phases were extracted with ethyl acetate, and the combined organic phases were dried once with brine, dried over $MgSO_4$, and concentrated to a yellow oil. Purification of the crude amide by FC, eluting with a 20–25% ethyl acetate-hexanes gradient, afforded amide R013D (165.8 mg, 93%) as a colorless foam. The following characteristic values may be obtained by nuclear magnetic resonance spectroscopy:

$^1$H NMR ($CDCl_3$) δ: 8.22 d (J=8.7 Hz), 7.48 d (J=8.7 Hz), 7.08–7.39 m, 6.15 bd, 5.55 t (J=10.5 Hz), 5.41 t (J=10.3 Hz), 5.31 dd (J=7.0, 15.3 Hz), 5.22 ab quartet, 4.98 dd (J=5.8, 15.4 Hz), 4.83 d (J=5.7 Hz), 4.68 m, 4.52 bm, 4.09 bs, 3.33 q (J=8.1 Hz), 3.06 dd (J=7.9, 13.4 Hz), 2.70 dd (J=6.7, 13.4 Hz), 2.59 m, 1.98 s, 1.42 s, 0.81 d (J=6.7 Hz), 0.78 d (J=6.7 Hz).

Example 12
Synthesis of Acid R014D

To a solution of p-nitrobenzyl ester R013D (88.8 mg, 98.9 μmol) in THF (1.5 mL) was added a solution of $Na_2S \cdot 9 H_2O$ (126 mg, 0.52 mmol) in water (0.5 mL). The reaction mixture was stirred at room temp under $N_2$ for 2 h, whereupon it was quenched by addition of TFA (440 μL, 5.71 mmol). Solvents were removed under reduced pressure, and the residue was dissolved in methanol. Undissolved solid was removed by filtration, and the filtrate was purified by HPLC on C18 reverse phase columns, eluting with a gradient of 0.15% TFA in 5% acetonitrile-water to 0.15% TFA in acetonitrile. Acid R014D (48.8mg, 69%) was obtained as a colorless oil. The following characteristic values may be obtained by nuclear magnetic resonance spectroscopy:

$^1$H NMR ($CD_3OD$) δ: 7.09–7.39 m, 5.55 t, (J=10.4 Hz), 5.34 t (J=10.5 Hz), 5.20 dd (J=6.8, 15.3 Hz), 4.93 m, 4.40 dd (J=3.9, 9.4 Hz), 3.89 bs, 3.52 q (J=8.2 Hz), 2.82 dd (J=10.1, 12.8 Hz), 2.64 dd (J=5.4, 13.3 Hz), 2.40 dd (J=7.6, 11.8 Hz), 2.14 dd (J=6.0, 12.2 Hz), 1.96 s, 1.66 m, 1.52 m, 085 d (J=7.2 Hz), 0.83 d (J=7.0 Hz).

Example 13
Synthesis of PD331

TFA (~3 mL) was added to a slurry of acid R014D (48.8 mg, 88.2 μmol) in $Et_3SiH$ (1 mL) at room temp, and the solution was stirred for 5 min. PD331 (27 mg, 68%) was obtained as a white solid after removal of solvents, purification of the residue by HPLC on C18 reverse phase columns (the elution gradient was 0.15% TFA in 5% acetonitrile-water to 0.15% TFA in acetonitrile), and lyophilization from acetonitrile-water. The following characteristic values may be obtained by nuclear magnetic resonance spectroscopy:

$^1$H NMR ($CD_3OD$) δ: 8.13 d (J=8.3 Hz), 7.15–7.28 m, 5.79 dd (J=7.9, 15.7 Hz), 5.64 t (J=10.4 Hz), 5.42 t (J=10.5 Hz), 5.37 dd (J=8.0, 15.2 Hz), 4.45 m, 3.80 q (J=6.6 Hz), 3.59 q (J=8.3 Hz), 2.95 q (J=9.4, 13.2 Hz), 2.76 dd (J=6.2, 10.8 Hz), 2.71 dd (J=6.3, 12.9 Hz), 2.09 m, 1.99 s, 1.93 m, 1.65 m, 0.93 d (J=6.8 Hz), 0.90 J=6.8 Hz).

Example 14
Synthesis of Acrylate Ester R016D $CrCl_2$ (17 g, 141 mmol) and then a solution of $Ni(COD)_2$ (193 mg, 0.7 mmol) in THF (~2 mL) were added to a solution of aldehyde R015D (21.1 g, 86 mmol) and E-3-iodoacrylate (30 g, 141 mmol) in THF (250 mL) in a dry box that was maintained with an inert atmosphere. Following the addition, a mild exotherm occurred, and the temperature of the mixture increased to approximately 50°–60° C. The reaction mixture was stirred for an additional 14 h, at which time additional $CrCl_2$ (5.28 g, 43 mmol) and E-3-iodoacrylate (10 g, 47 mmol) were added. After an additional 16 h, $CrCl_2$ (5.28 g, 43 mmol) and $Ni(COD)_2$ (65 mg, 0.23 mmol) again were added. Twelve hours later, TLC monitoring (20% ethyl acetate-hexanes) indicated that the starting material was consumed.

The reaction then was diluted with saturated aqueous $NH_4Cl$ (300 mL) and $CHCl_3$ (300 mL), and the resulting two-phase mixture was rapidly stirred overnight. The layers were separated, and the organic phase was rapidly stirred with saturated aqueous $NH_4Cl$ (300 mL) for 2 h. The combined aqueous phases were extracted with CHCl₃ (2×200 mL). The combined organic phases were dried once with brine, further dried over Na₂SO₄, filtered, and concentrated to a crude oil. This oil was further purified several times with silica gel FC's. For the initial columns, elutions were performed with 10–30% ethyl acetate-hexanes gradients; for later columns 10–20% ether:CH₂Cl₂ gradients were used. Acrylate ester R016D (17.4 g, 61%) was obtained as a mixture of C.4 alcohols as a slightly impure yellow oil. From examination of the ¹H NMR spectrum, the α:β ratio appeared to be approximately 1:2. The following characteristic values may be obtained by nuclear magnetic resonance spectroscopy:

¹H NMR (CDCl₃) δ: 6.99 bd (J=14.0 Hz, β), 6.96 dd (J=5.6, 15.6 Hz, α), 6.17 dd (J=1.7, 15.5 Hz, β, 6.13 dd (J=1.0, 15.4 Hz, α), 4.65 s (β), 4.61 t (J=6.6 Hz, α), 4.50 bs (β), 4.48 t (J=6.7 Hz, α), 3.75 s (β), 3.74 s (α), 3.15 dd (J=6.2, 12.4 Hz), 2.91 d (J=12.3 Hz, β), 2.71 d (J =12.5 Hz α), 1.76 s, 1.74 s, 1.44 s.

Example 15
Synthesis of Mesylates R017D

Triethylamine (13.4 mL, 96.3 mmol) was added to a solution of alcohols R016D (19.1 g, 57.6 mmol) in CH₂Cl₂ (150 mL, at 0° C.). Methanesulfonyl chloride (7 mL, 90 mmol) subsequently was added dropwise. The mixture was stirred for 20 min at 0° C., then the ice bath was removed, and the mixture was stirred an additional 30 min at ambient temperature. The reaction was quenched by addition of saturated aqueous NH₄Cl (400 mL), diluted with ethyl acetate (1 L), and shaken. The layers then were separated, and the organic layer was dried once with brine, further dried over Na₂SO₄, filtered, and then concentrated. The crude mesylate was purified by FC, eluting with a 0–30% ethyl acetate-hexane gradient affording mesylates R017D (22.0 g, 93%) as a yellow oil. The following characteristic values may be obtained by nuclear magnetic resonance spectroscopy:

¹H NMR (CDCl₃) δ: 7.08 dd (J=6.3, 15.6 Hz, α), 6.93 bdd (J=8.2, 14.8 Hz, β), 6.05 bd (J =14.4 Hz, β), 5.59 bm (α), 5.43 t (J=7.8 Hz), 3.75 s (α), 3.71 s (β), 3.20 dd (J=6.7, 12.9 Hz, α), 3.16 dd (J =5.7, 12.7 Hz, β), 3.07 bm (α), 2.99 s, 2.96 bd (J=12.7 Hz, β), 1.73 bs, 1.70 bs, 1.41 s.

Example 16
Synthesis of Olefinic Esters R018D

A 2M solution of i-PrMgCl in THF (111 mL, 222 mmol) was added dropwise to a suspension of CUCN (20 g, 222 mmol) in THF (200 mL, at −40° C.). The reaction mixture turned black and became viscous. After the addition was complete, the mixture was warmed to 0° C., stirred for an additional 30 min, then recooled to −78° C. Then, BF₃·OEt₂ (31.5g, 222 mmol) was added, the reaction mixture was stirred for 5 min, and a solution of mesylates R018D (22 g, 53.7 mmol) in THF (40 mL) then was added by cannula. After 15 min, TLC (20% ethyl acetate-hexanes) indicated that the starting material had completely disappeared. The reaction was quenched with 1:1 saturated aqueous NH₄Cl:aqueous NH₄OH (50 mL), and the mixture was allowed to warm to ambient temperature. Additional saturated aqueous NH₄Cl (400 mL), NH₄OH (50 mL), and ethyl acetate (1 L) were added, and the mixture was vigorously stirred for 1 h. The layers were filtered through CELITE®, separated, and the aqueous layer was extracted with ethyl acetate (300 mL). The combined organic phases were washed with water (400 mL), dried once with brine (1 L), dried over Na₂SO₄, filtered through MgSO₄, and then concentrated. The crude product was purified by FC, eluting with a 5–10% ethyl acetate-hexanes gradient. Esters R018D (13.8 g, 71%) were obtained as a colorless oil as a mixture of C.2 isomers. The following characteristic values may be obtained by nuclear magnetic resonance spectroscopy:

¹H NMR (CDCl₃) δ: 5.66 m, 4.78 bm, 3.66 s, 3.25 dd (J=5.6, 11.6 Hz, β), 3.24 dd (J=5.9, 11.7 Hz, α), 2.66 m, 2.57 d (J=11.7 Hz, β), 2.55 d (J=11.8 Hz, α), 1.96 b sept (J=6.7 Hz), 1.77 s, 1.74 s, 1.42 s (α), 1.41 s (β), 0.89 d (J=6.5 Hz, α), 0.87 d (J=8.0 Hz), 0.85 d (J=6.5 Hz, β).

Example 17
Synthesis of Alcohol R019D

A 1M solution of DIBAL in cyclohexane (76 mL, 76 mmol) was added to a solution of ester R018D (13.6 g, 38.0 mmol) in toluene (250 mL) stirring at room temp. The reaction was stirred for 15 min and then quenched by the addition of saturated sodium potassium tartrate (250 mL). The resulting heterogeneous mixture was stirred vigorously for 2 h at room temp, diluted with ethyl acetate (500 mL), and the organic layer then was separated, dried with brine, dried over Na₂SO₄, filtered through MgSO₄, and concentrated. The resulting crude mixture of alcohols was separated and purified by FC, eluting with a 5%–25% ethyl acetate-hexanes gradient to afford the a C.2 alcohol R019D (8.5 g, 68%) and the β C.2 alcohol isomer (3.6g, 29%). The following characteristic values may be obtained by nuclear magnetic resonance spectroscopy:

¹H NMR (CDCl₃) δ α-isomer: 5.67 dd (J=6.3, 15.3 Hz), 5.39 dd (J=9.3, 15.2 Hz), 4.83 bm, 3.65 m, 3.31 t (J=10.1 Hz), 3.26 dd (J=6.1, 11.7 Hz), 2.58 d (J=11.7 Hz), 1.99 m, 1.77 bs, 1.74 s, 1.43 s, 0.89 d (J=6.7 Hz), 0.85 d (J=6.7 Hz).

¹H NMR (CDCl₃) δ β-isomer: 5.62 dd (J=7.1, 15.2 Hz), 5.33 m, 4.73 bm, 3.64 dt (J=5.4, 15.2 Hz), 3.32 t (J=10.4 Hz), 3.36 dd (J=6.2, 11.8 Hz), 1.98 m, 1.73 bs, 1.43 s, 0.88 d (J=6.7), 0.84 d (J=6.7 Hz).

Example 18
Synthesis of Aldehyde R020D

The Dess-Martin Periodinane, 1,1,1,-triacetoxy-1,1-dihydro-1,2-benziodoxol-3(1H)-one, (5.4 g, 12.9 mmol) was suspended in diethyl ether (25 mL) under argon and stirred for 5 min. The ether was decanted, and the reagent was dried under a stream of argon for 10 min. The resulting solid was suspended in CH₂Cl₂ (25 mL), and then 4 Å molecular sieves (1 g) and t-butanol (956 mg, 12.9 mmol) were added. The mixture was stirred for 30 min, after which alcohol R019D (1.42 g, 4.31 mmol) was added. After 4 h, TLC monitoring (eluting with 20% ethyl acetate-hexanes) indicated that the reaction was complete. Diethyl ether (50 mL) was added, and the resulting suspension was filtered through CELITE®. The filtrate was washed with 10% Na₂S₂O₃ (30 mL), saturated aqueous NaHCO₃ (30 mL), and water, then dried with brine, dried over Na₂SO₄₁ filtered, and concentrated to an oil. The crude aldehyde was purified by FC, eluting with 10% ethyl acetate hexanes to afford aldehyde R020D (1.3 g, 92%) as a colorless oil. The following characteristic values may be obtained by nuclear magnetic resonance spectroscopy:

¹H NMR (CDCl₃) δ: 9.57 d (J=2.7 Hz), 5.74 dd (J =7.0, 15.3 Hz), 5.60 bm, 4.84 bm, 3.26 dd (J=6.0, 11.8 Hz), 2.70 bm, 2.56 d (J=11.8 Hz), 2.10 o (J=6.9 Hz), 1.74 s, 1.42 s, 0.94 d (J=6.7 Hz), 0.90 d (J=6.6 Hz).

Example 19
Synthesis of Acrylate Ester R021D

CrCl₂ (1.5 g, 11.9 mmol) and Ni(COD)₂ (7.3 mg, 0.026 mmol) were added sequentially to a solution of aldehyde R020D (1.3 g, 3.97 mmol) and E-3-iodoacrylate (2.5 g, 11.9 mmol) in THF (250 mL) in a dry box maintained with an inert atmosphere. The reaction mixture was stirred for 14 h, at which time TLC monitoring (20% ethyl acetate-hexanes) indicated that the starting material had been consumed.

The reaction was diluted with saturated aqueous $NH_4Cl$ (100 mL) and stirred for 1 h at room temp. After dilution with $CHCl_3$ (100 mL) followed by vigorous mixing, the resulting emulsion was filtered through CELITE®. The layers were separated, and the organic phase was dried once with brine, dried over $Na_2SO_{4l}$ filtered, and concentrated to a crude oil. The crude oil was purified by FC, eluting with 20% ethyl acetate-hexanes. Acrylate ester R021D (1.13 g, 68%) was obtained as a mixture of C.4 epimeric alcohols. The following characteristic values may be obtained by nuclear magnetic resonance spectroscopy:
$^1H$ NMR ($CDCl_3$) δ: 6.97 dd (J=4.7, 15.6 Hz), 6.01 dd (J=1.4, 15.6 Hz), 5.70 dd (J=6.5, 15.3 Hz), 5.30 m, 4.81 bm, 4.38 m, 3.26 dd (J=6.2, 11.8 Hz), 2.55 bd (J=11.9 Hz), 2.02 m, 1.73 s, 1.43 s, 0.95 d (J=6.7 Hz), 0.87 d (J=6.1 Hz).

Example 20
Synthesis of Diene Ester R022D

Triethylamine (604 μL, 4.34 mmol) was added to a solution of alcohols R021D (1.12 g, 2.71 mmol) in $CH_2Cl_2$ (15 mL at 0° C.). Methanesulfonyl chloride (314 μL, 4.06 mmol) then was added dropwise. The mixture was stirred for 20 min at 0° C., the ice bath then was removed, and the mixture was stirred at ambient temperature for approximately 30 min. At that point, TLC (eluting with 20% diethyl ether-$CH_2Cl_2$) indicated complete disappearance of starting material. The reaction was quenched by the addition of saturated aqueous $NH_4Cl$, then diluted with ethyl acetate, and shaken. The layers were separated, and the organic layer was dried once with brine, dried over $Na_2SO_4$, filtered, and then concentrated. The crude mesylate was used immediately for the following $SN^{2'}$ displacement.

A 2.0M solution of benzyl magnesium chloride in THF (5.4 mL, 10.8 mmol) was added dropwise to a suspension of CUCN in THF stirring at −40° C. After the addition was complete, the pale yellow solution was warmed to 0° C. and stirred an additional 30 min. At that point the solution was gray. It then was cooled to −78° C., $BF_3 \cdot OEt_2$ (1.3 mL, 10.8 mmol) added, and the solution was stirred an additional 10 min. Next a solution of the crude mesylate (described above, ≦2.71 mmol) dissolved in THF (5 mL), was added. This addition was followed by a rinse with THF (5 mL), and the resulting reaction mixture was stirred for 1 h at −78° C. The reaction was then quenched by the addition of a mixture of $NH_4OH$ (10 mL) and saturated aqueous $NH_4Cl$ (10 mL). The mixture was warmed to ambient temperature, and diluted with ethyl acetate and more $NH_4Cl$ solution (50 mL). The aqueous layer was separated and extracted with ethyl acetate, and the combined organic layers were washed with water, dried with brine, dried over $Na_2SO_4$, filtered, and concentrated to a crude oil. Purification by FC, eluting with 3–10% ethyl acetate-hexanes, afforded the major β diene ester R022D (478 mg, 36%, isomer) and its C.2 minor isomer (333 mg, 25%). The following characteristic values may be obtained by nuclear magnetic resonance spectroscopy:
$^1H$ NMR ($CDCl_3$) δ C.2 β isomer: 7.25 m, 7.12 m, 5.45 m, 4.72 bm, 3.62 q (J=8.7 Hz), 3.60 s, 3.21 dd (J=6.1, 11.6 Hz), 3.03 dd (J=8.0, 13.6 Hz), 2.76 dd (J=6.7, 13.6 Hz), 2.70 q (J=8.3 Hz), 2.43 (J=11.7 Hz), 1.78 s, 1.76 s, 1.55 oct (J=6.8 Hz), 1.43 S, 0.87 d (J=6.6 Hz), 0.82 d (J=6.7 Hz).
$^1H$ NMR ($CDCl_3$) δ C.2 α isomer: 7.25 m, 7.15 m, 5.45 m, 4.78 bm, 3.62 s, 3.31 m, 3.26 dd (J=6.5, 12.0 Hz), 3.07 dd (J=7.8, 13.6 Hz), 2.80 dd (J=7.5, 13.7 Hz), 2.54 d (J=11.6 Hz), 2.42 m, 1.835, 1.77 s, 1.56 oct (J=6.7 Hz), 1.45 s, 0.79 d (J=6.8 Hz).

Example 21
Synthesis of Acid R023D

A suspension of ester R022D (316 mg, 0.651 mmol) and LiOH (78 mg, 3.25 mmol) in a mixture of dioxane (2 mL) and water (2 mL) was stirred at ambient temperature overnight. The pH of the mixture was decreased to pH 2 with 0.1N HCl, and the mixture then was extracted several times with ethyl acetate. The combined organic layers were dried over $Na_2SO_4$, filtered, and concentrated to acid R023D (301 mg, 98%), which was obtained as a clear oil. The following characteristic values may be obtained by nuclear magnetic resonance spectroscopy:
$^1H$ NMR ($CDCl_3$) δ: 7.26 m, 7.17 m, 5.45 m, 5.42 m, 4.70 bm, 3.62 q (J=7.7 Hz), 3.21 dd (J=6.0, 11.6 Hz), 3.06 dd (J=7.7, 13.7 Hz), 2.78 dd (J=6.9, 13.6 Hz), 2.69 m, 2.42 d (J=11.5 Hz), 1.77 s, 1.75 s, 1.56 oct (J=6.8 Hz), 1.43 s, 0.86 d (J=6.6 Hz), 0.83 d (J=6.7 Hz).

Example 22
Synthesis of PNB Ester R024D

A solution of NMM (60 μL, 0.54 mmol) was added to a solution of acid R023D (245 mg, 0.517 mmol), EDC (119 mg, 0.62 mmol), HOBT (73 mg, 0.54 mmol), and methionine p-nitrobenzyl ester hydrochloride (199 mg, 0.62 mmol) in DMF (4 mL). The resulting solution was stirred overnight at ambient temperature. The reaction mixture was diluted with ethyl acetate, washed with water (50 mL), dried twice with brine (50 mL), dried over $Na_2SO_4$, filtered, and concentrated to a crude oil. Purification by FC, eluting with 20–30% ethyl acetate-hexanes, afforded pure PNB ester R024D (340 mg, 89%) as a colorless oil. The following characteristic values may be obtained by nuclear magnetic resonance spectroscopy:
$^1H$ NMR ($CDCl_3$) 6: 8.23 d (J=8.7 Hz), 7.49 d (J=8.7 Hz), 7.25 m, 7.18 m, 6.14 bs, 5.50 m, 4.75 bm, 4.70 dt (J=4.8, 7.5 Hz), 3.41 dt (J=6.4, 8.9 Hz), 3.23 dd (J=6.0, 11.6 Hz), 3.08 (J=8.4, 13.4 Hz), 2.73 dd (J=6.1, 13.4 Hz), 2.67 q (J=7.9 Hz), 2.46 d (J=11.7 Hz), 2.20 m, 2.1 m, 1.98 s, 1.84 m, 1.79 s, 1.76 s, 1.57 oct (J=6.7 Hz), 1.44 s, 0.87 d (J=6.2 Hz), 0.83 d (J=6.6 Hz).

Example 23
Synthesis of Acid R025D

A solution of $Na_2S \cdot 9 H_2O$ (1.67 g, 6.95 mmol) in water (5 mL) to a solution of PNB ester R024D (1.03 g, 1.39 mmol) in THF (10 mL), and the resulting mixture was stirred for 1 h 45 min at ambient temperature. The reaction was quenched by addition of 1.2 mL TFA, stirred for 15 min, and the solvents were removed under vacuum. The residue was dissolved in methanol and purified by reverse phase HPLC, eluting with 0.15% TFA in 5% acetonitrile-water to 0.15% TFA in acetonitrile to yield acid R025D (797 mg, 95%). The following characteristic values may be obtained by nuclear magnetic resonance spectroscopy:
$^1H$ NMR ($CD_3OD$) δ: 7.18 m, 7.10 m, 5.59 dd (J=7.0, 15.2 Hz), 5.51 t (J=10.4 Hz), 5.41 bm, 5.34 t (J=10.4 Hz), 4.90 bs, 4.71 bm, 4.36 dd (J=4.0, 9.3 Hz), 3.55 q (J=4.7 Hz), 3.21 dd (J=6.1, 11.8 Hz), 2.85 dd (J=8.6, 14.9 Hz), 2.62 dd (J=5.3, 13.2 Hz), 2.44 d (J=11.8 Hz), 1.99 s, 1.85 m, 1.71 s, 1.68 s, 1.66 m, 1.37 s, 1.50 oct (J=6.9 Hz), 1.37 s, 0.86 d (J=6.3 Hz), 0.82 d (J=6.7 Hz).

Example 24
Synthesis of Disulfide R026D

A solution of thiazolidine R025D (250 mg, 0.411 mmol) in acetic acid (0.6 mL), DMF (2.0 mL), and water (1.0 mL) was cooled to 0° C. for 15 min. $MeO_2CSCl$ (45 μL, 0.493 mmol) was added dropwise to this mixture. After stirring for 30 min further at 0° C., analysis by reverse phase HPLC (eluting with 0.15% TFA in 5% acetonitrile-water to 0.15% TFA in acetonitrile over 30 min) showed complete consumption of starting material. Solvents were removed under vacuum, and the residue was purified by reverse phase HPLC. Disulfide R026D (244 mg, 91%) was obtained as a colorless oil. The following characteristic values may be obtained by nuclear magnetic resonance spectroscopy:
$^1$H NMR (CD$_3$OD) δ: 7.24 m, 7.17 m, 5.58 t (J=10.3 Hz), 5.54 dd (J=8.7, 16.6 Hz), 5.39 t (J=10.4 Hz), 5.33 dd (J=6.6, 15.4 Hz), 4.42 m, 4.21 m, 2.87 s, 3.55 m, 2.89 m, 2.72 dd (J=5.9, 13.2 Hz), 2.03 m, 1.98 s, 1.93 m, 1.71 m, 1.57 oct (J=6.7 Hz), 1.42 s, 0.89 d (J=6.7 Hz), 0.86 d (J=6.7 Hz).

Example 25
Synthesis of Thiol R027D

A solution of n-Bu$_3$P (0.97 mL, 3.94 mmol) was added dropwise to a solution of disulfide R026D (863 mg, 1.32 mmol) in THF (30 mL) containing water (3 mL, ~166 mmol) at 0° C. After 18 min, analytical reverse phase HPLC (eluting with 0.15% TFA in 5% acetonitrile water to 0.15% TFA in acetonitrile over 30 min) indicated complete consumption of the starting material. The reaction mixture was loaded directly onto a preparative reverse phase HPLC column, and then purified. Thiol R027D (681 mg, 92%) was obtained as a clear oil. The following characteristic values may be obtained by nuclear magnetic resonance spectroscopy:
$^1$H NMR (CD$_3$OD) δ: 7.25 m, 7.17 m, 5.58 t (J=10.4 Hz), 5.52 dd (J=9.1, 16.8 Hz), 5.40 (J=10.4 Hz), 5.29 dd (J=6.7, 15.5 Hz), 4.43 m, 4.03 m, 3.58 q (J=8.3 Hz), 2.90 m, 2.71 dd (J=5.9, 13.2 Hz), 2.58 m, 2.03 m, 1.98 s, 1.91 m, 1.71 m, 1.58 oct (J=6.8 Hz), 1.42 s, 0.89 d (J=6.7 Hz), 0.86 d (J=6.8 Hz).

Example 26
Synthesis of Compound PD331

A solution of N-BOC protected thiol R027D (681 mg, 1.2 mmol) in CH$_2$Cl$_2$ (10 mL) and TFA (10 mL) was stirred at 0° C. for 55 min. The mixture was worked up and purified as described above, affording pure analog PD331 (354 mg, 80%).

Example 27
Synthesis of Amide R028D

A mixture of acid R023D (80 mg, 0.169 mmol), HCl·MeNHOMe (20 mg, 0.203 mmol), EDC (49 mg, 0.254 mmol), and NMM (19 mL, 0.169 mmol) in 3 mL CH$_2$Cl$_2$ was stirred at ambient temperature for 16 h. The resulting mixture was diluted with ethyl acetate (30 mL) and water (15 mL), transferred to a separatory funnel, and then shaken. The organic layer was washed with water, dried with brine, dried over Na$_2$SO$_4$, filtered, and concentrated. The crude oil was purified by FC eluting with 15% ethyl acetate-hexanes to afford the desired amide R028D (68 mg, 78%) as a colorless oil. The following characteristic values may be obtained by nuclear magnetic resonance spectroscopy:
$^1$H NMR (CDCl$_3$) δ: 7.25 m, 7.17 m, 5.60 t (J =10.2 Hz), 5.56 m, 5.47 m, 5.40 t (J=10.4 Hz), 4.77 b m, 4.08 b m, 3.30 s, 3.25 (J=6.1, 11.6 Hz), 3.10 dd (J=8.7, 12.1 Hz), 3.08 s, 2.76 q (J=8.1 Hz), 2.66 dd (J=5.2, 13.2 Hz), 2.50 d (J=11.6 Hz), 1.81 s, 1.77 s, 1,57 oct (J=6.9 Hz), 1.45 s, 0.87 d (J=6.7 Hz), 0.83 d (J=6.7 Hz).

Example 28
Synthesis of Aldehyde R029D

Lithium aluminum hydride (6 mg, 0.16 mmol) was added to a solution of amide R028D (68 mg, 0.13 mmol) in diethyl ether (5 mL) maintained at 0° C. After stirring for 30 min, the resulting reaction mixture was quenched with saturated aqueous sodium potassium tartrate and stirred an additional 30 minutes. The layers were separated and the aqueous layer extracted with ethyl acetate. The combined organic layers were dried with brine, dried over Na$_2$SO$_4$, filtered, and concentrated to the crude aldehyde, R029D used directly in the next reaction.

Example 29
Synthesis of Amine R030D

Sodium cyanoborohydride (41 mg, 0.195 mmol) was added to a solution of the hydrochloride salt of methionine p-nitrobenzyl ester (64 mg, 0.195 mmol) and crude aldehyde R029D (≦0.13 mmol) in ethanol (5 mL). The resulting mixture was stirred at ambient temperature overnight and then diluted with ethyl acetate and water. The organic layer was dried with brine, dried over Na$_2$SO$_4$, filtered, and concentrated to a crude oil. After purification by FC eluting with 20% ethyl acetate-hexanes, amine R030D (45 mg, 47%) was obtained as a white solid. The following characteristic values may be obtained by nuclear magnetic resonance spectroscopy:
$^1$H NMR (CDCl$_3$) δ: 8.24 d (J=8.8 Hz), 7.51 d (J=8.7 Hz), 7.25 t (J=7.6 Hz), 7.16 t (J=6.8 Hz), 7.11 d (J=7.6 Hz), 5.49 m, 5.42 t (J=10.4 Hz), 5.25 d (J=13.3 Hz), 5.23 ab q, 5.18 t (J=10.3 Hz), 3.37 dd (J=5.6, 7.8 Hz), 3.21 dd (J=5.9, 11.6 Hz), 2.83 m, 2.73 q (J=8.1 Hz), 2.54 m, 2.40 m, 2.04 s, 1.89 m, 1.75 s, 1.54 m, 1.44 s, 0.88 d (J=6.4 Hz), 0.86 (J=6.6 Hz).

Example 30
Synthesis of Ester R031D

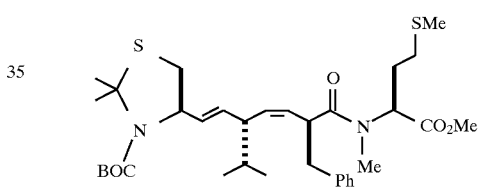

In a procedure similar to that used for the preparation of PNB ester R024D above, acid R023D (93 mg, 0.203 mmol) and N-methyl methionine methyl ester hydrochloride (36 mg,0.203 mmol) were coupled to afford ester R031D (24 mg, 19%) as a yellow oil. The following characteristic values may be obtained by nuclear magnetic resonance spectroscopy:
$^1$H NMR (CDCl$_3$) δ: 7.26 m, 7.18 m, 5.61 m, 5.48 m, 5.15 dd (J=4.4, 10.4 Hz), 4.64 dt (J=5.1, 7.3 Hz), 3.64 S, 3.26 dd (J=6.1, 7.9 Hz), 3.10 dd (J=10.0, 13.3 Hz), 2.75 s, 2.2 m, 2.11 m, 2.02 s, 1.6 m, 1.44 s, 0.88 d (J 6.9 Hz), 0.86 d (J=8.1 Hz).

Example 31
Compound PD012

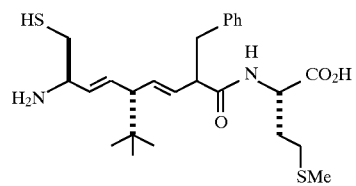

$^1$H NMR (CD$_3$OD) δ: 8.22 d (J=8 Hz), 7.13–7.26 m, 6.02 dd (J=7.3, 15.5 Hz), 5.65 dd (J=8.7, 15.3 Hz), 5.50 dd (J=7.9, 15.4 Hz), 5.43 ddd (J=1.2, 8.0, 15.6 Hz), 4.46 m, 3.82 q (J=7.3 Hz), 2.98 dd (J=11.8, 13.3 Hz), 2.81 dd (J=6.4, 15.3 Hz), 2.75 m, 2.53 t (J=7.7 Hz), 2.16 ddd (J=2.6, 8.7, 13.4 Hz), 2.05 m, 1.98 s, 1.73 m, 0.85 s.

Example 32

Compound PD022

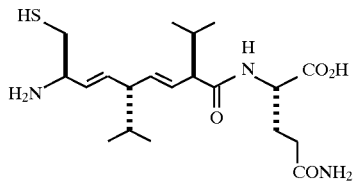

$^1$H NMR (CD$_3$OD) δ: 8.35 d (J=8 Hz), 5.91 dd (J=8.1, 15.5 Hz), 5.57 dd (J=7.3, 15.5 Hz), 5.48 dd (J=8.9, 15.4 Hz), 5.42 dd (J=7.8, 15.4 Hz), 4.35 dd (J=5.3, 8.7 Hz), 3.84 q (J=7.1 Hz), 2.80 dd (J=6.4, 14.3 Hz), 2.76 dd (J=6.1, 14.1 Hz), 2.6 m, 2.27 m, 2.1 m, 1.95 m, 1.7 m, 0.94 d (J=6.6 Hz), 0.91 d (J=6.5 Hz), 0.90 d (J=6.7 Hz), 0.88 d (J=6.9 Hz).

Example 33

Compound PD032

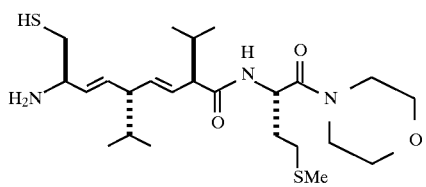

$^1$H NMR (CD$_3$OD) δ: 8.29 d (J=8.0 Hz), 5.92 dd (J=8.2, 15.6 Hz), 5.57 dd (J=7.6, 15.5 Hz), 5.46 dd (J=9.1, 15.4 Hz), 5.43 dd (J=8.1, 15.5 Hz), 4.99 dt (J=5.1, 8.4 Hz), 3.84 q (J=7.5 Hz), 3.6–3.75 m, 3.52 m, 2.81 dd (J=6.4, 14.0 Hz), 2.74 (J=6.2, 14.0 Hz), 2.4–2.65 m, 2.06 s, 1.90 m, 1.71 o (J=6.6 Hz), 0.91 d (J=6.4 Hz), 0.90 d (J=5.9 Hz), 0.89 d (J=6.6 Hz), 0.86 d (J=6.8 Hz).

Example 34

Compound PD042

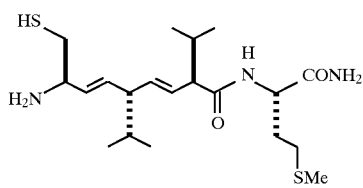

$^1$H NMR (CD$_3$OD) δ: 8.12 d (J=7.9 Hz), 5.92 dd (J=8.1, 15.5 Hz), 5.57 dd (J=7.6, 15.4 Hz), 5.46 dd (J=9.4, 14.9 Hz), 5.43 dd (J=7.7, 15.2 Hz), 4.48 m, 3.84 q (J=7.3 Hz), 2.81 dd (J=6.4, 14.5 Hz), 2.74 dd (J=6.1, 14.5 Hz), 2.59 m, 2.48 m, 2.06 s, 2.05 m, 1.90 m, 1.71 o (J=6.7 Hz), 0.91 d (J=6.0 Hz), 0.91 (J=6.5 Hz), 0.90 d (J=6.1 Hz), 0.87 d (J=6.7 Hz).

Example 35

Compound PD052

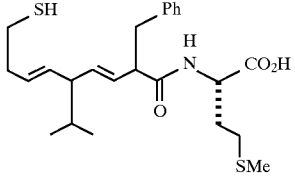

Isomer I $^1$H NMR (CD$_3$OD) δ: 8.12 d (J=8.2 Hz), 7.13–7.25 m, 5.52 dd (J=6.5, 14.8 Hz), 5.47 dd (J=7.1, 15.2 Hz), 5.40 dd (J=7.7, 15.4 Hz), 5.26 dt (J=7.2, 14.3 Hz), 4.44 dt (J=3.7, 9.1 Hz), ~3.30 m, 2.98 dd (J=9.3, 13.3 Hz), 2.73 dd (J=6.3, 13.3 Hz), 2.50 (J=7.2 Hz), 2.42 (J=6.9 Hz), 2.28 (J=7.0 Hz), ~2.1 m, 1.98 s, ~1.32 m, 1.57 o (J=6.7 Hz), 0.83 d (J=6.8 Hz), 0.83 d (J=6.7 Hz).

Example 36

Compound PD062

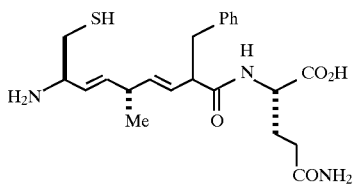

$^1$H NMR (CD$_3$OD) δ: 8.26 d (J=8 Hz), 7.05–7.3 m, 5.62 dd (J=8.0, 14.1 Hz), 5.55 dd (J=10.0, 14.1 Hz), 4.28 m, 3.71 m, 3.01 m, 2.78 m, 2.35 m, 2.23 m, 1.65–2.12 m, 0.99 d (J=7.2 Hz).

Example 37

Compound PD072

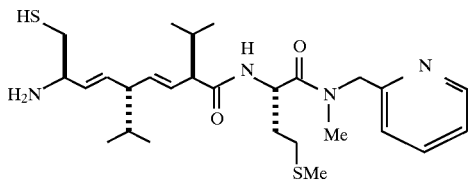

$^1$H NMR (CD$_{3l\ OD}$) δ: 8.63 d (J=5.0 Hz), 8.16 t (J=7.2 Hz), 7.62 d (J=7.7 Hz), 7.50 m, 5.92 dd (J=7.9, 15.3 Hz), 5.57 dd (J=7.6, 15.3 Hz), 5.47 dd (J=9.9, 16.5 Hz), 5.43 dd (J=8.1, 15.5 Hz), 5.02 m, 4.99 d (J=14.5 Hz), 4.64 d (J=16.1 Hz), 3.84 m, 3.32 s, 2.8–3.0 m, 2.09 s, 1.05 m, 1.70 m, 0.91 d (J=6.7 Hz), 0.90 d (J=6.6 Hz), 0.86 d (J=6.9 Hz), 0.83 d (J=6.7 Hz).

Example 38

Compound PD082

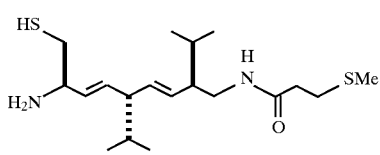

$^1$H NMR (CD$_3$OD) δ: 8.07 t (J=5.2 Hz), 5.50 dd (J=8.7, 15.2 Hz), 5.41 dd (J=9.1, 15.3 Hz), 3.63 m, 3.26 m, 3.06 dd (J=6.7, 10.7 Hz), 2.73 dd (J=9.3, 10.5 Hz), 2.47 m, 2.04 s, 2.00 m, 1.90 m, 1.6–1.8 m, 0.92 d (J=6.7 Hz), 0.89 d (J=6.7 Hz), 0.87 d (J=6.8 Hz), 0.83 d (J=6.8 Hz).

Example 39
Compound PD092

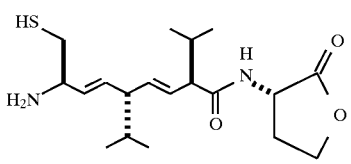

¹H NMR (CD₃OD) δ: 8.54 d (J=7.7 Hz), 5.92 dd (J=8.0, 15.5 Hz), 5.56 dd (J=7.5, 15.4 Hz), 5.46 dd (J=9.5, 14.8 Hz), 5.42 dd (J=8.2, 15.4 Hz), 4.54 m, 4.43 dt (J=1.9, 9.0 Hz), 4.13 m, 3.84 q (J=7.2 Hz), 2.82 dd (J=6.4, 14.5 Hz), 2.74 dd (J=6.1, 14.5 Hz), 2.60 q (J=7.0 Hz), 2.52 m, 2.23 m, 1.93 m, 1.70 o (J=6.7 Hz), 0.96 d (J=6.6 Hz), 0.92 d (J=6.5 Hz), 0.90 d (J=6.4 Hz), 0.90 d (J=6.8 Hz).

Example 40
Compound PD102

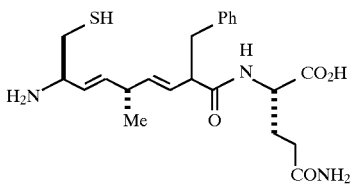

¹H NMR (CD₃OD) δ: 8.23 d (J=7.9 Hz), 7.12–7.24 m, 5.61 dd (J=7.8, 15.5 Hz), 5.51 dd (J=7.8, 15.5 Hz), 4.33 m, 3.73 m, 3.36 m, 3.05 m, 2.77 m, 2.40 m, 1.69–2.35 m, 1.59 q (J=11.2 Hz), 1.04 d (J=6.8 Hz).

Example 41
Compound PD112

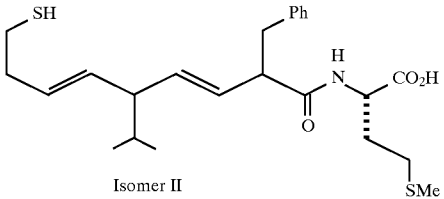

¹H NMR (CD₃OD) δ: 8.11 d, (J=8.1 Hz), 7.12–7.25 m, 5.54 dd (J=7.2, 15.4 Hz), 5.48 dd (J=7.4, 15.4 Hz), 5.43 dd (J=7.3, 15.5 Hz), 5.35 dt (J=15.7, 6.3 Hz), 4.43 m, 2.99 dd (J=9.4, 13.3 Hz), 2.74 dd (J =6.3, 13.3 Hz), 2.37–2.50 m, 2.28 q (J=6.6 Hz), ~2.1 m, 1.98 s, ~1.73 m, 1.57 o (J=6.7 Hz), 0.81 d (J=6.8 Hz), 0.79 d (J=6.8 Hz).

Example 42
Compound PD122

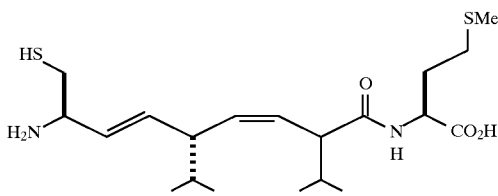

¹H NMR (CD₃ₗ ₒD) δ: 8.20 d (J=7.9 Hz), 5.84 dd (J=7.8, 15.4 Hz), 5.55 t (J=10.5 Hz), 5.46 t (J=10.0 Hz), 5.45 dd (J=7.1, 16.1 Hz), 4.55 m, 3.83 q (J=6.9 Hz), 2.94 m, 2.80 dd (J=6.1, 14.1 Hz), 2.72 dd (J=6.1, 14.0 Hz), 2.52 m, 2.12 m, 2.07 s, 1.93 m, 1.63 m, 0.95 d (J=6.3 Hz), 0.94 d (J=6.4 Hz), 0.89 d (J=6.8 Hz), 0.87 d (J =6.8 Hz).

Example 43
Compound PD132

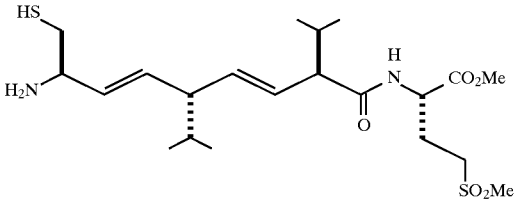

¹H NMR (CD₃OD) δ: 8.51 d (J=8 Hz), 5.91 dd (J=8, 16 Hz), 5.58 dd (J=8, 16 Hz), 5.47 dd (J=8, 17 Hz), 5.42 dd (J=8, 16 Hz), 4.57 m, 3.84 q (J=7 Hz), 3.73 s, 3.17 m, 3.04 m, 2.96 s, 2.82 dd (J=6.4, 14.0 Hz), 2.74 dd (J=6.5, 14.1 Hz), 2.59 m, 2.34 m, 2.12 m, 1.92 m, 0.93 d (J=6.4 Hz), 0.92 d (J=6.6 Hz), 0.91 d (J=6.9 Hz), 0.89 d (J=7.0 Hz).

Example 44
Compound PD142

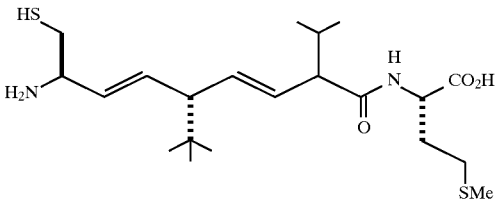

¹H NMR (CD₃OD) δ: 8.34 d (J=8.1 Hz), 6.05 dd (J=6.8, 15.6 Hz), 5.64 (J=8.8, 15.3 Hz), 5.46 ddd (J=1.2, 7.7, 16.1 Hz), 5.42 dd (J=9.4, 15.4 Hz), 4.58 m, 3.81 q (J=6.8 Hz), 2.81 dd (J=6.5, 14.2 Hz), 2.75 dd (J=6.3, 14.2 Hz), 2.55–2.65 m, 2.50 dt (J=13.5, 7.9 Hz), 2.14 m, 2.08 s, 1.94 m, 0.93 s, 0.91 d (J=6.4 Hz), 0.90 d (J=6.5 Hz).

Example 45
Compound PD152

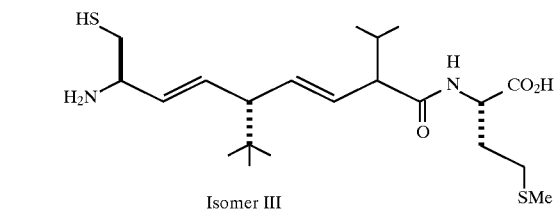

¹H NMR (CD₃OD) δ: 8.31 d (J=8.0 Hz), 6.01 dd (J=8.6, 15.5 Hz), 5.65 dd (J=8.4, 15.3 Hz), 5.46 dd (J=9.0, 15.5 Hz), 5.42 dd (J=8.3, 15.2 Hz), 4.53 m, 3.85 q (J=6.7 Hz), 2.81 dd (J=6.5, 14.1 Hz), 2.75 dd (J=6.1, 14.1 Hz), 2.51–2.61 m, 2.45 dt (J=13.4, 7.9 Hz), 2.1 m, 2.06 s, 0.93 d (J=6.6 Hz), 0.90 s, 0.86 d (J=6.7 Hz) (an epimer of PD142).

Example 46
Compound PD162

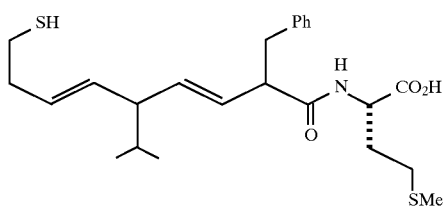

$^1$H NMR (CD$_3$OD) δ: 8.23 d (J=8.0 Hz), 7.11–7.24 m, 5.43 dd (J=7.9, 15.5 Hz), 5.36 dd (J=7.3, 15.3 Hz), 5.33 dd (J=7.6, 15.4 Hz), 5.13 dt (J=14.5, 7.2 Hz), 4.52 m, 3.27 q (J=7.5 Hz), 3.04 dd (J=6.7, 13.6 Hz), 2.73 dd (J =8.3, 13.6 Hz), 2.36 –2.52 m, 2.24 q (J=7.0 Hz), 2.09 m, 2.04 s, ~1.9 m, 1.53 o (J=6.7 Hz), 0.79 d (J=6.7 Hz), 0.788 (J=6.8 Hz).

Example 47
Compound PD172

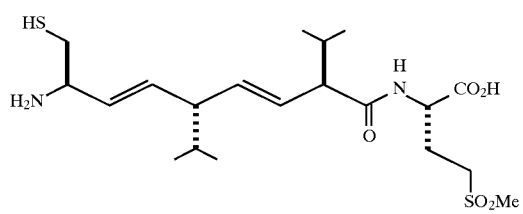

$^1$H NMR (CD$_3$OD) δ: 8.38 d (J=7.6 Hz), 5.87 dd (J=8.2, 15.5 Hz), 5.55 dd (J=7.4, 15.5 Hz), 5.45 dd (J=9.1, 15.4 Hz), 5.39 dd (J=7.8, 15.2 Hz), 4.51 m, 3.80 m, 3.60 m, 3.15 m, 3.00 m, 2.92 s, 2.78 dd (J=6.3, 14.2 Hz), 2.70 dd (J=5.9, 14.1 Hz), 2.56 m, 2.33 m, 2.09 m, 1.89 m, 1.68 o (J=6.7 Hz), 0.89 d (J=5.8 Hz), 0.88 d (J=6.7 Hz), 0.85 d (J=5.5 Hz), 0.85 d (J=6.8 Hz).

Example 48
Compound PD182

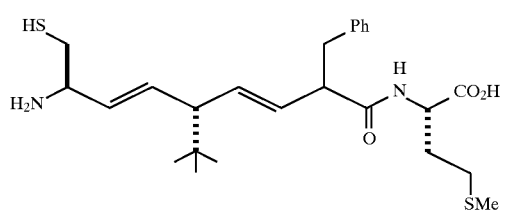

$^1$H NMR (CD$_3$OD) δ: 8.27 d (J=8.0 Hz), 7.12–7.25 m, 5.90 dd (J=8.7, 15.5 Hz), 5.57 dd (J=7.7, 15.4 Hz), 5.48 dd (J=8.0, 15.4 Hz), 5.32 dd (J=7.8, 15.4 Hz), 4.49 m, 3.81 q (J=6.6 Hz), 3.32 dd (J=8.1, 15.7 Hz), 2.68–2.82 m, 2.35–2.51 m, 2.1m, 2.04 s, 1.90 m, 0.83 s.

Example 49
Compound PD192

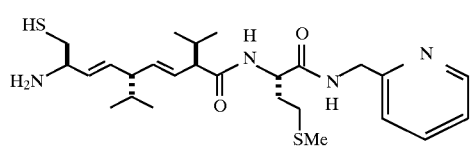

$^1$H NMR (CD$_3$OD) δ: 8.70 d (J=5.3 Hz), 8.39 dt (J=0.9, 7.7 Hz), 7.89 d (J=8.1 Hz), 7.81 t (J=6.2 Hz), 5.92 dd (J=8.4, 15.6 Hz), 5.56 dd (J=7.7, 16.1 Hz), 5.47 dd (J=9.8, 16.2 Hz), 5.42 dd (J=7.9, 15.7 Hz), 4.76 d (J=16.8 Hz), 4.60 d (J=16.8 Hz), 4.47 dd (J=5.3, 9.1 Hz), 3.84 q (J=7.4 Hz), 2.80 dd (J=6.5, 12.9 Hz), 2.74 dd (J=6.1, 12.9 Hz), 2.42–2.66 m, 2.07 s, 1.94 m, 1.70 o (J=6.7 Hz), 0.91 d (J=6.9 Hz), 0.89 d (J=6.9 Hz), 0.86 d (J=6.8 Hz), 0.83 d (J=6.7 Hz).

Example 50
Compound PD202

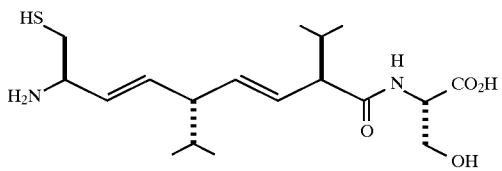

$^1$H NMR (CD$_3$OD) δ: 8.08 d (J=8.3 Hz), 5.92 dd (J=9.2, 15.6 Hz), 5.57 dd (J=7.3, 15.5 Hz), 5.49 dd (J=9.0, 15.4 Hz), 5.43 dd (J=8.0, 15.2 Hz), 4.46 dd(J=4.5, 9.2 Hz), 3.89 dd (J=5.0, 11.1 Hz), ~3.8 m, 3.76 dd (J=4.1, 11.1 Hz), ~3.65 m, 2.55–2.90 m, 1.95 m, 1.70 m, 0.95 d (J=6.5 Hz), 0.91 d (J=6.7 Hz), 0.90 d (J=6.2 Hz), 0.89 d (J=6.1 Hz).

Example 51
Compound PD212

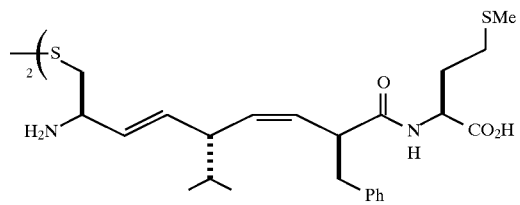

$^1$H NMR (CD$_3$OD) δ: 8.10 d (J=8.6 Hz), 7.13–7.30 m, 5.79 dd (J=7.8, 15.4 Hz), 5.64 t (J=10.4 Hz), 5.41 dd (J=8.1, 15.2 Hz), 5.38 t (J=10.6 Hz), 4.43 m, 4.00 q (J=6.6 Hz), 3.58 dt (J=5.8, 9.2 Hz), 3.10 dd (J=6.0, 13.9 Hz), 2.94 m, 2.70 dd (J=5.6, 13.2 Hz), 2.05 m, 1.98 s, 1.90 m, 1.70 m, 1.63 o (J=6.9 Hz), 0.92 d (J=6.6 Hz), 0.89 (6.7 Hz).

Example 52
Compound PD222

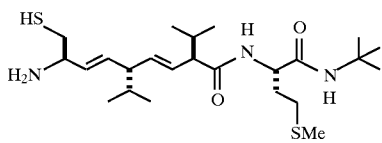

$^1$H NMR (CD$_3$OD) δ: 8.07 d (J=8 Hz), 5.92 dd (J=8.0, 15.1 Hz), 5.56 dd (J=8.1, 15.1 Hz), 5.46 m, 4.36 m, 3.84 q (J=6.5 Hz), 2.81 dd (J=7.2, 14.4 Hz), 2.74 dd (J=6.3, 14.4 Hz), 2.05 s, 1.94 m, 1.82 m, 1.58 m, 1.31 s, 0.91 d (J=6.4 Hz), 0.90 d (J=6.4 Hz), 0.89 d (J=6.3 Hz). 0.88 d (J=6.3 Hz).

Example 53

Compound PD301

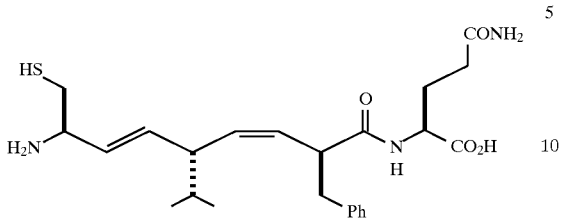

$^1$H NMR (CD$_3$OD) δ: 7.24 m, 7.19 m, 5.75 dd (J =7.9, 15.4 Hz), 5.62 t (J=10.4 Hz), 5.41 t (J=10.6 Hz), 5.30 dd (J=7.6, 15.6 Hz), 4.29 m, 3.77 q (J=6.5 Hz), 3.59 q (J=8.2 Hz), 2.94 m, 2.75 m, 1.5–2.0 m, 0.93 d (J=6.7 Hz), 0.89 d (J=6.7 Hz).

Example 54

Compound PD311

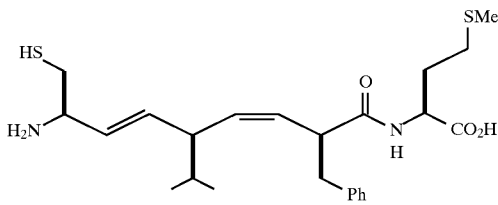

$^1$H NMR (CD$_3$OD) δ: 8.22 d (J=9.9 Hz), 7.24 m, 7.18 m, 5.70 dd (J=7.2, 16.6 Hz), 5.67 t (J=11.1 Hz), 5.36 t (J=11.1 Hz), 5.08 dd (J=8.1, 17.0 Hz), 4.48 m, 3.71 q (J=6.8 Hz), 3.56 q (J=6.8 Hz), 3.05 dd (J=6.8, 13.4 Hz), 2.83 q (J=7.8 Hz), 2.7 m, 2.47 m, 2.38 m, 2.07 m, 2.03 s, 1.90 m, 1.64 oct (J=4.4 Hz), 0.90 d (J=6.6 Hz), 0.86 (J=6.7 Hz).

Example 55

Compound PD321

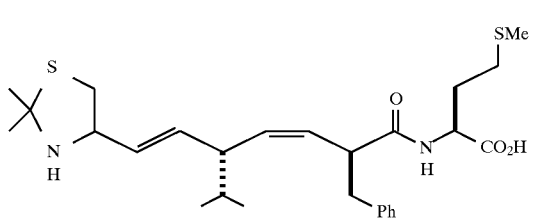

$^1$H NMR (CD$_3$OD) δ: 8.11 d (J=8.2 Hz), 7.26 m, 7.19 m, 5.99 dd (J=7.9, 15.3 Hz), 5.67 t (J=10.4 Hz), 5.49 dd (J=8.6, 15.6 Hz), 5.42 t (J=10.6 Hz), 4.64 q (J=8.4 Hz), 4.45 dd (J=4.2, 9.3 Hz), 3.58 dt (J=6.6, 9.4 Hz), 3.39 dd (J=6.9, 11.6 Hz), 3.13 dd (J=9.9, 11.6 Hz), 2.96 m, 2.69 dd (J=6.2, 13.4 Hz), 2.5 m, 1.99 s, 1.95 m, 1.80 s, 1.79 s, 1.73 m, 1.66 oct (J=6.9 Hz), 0.94 d (J=6.7 Hz), 0.90 d (J=6.7 Hz).

Example 56

Compound PD341

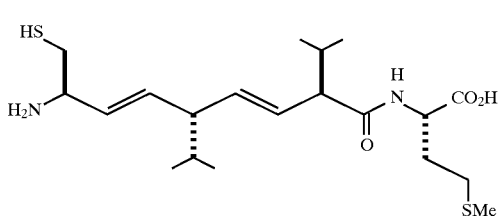

$^1$H NMR (CD$_3$OD) δ: 8.23 d (J=7.7 Hz), 5.89 dd (J=8.0, 15.4 Hz), 5.54 dd (J=7.5, 15.2 Hz), 5.45 dd (J=8.4, 15.9 Hz), 5.41 dd (J=8.0, 15.7 Hz), 4.52 m, 3.84 q (J =6.7 Hz), 2.82 dd (J=6.4, 13.9 Hz), 2.75 dd (J=6.1, 14.0 Hz), 2.59 m, 2.53 m, 2.47 m, 2.12 m, 2.07 s, 1.94 m, 1.71 m, 1.48 m, 0.95 d (J=6.6 Hz), 0.93 d (J=6.4 Hz), 0.91 d (J=6.6 Hz), 0.89 d (J=6.9 Hz).

Example 57

Compound PD351

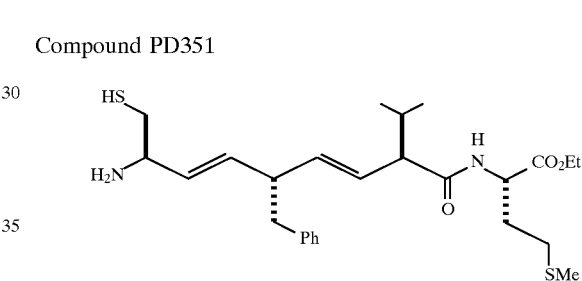

$^1$H NMR (CD$_3$OD) δ: 8.36 d (J=7.6 Hz), 7.25 m, 7.16 m, 5.89 dd (J=7.4, 15.7 Hz), 5.55 dd (J=6.8, 15.5 Hz), 5.45 dd (J=9.0, 15.5 Hz), 5.40 dd (J=7.4, 15.5 Hz), 4.48 m, 4.16 q (J=7.1 Hz), 3.81 q (J=6.9 Hz), 3.17 pent. (J=7.1 Hz), 2.77 d (J=7.3 Hz), 2.75 dd (J=6.8, 15.0 Hz), 2.68 dd (J=6.0, 14.0 Hz), 2.53 m, 2.45 m, 2.06 s, 1.89 m, 1.25 t (J=7.1 Hz), 0.92 (J=6.6 Hz), 0.83 d (J =6.7 Hz).

Example 58

Compound PD361

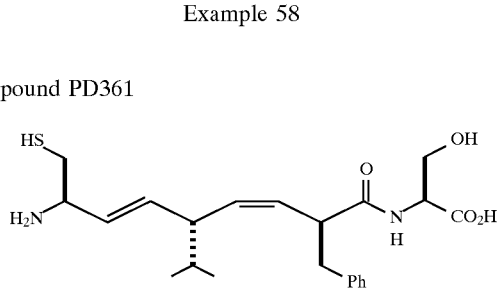

$^1$H NMR (CD$_3$OD) δ: 7.96 d (J=7 Hz), 7.25 m, 7.20 m, 5.67 dd (J=8.3, 15.9 Hz), 5.61 t (J=10.6 Hz), 5.40 t (J=10.6 Hz), 5.19 dd (J=7.5, 15.5 Hz), 4.43 m, 3.5–3.8 m, 3.03 m, 2.85 q (J=8.1 Hz), 2.72 m, 1.6 m, 0.91 d (J=6.7 Hz), 0.88 d (J=6.8 Hz).

Example 59

Compound PD371

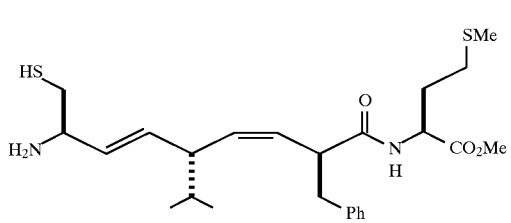

$^1$H NMR (CD$_3$OD) δ: 8.21 d (J=8.1 Hz), 7.26 m, 7.18 m, 5.82 dd (J=7.7, 15.4 Hz), 5.65 t (J=10.4 Hz), 5.40 dd (J=8.1 15.6 Hz), 5.39 t (J=10.5 Hz), 4.47 dt (J=3.3, 6.6 Hz), 4.00 q (J=7.3 Hz), 3.65 s, 3.57 dt (J=5.7, 9.6 Hz), 3.07 dd (J=6.3, 14.1 Hz), 2.95 m , 2.70 dd (J=5.6, 13.3 Hz), 2.05 m, 1.97 s, 1.89 m, 1.69 m, 0.95 d (J=6.7 Hz), 0.90 (J=6.8 Hz).

Example 60

Compound PD381

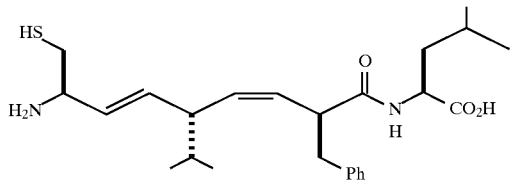

$^1$H NMR (CD$_3$OD) δ: 8.06 d (J=8.4 Hz), 7.25 m, 7.18 m, 5.78 dd (J=7.8, 15.5 Hz), 5.64 t (J=10.2 Hz), 5.41 t (J=10.5 Hz), 5.34 dd (J=7.7, 15.3 Hz), 4.34 q (J=7.4 Hz), 3.79 q (J=6.4 Hz), 3.59 q (J=8.3 Hz), 3.30 d (J=1.5 Hz), 2.94 m, 2.78 dd (J=6.1, 14.2 Hz), 2.71 dd (J=5.9, 13.6 Hz), 1.65 m, 1.43 m, 1.12 m, 0.94 d (J=6.6 Hz), 0.90 d (J=6.7 Hz), 0.80 d (J=6.5 Hz), 0.76 d (J=6.4 Hz).

Example 61

Compound PD391

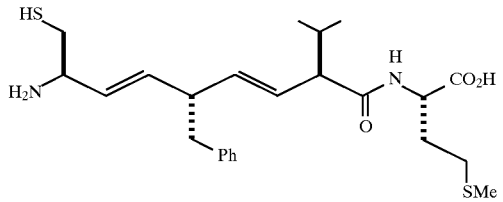

$^1$H NMR (CD$_3$OD) δ: 8.25 d (J=7.7 Hz), 7.25 m, 7.16 m, 5.89 dd (J=7.4, 15.7 Hz), 5.56 dd (J=6.8, 15.5 Hz), 5.46 dd (J=9.6, 16.2 Hz), 5.40 dd (J=8.0, 15.6 Hz), 4.48 m, 3.81 q (J=6.6 Hz), 3.17 pent, (J=7.1 Hz), 2.77 d (J=7.4 Hz), 2.75 dd (J=6.8, 16.0 Hz), 2.68 dd (J=6.1, 14.2 Hz), 2.54 m, 2.46 m, 2.10 m, 2.07 s, 1.89 m, 0.92 d (J=6.6 Hz), 0.83 d (J=6.7 Hz).

Example 62

Compound PD401

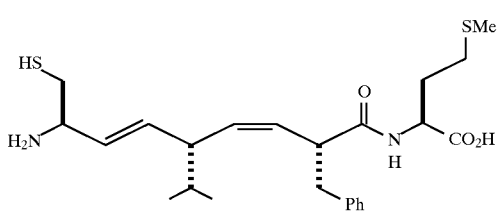

$^1$H NMR (CD$_3$OD) δ: 8.26 d (J=7.9 Hz), 7.23 m, 7.17 m, 5.81 dd (J=8.1, 15.6 Hz), 5.48 m, 5.32 dd (J=7.8, 15.5 Hz), 4.49 m, 3.80 q (J=6.9 Hz), 3.06 dd (J=7.2, 13.9 Hz), 2.80 ab m, 2.71 ab m, 2.53 m, 2.46 dd (J=5.1, 8.1 Hz), 2.39 m, 2.37 m, 2.05 s, 1.89 m, 1.62 oct (J=6.5 Hz), 0.83 d (J=6.2 Hz).

Example 63

Compound PD411

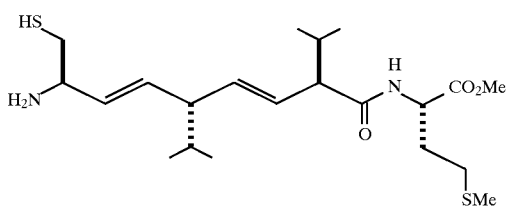

$^1$H NMR (CD$_3$OD) δ: 8.38 d (J=7.7 Hz), 5.89 dd (J=8.2, 15.3 Hz), 5.53 dd (J=7.5, 15.3 Hz), 5.44 dd (J=9.4, 14.8 Hz), 5.40 ddd (J=0.8, 8.2, 15.1 Hz), 4.54 ddd (J=3.1, 6.4, 12.2 Hz), 3.83 q (J=6.7 Hz), 3.70 s, 2.83 dd (J=7.6, 13.9 Hz), 2.74 dd (J=6.0, 14.0 Hz), 2.56 m, 2.45 m, 2.12 m, 2.06 s, 1.93 m, 1.71 oct (J=6.6 Hz), 0.95 d (J=6.5 Hz), 0.92 d (J=6.7 Hz), 0.91 d (J=6.7 Hz), 0.89 d (J=6.6 Hz).

Example 64

Compound PD421

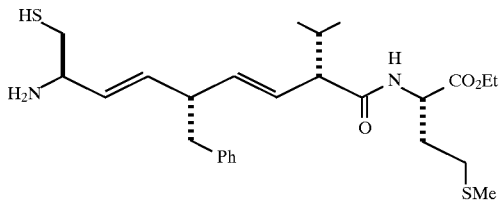

$^1$H NMR (CD$_3$OD) δ: 8.36 d (J=7.0 Hz), 7.25 m, 7.16 m, 5.93 dd (J=6.4, 15.7 Hz), 5.4 m, 4.54 m, 4.16 q (J=7.2 Hz), −3.8 m 3.17 m, 2.80 m, 2.69 m, 2.54 m, 2.07 s, 0.83 (J=6.8 Hz), 0.65 d (J=6.7 Hz).

Example 65

Synthesis of Compound PD431

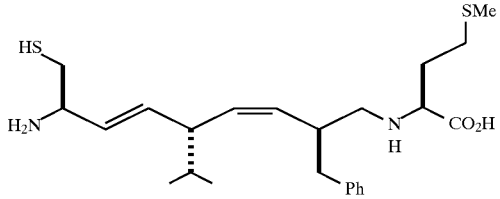

Amine R030D was converted to analog PD431 using the same methods used above for the conversion of ester R024D to analog PD331. The following characteristic values may be obtained by nuclear magnetic resonance spectroscopy:
$^1$H NMR (CD$_3$OD) δ: 5.60 dd (J=7.4, 15.5 Hz), 5.54 t (J=10.0 Hz), 5.36 t (J=10.2 Hz), 5.14 dd (J=7.4, 15.4 Hz), 3.79 t (J=6.1 Hz), 3.11 m, 2.94 m, 2.86 dd (J=5.4, 13.2 Hz), 2.78 q (J=8.4 Hz), 2.71 dd (J=6.0, 14.2 Hz), 2.63 m, 2.14 m (J=6.6 Hz), 2.09 s, 1.66 oct (J=7.0 Hz), 0.93 d (J=6.6 Hz), 0.92 d (J=6.7 Hz).

Example 66

Compound PD441

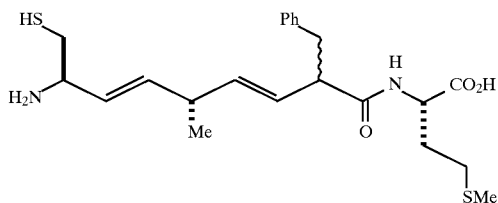

$^1$H NMR (CD$_3$OD) δ: 8.24 d (J=8.2 Hz), 8.17 d (J=8.2 Hz), 7.21 m, 7.15 m, 5.87 dd (J=6.2, 15.6 Hz), 5.79 dd (J=6.9, 15.6), 5.55 m, 5.43 dd (J=6.5, 15.7 Hz), 5.40 dd (J=7.3, 9.0 Hz), 5.33 dd (J=7.8, 15.6 Hz), 4.45 m, 3.78 q (J=6.6 Hz), 3.76 q (J=6.6 Hz), 3.28 m, 3.04 dd (J=7.2, 13.5 Hz), 2.96 dd (J=10.0, 13.2 Hz), 2.87 m, 2.73 m, 2.46 m, 2.39 m, 2.11 m, 2.03 s, 1.96 s, 1.08 d (J=6.8 Hz), 1.05 d (J=6.9 Hz).

Example 67

Synthesis of Compound PD451

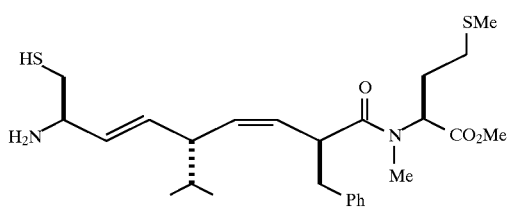

Ester R031D was converted to analog PD451 using the same methods used above for the conversion of ester R025D to analog PD331. The following characteristic values may be obtained by nuclear magnetic resonance spectroscopy:
$^1$H NMR (CD$_3$OD) δ: 7.27 m, 7.22 m, 5.84 dd (J=7.8, 15.6 Hz), 5.62 t (J=10.4 Hz), 5.47 t (J=10.1 Hz), 5.42 dd (J=7.0, 15.0 Hz), 5.03 dd (J=4.5, 10.3 Hz), 4.07 dt (J=5.4, 9.4 Hz), 3.83 q (J=6.9 Hz), 3.63 s, 2.87 s, 2.00 s, 0.97 d (J=7.3 Hz), 0.93 d (J=7.4 Hz).

Example 68

Amine R001A

The solid hydrochloride salt of phenylalaninyl methionine methyl ester was added to a solution of aldehyde R020D (488 mg, 1.492 mmol) in THF (20 mL). The mixture was stirred at room temp for 15 min until homogeneous. Triacetoxy sodium borohydride (1.392 g, 6.565 mmol) was added and the solution was stirred at room temp for 16 h. The reaction mixture was then diluted with ethyl acetate (100 mL) and water (50 mL) and the two phases were separated. The aqueous phase was extracted twice with ethyl acetate ( 20 mL). Ethyl acetate extracts were combined and washed with saturated aq sodium bicarbonate and then brine. The crude product was purified FC (20 g SiO$_2$) (eluting with 1:3 ethyl acetate:hexanes). Amine R001A was obtained as a colorless oil (677 mg, 73%).
$^1$H NMR (CD$_3$OD) δ: 7.2–7.3 m, 5.6 br m, 4.67 m, 5.28 m, 4.67 br m, 4.58 dd (J=4.6, 8.8 Hz), 3.69 s, 3.36 dd (J=5.5, 7.9 Hz), 3.23 dd (J=5.9, 11.8 Hz), 3.04 dd (J=5.4, 13.7 Hz), 2.81 dd (J=8.2, 13.6 Hz), 2.69 dd (J=4.6, 10.9 Hz), 2.34–2.45 m, 2.28 m, 2.07–2.10 m, 2.05 s, 1.94 m, 1.74 (s×2, 6H), 1.54 sept (J=6.8), 1.44 s, 0.85 d (J=6.8 Hz), 0.82 d (J=6.9).

Example 69

Acid R002A

A solution of lithium hydroxide (95 mg, 3.95 mmol) in water (3 mL) was added to a solution of amine R001A (245 mg, 0.395 mmol) in dioxane (3 mL). The resulting cloudy mixture was stirred at room temp for 15 min during which time it became homogeneous. The reaction was quenched by dropwise addition of 0.1N HCl (40 mL) until a pH of 5.7 was obtained. This aqueous solution was extracted four times with chloroform (40 mL). The organic extracts were combined and washed with brine, dried over sodium sulfate and evaporated. The resulting residue was purified by reverse phase HPLC to give acid R002A as a white solid (332 mg, >100%).
$^1$H NMR (CD$_3$OD) δ: 7.27–7.37 m, 5.30 br m, 5.37 br m, 4.85 br s, 4.38 dd (J=4.4, 9.3 Hz), 4.08 t ( J=7.3 Hz), 3.35 dd (J=6.0, 11.8 Hz), 3.22 d (J=7.8 Hz), 3.08 dd (J=4.6, 12.2 Hz), 2.83 br s, 2.66 d (J=12.0 Hz), 2.41 m, 2.14–2.29 m, 2.09–2.14 m, 2.04 s, 1.96 m, 1.78 s, 1.76 s, 1.66 br m, 1.49 br s, 0.90 d (J=6.6 Hz), 0.86 br m.

Example 70

Disulfide R003A

Methoxycarbonylsulfenyl chloride (63 mg, 0.494 mmol) was added to a solution of acid R002A (285 mg, 0.395 mmol) in HOAC (10 mL), DMF (1.25 mL) and water (0.625 mL) maintained at 0 ° C. The solution was stirred for 4 h, during which time it was allowed to gradually warm to room temp. All volatiles were evaporated under reduced pressure and the residue was purified by reverse phase HPLC to afford disulfide R003A (237 mg, 78%) as a white solid.
$^1$H NMR (CD$_3$OD) δ: 7.24–7.37 m, 5.61 dd (J=6.4, 15.4 Hz), 5.44 dd (J=9.8, 15.4 Hz), 4.39 dd ( J=4.4, 9.4 Hz), 4.21 q, (J=7.0 Hz), 4.09 dd (J=6.3, 8.4 Hz), 3.92 s, 3.13–3.20 m, 2.85–3.02 m, 2.41 m, 2.21–2.27 m, 2.13 m, 2.04 s, 1.98 m, 1.66 sep (J=6.6 Hz), 1.45 s, 0.90 d (J=6.7 Hz), 0.86 d (J=6.8 Hz).

Example 71

Thiol R004A

Tri-n-butyl phosphine (310 mg, 1.535 mmol) was added to a solution of disulfide R003A (237 mg, 0.307 mmol) in THF (10 mL) and H$_2$O (1 mL). The solution was stirred at room temp for 2 h. Volatiles were removed under reduced pressure and the residue was purified by reverse phase HPLC to afford thiol R004A as an impure yellow oil (338 mg, >100%, contaminated by tri-n-butyl phosphine).
$^1$H NMR (CD$_3$OD) δ: 8.67 d (J=8.6 Hz), 7.27–7.36 m, 5.62 dd (J=6.2, 15.2 Hz), 5.39 dd (J=9.5, 15.2 Hz), 4.38 br m, 4.06 m, 3.21 d (J=7.5 Hz), 3.11 dd (J=4.8, 12.0 Hz), 2.83 t (J=12.4 Hz), 2.63–2.67 br m, 2.41 m, 2.19–2.31 m, 2.13 m, 2.04 s, 1.96 m, 1.66 m, 1.46 s, 0.90 d (J=6.7 Hz), 0.85 d (J=6.8 Hz).

Example 72

Compound PA041

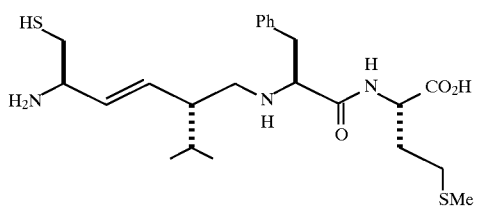

TFA (5 mL) was added to a solution of crude N-BOC-protected thiol R004A (338mg, 0.037 mmol) in dichloromethane (0.5 mL) and triethylsilane (0.5 mL) cooled in an ice-water bath. After the addition was complete, the cooling bath was removed and the solution was stirred at room temp for 1 h. All volatiles were removed under reduced pressure and the residue was purified by reverse phase HPLC. After lyophilization, analog PA041 was obtained as a white powder (109 mg, 51%). $^1$H NMR (CD$_3$OD) δ: 7.27–7.36 m, 5.73 dd (J=8.7, 15.5 Hz), 5.67 dd (J=6.9, 15.4 Hz), 4.36 dd (J=4.4, 9.4 Hz), 4.13 dd (J=6.1, 8.6 Hz), 3.89 q (J=6.6 Hz), 3.23 dd (J=5.9, 13.6 Hz), 3.19 dd (J=8.4, 13.4 Hz), 3.13 dd (J=5.3, 12.4 Hz), 3.00 dd (J=9.7, 12.3 Hz), 2.89 dd (J=6.0, 14.0 Hz), 2.83 dd (J =6.1, 14.5 Hz), 2.37 m, 2.21 m, 2.12 m, 2.03 s, 1.96 m, 1.77 o (J=5.7 Hz), 0.95 d (J=6.8 Hz), 0.90 d (J=6.8 Hz).

Example 73

Disulfide R005A

Methoxycarbonylsulfenyl chloride (77 mg, 0.605 mmol) was added to a solution of amine R001A (250 mg, 0.403 mmol) in HOAC (8 mL), DMF (1 mL), and water (0.5 mL) at 0° C. The solution was stirred for 2 h, during which time it was allowed to gradually warm to room temp. All volatiles were removed under reduced pressure and the residue was purified by reverse phase HPLC. Disulfide R005A was obtained as an oil (244 mg, 77%).

$^1$H NMR (CD$_3$OD) δ: 7.23 7.37 m, 5.61 dd (J=6.6, 15.7 Hz), 5.44 dd (J=10.1, 15.7 Hz), 4.47 dd (J=4.5, 9.0 Hz), 4.21 q (J=6.7 Hz), 4.08 t (J=7.2 Hz), 3.92 s, 3.66 s, 3.09–3.20 m, 2.82–3.02 m, 2.41 m, 2.20–2.30 m, 2.09 m, 2.03 s, 1.93 m, 1.67 m, 1.45 s, 0.91 d (J=6.7 Hz), 0.86 d (J=6.7 Hz).

Example 74

Thiol R006A

Tri-n-butyl phosphine (251 mg, 1.243 mmol) was added to a solution of disulfide R005A (244 mg, 0.311 mmol) in THF (10 mL) and water (1 mL). The solution was stirred at room temp for 2 h. Volatiles were removed under reduced pressure and the residue was purified by reverse phase HPLC to yield thiol R006A as an impure colorless oil (235 mg, >100%, contaminated by tri-n-butyl phosphine).

$^1$H NMR (CD$_3$OD) δ: 7.27–7.38 m, 5.62 dd (J=5.6, 15.4 Hz), 5.39 dd (J=10.2, 15.4 Hz), 4.46 dd (J=4.5, 9.7 Hz), 4.05–4.11 m, 3.67 s, 3.18–3.22 m, 3.07 dd (J=4.7, 12.5 Hz), 2.83 t (J=11.4 Hz), 2.65 d (J=6.8 Hz), 2.40 m, 2.20–2.30 m, 2.08 m, 2.03 s, 1.93 m, 1.67 m, 1.47 s, 0.90 d (J=6.7 Hz), 0.86 d (J=6.8 Hz).

Example 75

Compound PA091

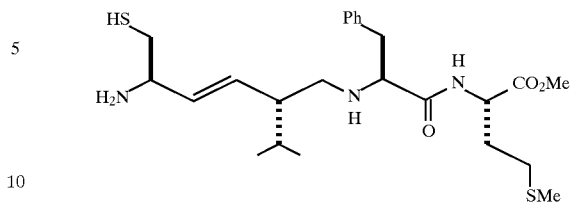

TFA (10 mL) was added to a solution of crude BOC-protectected R006A (235 mg, 0.311 mmol) in dichloromethane (1 mL) and triethylsilane (1 mL) cooled in an ice-water bath. After the addition was complete, the cooling bath was removed and the solution was stirred at room temp for an additional 3 h. All volatiles were removed under reduced pressure and the residue was purified by reverse phase HPLC. After lyophilization, compound PA091 was obtained as a white powder (115 mg, 52%).

$^1$H NMR (CD$_3$OD) δ: 7.26–7.37 m, 5.74 dd (J=8.7, 15.5 Hz), 5.67 dd (J=6.8, 15.5 Hz), 4.44 dd (J=4.6, 9.3 Hz), 4.13 dd (J=5.6, 9.2 Hz), 3.90 q (J=6.3 Hz), 3.66 s, 3.24 dd (J=5.6, 13.4 Hz), 3.16 dd (J=9.3, 13.4 Hz), 3.09 dd (J=5.5, 12.3 Hz), 3.01 dd (J=9.5, 12.2 Hz), 2.89 dd (J=5.9, 14.3 Hz), 2.83 dd (J=6.2, 14.3 Hz), 2.37 m, 2.24 m, 2.04–2.12 m, 2.03 s, 1.93 m, 1.78 o (J=5.6 Hz), 0.96 d (J=6.7 Hz), 0.91 d (J=6.8 Hz).

Example 76

Methyl amine R007A

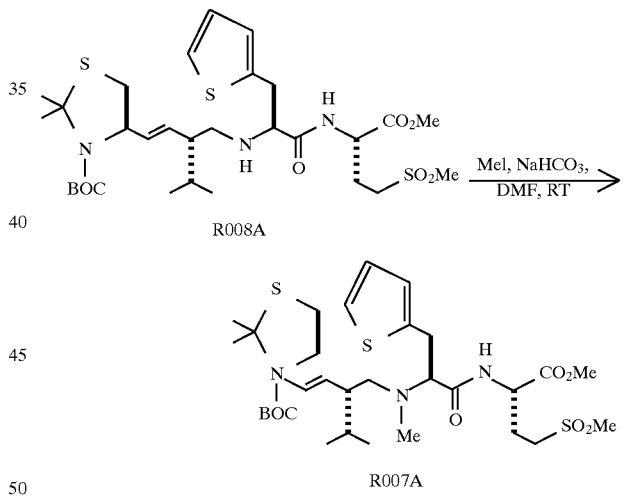

Methyl iodide (54 mg, 0.377 mmol) was added to a solution of amine R008A (226 mg, 0.343 mmol) in DMF (5 mL). The resulting mixture was stirred for 1 h at room temp. Sodium bicarbonate (32 mg, 0.377 mmol) was added and the resulting suspension was stirred at room temp for 24 h. Two percent aqueous sodium bicarbonate solution (50 mL) was added and the mixture was extracted four times with ethyl acetate (20 ml). The acetate extracts were combined, washed by brine, and dried over sodium sulfate. The volatiles were removed under reduced pressure and a yellowish oil residue was obtained. It was purified by FC (eluting with 1:1 ethyl acetate:hexanes). The desired methyl amine R007A (109 mg, 47%) was obtained as a colorless oil.

$^1$H NMR (CD$_3$OD) δ: 7.19 dd (J=0.7, 4.9 Hz), 6.87–6.91 m, 5.30–5.72 br m, 4.84 br m, 4.47 br m, 3.71 s, 3.52 br m, 3.27–3.36 m, 2.90–3.12 br m, 3.09 dd (J=5.8, 14.8 Hz), 2.94 s, 2.64 dd (J=5.4, 12.4 Hz), 2.57 d (J=11.8 Hz), 2.21–2.38 br m, 2.30 s, 2.11 m, 1.76 s, 1.75 s, 1.46 s, 0.87 d (J=5.9 Hz), 0.83 d (J=6.5 Hz).

Example 77
Compound PA011

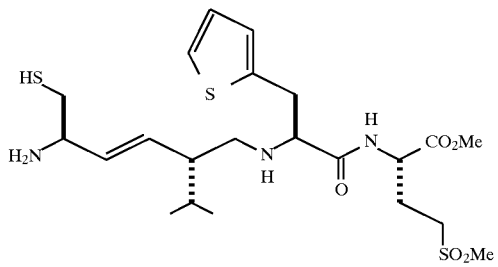

¹H NMR (CD₃OD): δ: 7.36 dd (J=1.2, 4.9 Hz), 6.99–7.02 m, 5.75 dd (J=9.2, 15.5 Hz), 5.65 dd (J=7.4, 15.6 Hz), 4.48 dd (J=5.0, 8.8 Hz), 4.11 br t (J=6.8 Hz), 3.89 dd (J=6.1, 13.3 Hz), 3.73 s, 3.44 d (J=7.1 Hz), 3.15 dd (J=5.6, 12.4 Hz), 2.91–3.05 m, 2.95 s, 2.87 dd (J=6.0, 14.3 Hz), 2.82 dd (J=6.2, 14.3 Hz), 2.33–2.43 m, 2.22 m, 1.79 m, 0.97 d (J=6.8 Hz), 0.92 d (J=6.8).

Example 78
Compound PA021

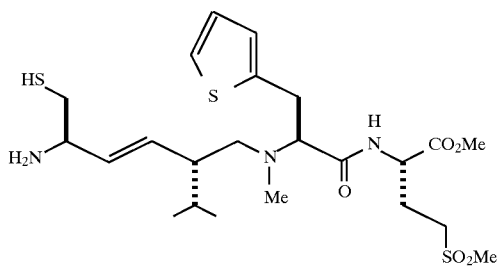

¹H NMR (CD₃OD) δ: 7.34 dd (J=2.1, 4.1 Hz), 6.99–7.01 m, 5.81 dd (J=9.4, 15.6 Hz), 5.67 br m, 4.43 dd (J=5.1, 8.7 Hz), 4.07 br m, 3.89 dd (J=6.4, 13.4 Hz), 3.71 s, 3.51 br m, 3.12–3.30 br m, 2.77–3.02 br m, 2.95 s, 2.49 br, 2.37 m, 2.21 m, 1.81 m, 0.97 d (J=6.8 Hz), 0.92 d (J=6.8 Hz).

Example 79
Compound PA031

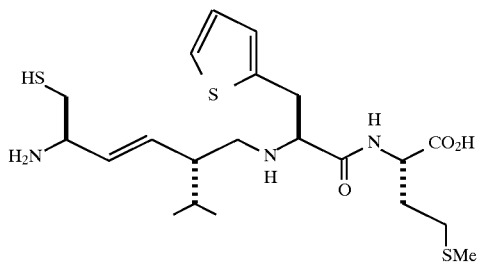

¹H NMR (CD₃OD) δ: 7.30 dd (J=1.7, 4.0 Hz), 6.96 m, 5.71 dd (J=9.5, 15.4 Hz), 5.60 dd (J=7.6, 15.8 Hz), 4.44 dd (J=4.4, 9.1 Hz), 3.98 bm, 3.86 q (J=6.5 Hz), 3.45 dd (J=7.4, 14.7 Hz), 3.38 dd (J=6.4, 14.8 Hz), 3.07 dd (J=4.9, 11.9 Hz), 2.92 bt (J=10.7 Hz), 2.85 dd (J=5.9, 13.9 Hz), 2.80 dd (J=5.9, 13.9 Hz), 2.47 ddd (J=5.1, 8.0, 13.1 Hz), 2.34 m, 2.16 m, 2.07 s, 2.02 m, 1.76 a (J=6.4 Hz), 0.96 d (J=6.7 Hz), 0.92 d (J=6.8 Hz).

Example 80
Compound PA051

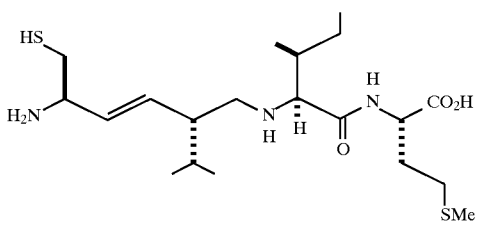

¹H NMR (CD₃OD) δ: 5.75 dd (J=9.2, 15.5 Hz), 5.65 dd (J=7.5, 15.6 Hz), 4.65 dd (J=4.4, 9.8 Hz), 3.89 q (J=6.6 Hz), 3.76 d (J=4.8 Hz), 3.08 dd (J=5.9, 12.4 Hz), 3.03 dd (J=8.5, 12.5 Hz), 2.87 d (J=6.2 Hz), 2.64 ddd (J=5.2, 7.9, 13.1 Hz), 2.54 dt (J=13.5, 7.8 Hz), 2.39 m, 2.24 m, 2.10 s, 2.03 s, 1.81 o (J=6.2 Hz), 1.66 m, 1.39 m, 1.03 d (J=6.9 Hz), 0.99 d (J=7.5 Hz), 0.97 d (J=6.9 Hz), 0.91 d (J=6.8 Hz).

Example 81
Compound PA061

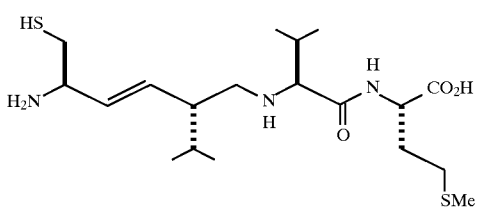

¹H NMR (CD₃OD) δ: 5.73 dd (J=9.2, 15.6 Hz), 5.64 (dd J=7.9, 16.0 Hz), 4.65 dd (J=4.2, 9.8 Hz), 3.89 q (J=6.5 Hz), 3.73 d (J=5.4 Hz), 3.07 m, 2.87 d (J=6.1 Hz), 2.65 ddd (J=5.1, 7.6, 12. 7 Hz), 2.56 dt (J=13.3, 7.7 Hz), 2.40 m, 2.28 m, 2.11 s, 2.05 m, 1.82 o (J=6.2 Hz), 1.18 d (J=6.9 Hz), 1.07 d (J=6.8 Hz), 0.99 (J=6.7 Hz), 0.93 d (J=6.8 Hz).

Example 82
Compound PA071

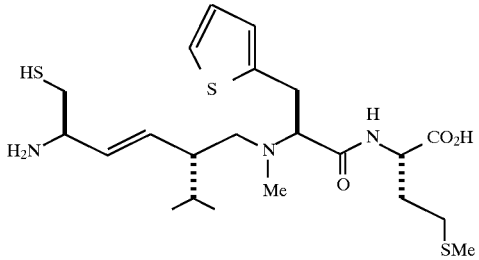

¹H NMR (CD₃OD) δ: 7.31 m, 6.96–7.00 m, 5.80 dd (J=9.4, 15.5 Hz), 5.65 dd (J=7.6, 15.4 Hz), 4.40 dd (J=4.5, 9.1 Hz), 4.06 br m, 3.88 dd (J=6.4, 13.5 Hz), 3.45–3.57 m, 3.10–3.27 m, 2.72–2.89 m, 2.79 br s, 2.41–2.47 m, 2.33 m, 2.13 m, 2.05 s, 2.00 m, 1.77 m, 0.95 d (J=6.8 Hz), 0.91 d (J=6.8 Hz).

Example 83
Compound PA051

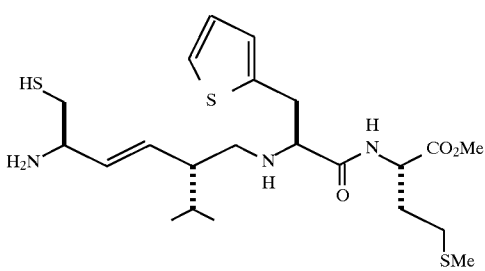

1H NMR (CD$_3$OD) δ: 7.31 dd (J=2.6, 3.7 Hz), 6.97 m, 5.71 dd (J=9.2, 15.4 Hz), 5.63 dd (J=7.3, 15.4 Hz), 4.51 dd(J=4.6, 9.2 Hz), 4.06 bm, 3.87 q (J=6.4 Hz), 3.70 s, 3.43 m, 3.09 dd (J=5.1, 11.9 Hz), 2.98 bt (J=10.9 Hz), 2.87 dd (J=6.2, 14.3 Hz), 2.81 dd (J=6.6, 14.7 Hz), 2.47 ddd (J=5.4, 7.7, 13.1 Hz), 2.35 m, 2.13 m, 2.06 s, 2.00 m, 1.78 0 (J=6.3 Hz), 0.99 d (J=7.5 Hz), 0.93 d (J=6.8 Hz).

Example 84
Compound PA101

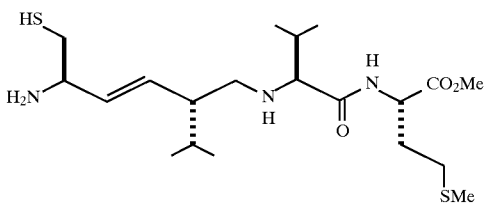

$^1$H NMR (CD$_3$OD) δ: 5.73 dd (J=9.2, 15.5 Hz), 5.63 dd (J=8.0, 15.5 Hz), 4.70 dd (J=4.4, 9.7 Hz), 3.89 q (J=6.5 Hz), 3.73 s, 3.73 d (J~4 Hz), 3.05 m, 2.87 d (J=6.1 Hz), 2.64 ddd (J=5.3, 7.6, 12.9 Hz), 2.55 dt (J=14.4, 7.2 Hz), 2.40 m, 2.25 m, 2.10 s, 2.04 m, 1.82 o (J=6.2 Hz), 1.17 d (J=6.9 Hz), 1.07 d (J=6.8 Hz), 0.99 d (J=6.7 Hz), 0.93 d (J=6.8 Hz).

Example 85
Compound PA111

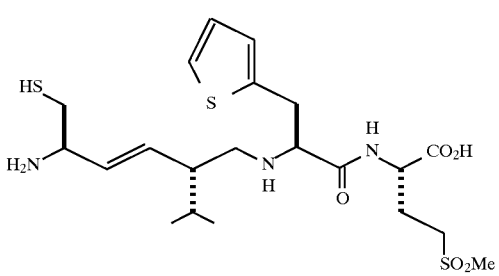

$^1$H NMR (CD$_3$OD): δ: 7.34 dd (J=2.3, 4.0 Hz), 6.97–7.01 m, 5.74 dd (J=9.3, 15.5 Hz), 5.65 dd (J=7.5, 15.6 Hz), 4.39 dd (J=4.9, 8.4 Hz), 4.08 br t (J=7.0 Hz), 3.88 dd (J=6.2, 13.3 Hz), 3.41–3.49 m, 3.16 dd (J=5.4, 12.3 Hz), 2.95–3.11 m, 2.95 s, 2.87 dd (J=5.9, 14.3 Hz), 2.81 dd (J=6.2, 14.3 Hz), 2.45–2.19 m, 1.78 m, 0.96 d (J=6.7 Hz), 0.91 d (J=6.8 Hz).

Example 86
Compound PA121

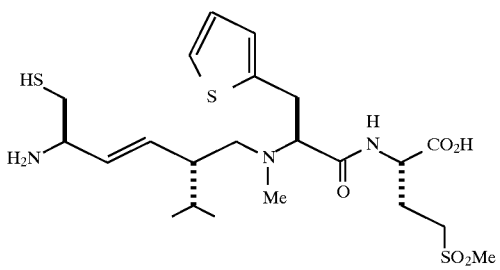

$^1$H NMR (CD$_3$OD) δ: 7.32 dd (J=1.6, 4.6 Hz), 6.97–7.01 m, 5.80 dd (J=9.4, 15.6 Hz), 5.65 dd (J=7.7, 15.6 Hz), 4.35 dd (J=5.0, 8.5 Hz), 4.05 br m, 3.88 dd (J=6.3, 13.4 Hz), 3.46–3.56 m, 3.11–3.30 br m, 2.78–3.03 m, 2.95 s, 2.35–2.48 m, 2.23 m, 1.78 m, 0.96 d (J=6.7 Hz), 0.91 d (J=6.8 Hz).

Example 87
Compound PA131

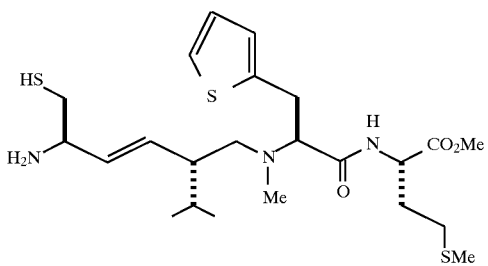

$^1$H NMR (CD$_3$OD) δ: 7.34 dd (J=1.4, 4.9 Hz), 6.97–7.00 m, 5.81 dd (J=9.4, 15.6 Hz), 5.70 dd (J=7.3, 15.8 Hz), 4.45 dd (J=4.7, 9.3 Hz), 4.16 br m, 3.89 dd (J=6.3, 13.4 Hz), 3.69 s, 3.54 br d (J=6.5 Hz), 3.29 br, 2.88 br s, 2.80–2.89 m, 2.51 br, 2.42 m, 2.28 m, 2.10 m, 2.04 s, 1.97 m, 1.78 m, 0.97 d (J=6.8 Hz), 0.92 d (J=6.8 Hz).

Example 88
Compound PA141

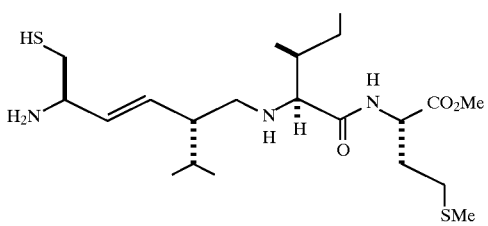

$^1$H NMR (CD$_3$OD) δ: 5.75 dd (J=9.2, 15.6 Hz), 5.66 dd (J=7.4, 15.5 Hz), 4.71 dd (J=4.4, 9.8 Hz), 3.89 q (J=6.5 Hz), 3.80 d (J=4.7 Hz), 3.73 s, 3.06 d (J=7.2 Hz), 2.88 dd (J=6.1, 14.2 Hz), 2.84 dd (J=6.2, 14.1 Hz), 2.63 ddd (J=5.4, 7.6, 13.0 Hz), 2.54 dt (J=13.6, 7.6 Hz), 2.41 m, 2.20 m, 2.09 s, 2.02 m, 1.81 0 (J=6.3 Hz), 1.66 m, 1.36 m, 1.02 d (J=6.9 Hz), 0.99 d (J=7.0 Hz), 0.96 d (J=6.6 Hz), 0.91 d (J=6.8 Hz).

Example 89
Bromoolefins R002E

Sodium hydride (250 mg, 10.4 mmol) was added to a solution of L-(-)-methyl α-hydroxy-β-phenyl propionate (3.6 g, 20 mmol) and 1,3-dibromo propene (8.24 g, 41 mmol) in CH$_3$CN (60 mL) under argon at ambient temperature. Additional quantities of sodium hydride (650 mg, 27 mmol) were added batchwise at 2, 6, and 20 h. TLC (1:4 ethyl acetate:hexanes) showed complete consumption of starting material 5 h after the final sodium hydride addition. The resulting brown mixture was quenched with brine and extracted with ethyl acetate. The extract was dried with brine, dried with MgSO$_4$ and evaporated to give 5.7 g of crude product. Purification by FC (eluting with 1:9 ethyl acetate:hexanes) afforded the desired bromoolefins R002E (3.68 g, 62%) as a mixture of cis:trans olefins in a ratio of approximately 1:1. Separation of the olefin isomers could be achieved by more exhaustive chromatography. A small amount of alkyne derived from elimination of the desired bromoolefinic products was also isolated (136 mg, 3%).

$^1$H NMR (CDCl$_3$) δ cis isomer: 7.31–7.22 m , 6.24 m, 6.13 m, 4.23 m, 4.13~4.09 m , 3.74 s, 3.1~2.9 m.

$^1$H NMR (CDCl$_3$) δ trans isomer: 7.33~7.21 m, 6.20~6.10 m, 4.1~4.0 m, 3.80 dd (J=5.6, 13.2 Hz), 3.73 s, 3.09~2.95 m.

$^1$H NMR (CDCl$_3$) δ alkyne: 7.31–7.21 m, 4.38 dd (J=5.1, 7.6 Hz), 4.26 dd (J=2.4, 16.1 Hz), 4.15 dd (J=2.4, 16.1 Hz), 3.72 s, 3.1~3.0 m, 2.39 t (J=2.4 Hz).

Example 90

Alcohols R003E

A mixture of bromoolefins R002E slightly enriched in the trans isomer (cis:trans ratio=2:3) (2.533 g, 4.7 mmol), aldehyde R015D (3.9 g, 15.9 mmol) and a stirring bar in a 250 mL flask were dried on a vacuum line for 2 h at room temp and then placed under an argon atmosphere. DMSO (130 mL), freshly distilled from CaH$_2$, was added by cannula under argon pressure. The mixture was placed in a dry box, then CrCl$_2$ (9 g, 73 mmol) and Ni(COD)$_2$ (90 mg, 0.32 mmol) were added with stirring. The resulting mixture was stirred for an additional 3 d, then quenched with ammonium chloride solution and extracted with ethyl acetate (6×150 mL). The extract was washed with ammonium chloride solution, dried with MgSO$_4$ and evaporated to give 5.95 g of crude product. Purification by FC (eluting with 1:3 ethyl acetate:hexanes) furnished the desired alcohols R003E (2.51 g, 64%) as a 1:2.3 mixture of diastereomers.

Both diastereomers appear to contain a trans olefin. Moreover, similar mixtures of trans products are obtained irrespective of the configuration(s) of the starting bromoolefins.

$^1$H NMR (CDCl$_3$) δ: 7.3~7.2 m, 5.7~5.6 m, 4.45 br m, 4.34 br m, 4.15~4.0 m, 3.85 m, 3.72 s and 3.71 s (ratio 1:2.3), 3.07~2.99 m, 2.86 m, 1.78 s and 1.76 s, 1.50 s and 1.46 s.

Example 91

Trifluoroacetates R004E

Trifluoroacetic acid anhydride (5.56 g, 26.5 mmol) and triethylamine (3.96 g, 39.2 mmol) were added at room temp to a solution of alcohol R003E (2.40 g, 5.16 mmol) stirring in CH$_2$Cl$_2$ (80 mL). The mixture was stirred for 3–4 h and then quenched with brine, evaporated to remove CH$_2$Cl$_2$, and partitioned between ethyl acetate and water. The organic layer was separated and dried with MgSO$_{41}$ filtered, and evaporated to afford the crude product (5.6 g). Purification by FC (eluting with 1:3 ethyl acetate:hexanes) furnished trifluoroacetates R004E (2.53 g, 87%) as a mixture of alcohol diastereomers.

$^1$H NMR (CDCl$_3$) δ: 7.3~7.2 m, 5.83 m, 5.72 m, 5.65 m, 4.55 br m, 4.2~4.0 m, 3.85 br m, 3.73 s and 3.70 s (in the ratio of 1/2.3), 3.11~2.95 m, 2.75 m, 1.76~1.63 m 1.47 s and 1.45 s .

Example 92

Ester R005E

Cuprous cyanide (1.84 g, 20.5 mmol) and a stirring bar were heated with a heat gun under vacuum for 10 min. Freshly distilled THF (150 mL) was added by syringe and the resulting suspension was cooled to −60° C. A 2M solution of i-PrMgCl in ether (18 mL, 36 mmol) was injected and the mixture was stirred for 10 min. The dry ice bath was then replaced with an ice/water bath. Stirring was continued for an additional 1.5 h at which time the reaction mixture had become very dark.

The mixture prepared above was cooled to −78° C. and trifluoroacetates R004E (2.26 g, 4.03 mmol) dissolved in freshly distilled THF (20 mL) were added dropwise over 6 min. 20 min later the reaction mixture was quenched with saturated aqueous ammonium chloride and extracted with ethyl acetate. After drying the organic extracts with MgSO$_4$, filtration, and evaporation of solvent, a crude product was obtained (2.1 g). Purification by FC (eluting with 8% ethyl acetate:hexanes) gave the desired esters R005E (1.638 g, 50%) as a mixture of diastereomers in a ratio of 93:7 as determined by HPLC.

$^1$H NMR (CDCl$_3$) δ: 7.27~7.20 m, 5.6 dd (J=7.3, 15.1 Hz), 5.42 m, 4.75 br s, 4.0 dd (J=4.8, 8.2 Hz), 3.71 s, 3.58 dd (J=6.2, 9.0 Hz), 3.25~3.15 m), 3.0~2.9 m, 2.51 m, 2.05 m, 1.77 s, 1.70 m, 1.45 s, 0.79 d (J=7.2 Hz), 0.77 d (J=6.9 Hz).

Example 93

Acid R006E

A 0.78M solution of LiOH (19 mL, 14.4 m mol) was added to a solution of methyl ester R005E (694 mg, 1.41 mmol) stirring in dioxane (20 mL) at room temp. The mixture was stirred overnight until TLC confirmed the disappearance of starting material. The solution was acidified with 0.5N HCl and extracted with ethyl acetate. The organic layer was dried with MgSO$_4$, filtered, and concentrated to a crude product. The desired acid R006E (646 mg, 96%) was obtained after purification by FC (eluting with 1:4 methanol:ethyl acetate).

$^1$H NMR (CDCl$_3$) δ: 7.25~7.15 m , 5.55 m, 5.33 dd (J=9.1, 15.0 Hz), 4.65 br m, 3.92 m, 3.66 m, 3.21 m, 3.19~3.03 m, 2.84 m, 2.40 m, 1.97 m, 1.72 s, 1.71 s, 1.51 m, 1.41 s, 0.74 d (J=6.6 Hz), 0.71 d (J=6.7 Hz).

Example 94

Tert-butyl ester R007E

Acid R006E (66 mg, 0.14 mmol), tert-butyl methionine hydrochloride (40.6 mg, 0.17 mmol), EDC (45 mg, 0.23 mmol), HOBT (21.7 mg, 0.16 mmol) and a stirring bar were placed in a flask and dried under vacuum for 15 min, then DMF (4.5 mL) and N-methyl morpholine (19.2 mg, 0.19 mmol) were added by syringe. The resulting mixture was stirred for 18 h then partitioned between ethyl acetate and brine. The organic layer was washed successively with brine, pH 2 phosphate buffer, and then water. The organic extracts were dried with MgSO$_4$, filtered, and concentrated to afford a light yellow oil (110 mg). Purification by FC (eluting with 3:7 ethyl acetate: hexanes) afforded the desired tert-butyl ester R007E quantitatively.

$^1$H NMR (CDl$_3$) δ: 7.23~7.13 m, 6.95 d (J=7.8 Hz), 5.65 dd (J=7.1, 14.7 Hz), 5.45 br m, 4.78 br m, 4.48 m , 3.93 dd (J=3.4, 6.3 Hz), 3.54 dd (J=5.4, 8.6 Hz), 3.34 dd (J=6.9, 8.9 Hz), 3.22 dd (J=5.9, 11.4 Hz), 3.10 dd (J=3.4, 13.9 Hz), 2.89 dd (J=6.7, 13.9 Hz), 2.55 d (J=11.5 Hz), 2.03 s, 1.9~1.6 m, 1.85~1.50 m, 1.75 s 1.45 s and 1.43 s, 0.86~0.71 m.

Example 95
Disulfide R008E

Methoxycarbonyl sulfenyl chloride (11.7 mg, 0.093 mmol) was added to a solution of tert-butyl ester R007E (47.2 mg, 0.071 mmol) in 20:2:1 HOAc:DMF:H$_2$O (1.2 mL) at 0 °C. The mixture was warmed to room temp and then stirred for 1 h. After removal of all solvents under vacuum, the crude residue was purified by preparative reverse phase HPLC to afford the desired disulfide R008E (41.5 mg, 81%).
$^1$H NMR (CDCl$_3$) δ: 7.3~7.2 m, 7.06 d (J=7.8 Hz), 5.58~5.41 m, 5.18 br m, 4.54 m, 4.51 br m, 3.99 dd (J=3.5, 7.0 Hz), 3.89 s, 3.54 dd (J=5.0, 9.2 Hz), 3.40 m, 3.14 dd (J=3.4, 14.1 Hz), 3.01 br m, 2.91 dd (J=7.1, 14.1 Hz), 2.20~1.90 m, 2.04 s, 1.90~1.65 m, 1.46 s, 0.82 d (J=6.8 Hz), 0.79 d (J=6.7 Hz).

Example 96
Thiol R009E

Tri-n-butylphosphine (81.2 mg, 0.040 mmol) was added to a solution of disulfide R008E (33 mg, 0.046 mmol) dissolved in THF (0.8 mL) and water (27 mg, 1.48 mmol). After stirring for 2 h at room temp, the mixture was evaporated to dryness, dissolved in CH$_3$CN (2.5 mL) and purified by preparative reverse phase HPLC to afford the desired thiol R009E (25.7 mg, 89%).
$^1$H NMR (CDCl$_3$) δ: 7.34~7.14 m, 6.99 d (J=8.3 Hz), 5.47 dd (J=8.6, 15.4 Hz), 5.34 dd (J=5.5, 15.4 Hz), 4.93 d (J=8.6 Hz), 4.51 m, 4.31 br m, 3.95 dd (J=3.5, 6.7 Hz), 3.52 dd (J=4.9, 9.2 Hz), 3.38 m, 3.12 dd (J=3.4, 13.9 Hz), 2.89 dd (J=6.8, 14.0 Hz), 2.69~2.67 m, 2.20~1.90 m, 2.12 s, 1.81 m, 1.66 m, 1.45 br s, 0.82 d (J=6.9 Hz), 0.80 d (J=8.5 Hz).

Example 97
Compound PE011

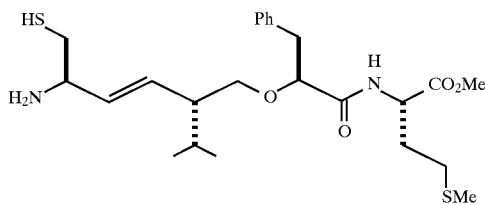

$^1$H NMR (CD$_3$OD) δ: 7.98 d (J=8.1 Hz), 7.18–7.28 m, 5.84 dd (J=9.5, 15.9 Hz), 5.47 dd (J=7.9, 15.5 Hz), 4.61 m, 4.02 dd (J=4.4, 7.0 Hz), 3.82 q (J=6.7 Hz), 3.72 5, 3.61 dd (J=4.7, 9.3 Hz), 3.45 dd (J=6.9, 9.2 Hz), 3.06 dd (J=4.2, 14.0 Hz), 2.79 dd (J=6.0, 14.1 Hz), 2.70 dd (J=6.3, 14.1 Hz), 2.26 m, 2.14 m, 2.03 s, 1.91 m, 1.73 o (J=6.7 Hz), 0.87 d (J=6.9 Hz), 0.84 d (J=6.7 Hz).

Example 98
Compound PE021

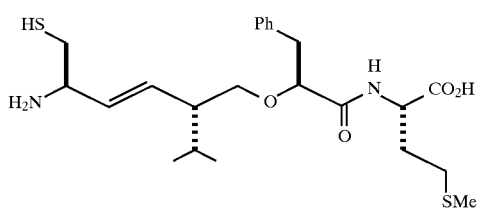

Thiol R009E (13 mg, 0.0208 mmol) was dried under vacuum, then TFA (0.76 mL) and Et$_3$SiH (0.24 mL) were added at 0° C. under argon. The mixture was stirred for 3 h, then evaporated to dryness, dissolved in of CH$_3$CN (2 mL) and purified by preparative reverse phase HPLC to furnish pure analog PE021 (10.6 mg, 84%).

$^1$H NMR (CD$_3$OD) δ: 7.85 d (J=8.1 Hz), 7.15–7.28 m, 5.85 dd (J=9.1, 15.4 Hz), 5.47 dd (J=7.7, 15.5 Hz), 4.56 dd (J=4.6, 8.2 Hz), 4.02 dd (J=4.1, 7.1 Hz), 3.81 q (J=3.81 Hz), 3.61 dd (J=4.6, 9.3 Hz), 3.47 dd(J=6.8, 9.3 Hz), 3.08 dd (J=4.0, 14.0 Hz), 2.92 dd (J=7.2, 14.1 Hz), 2.78 dd (J=6.0, 14.2 Hz), 2.69 dd (J=6.4, 14.2 Hz), 2.27 m, 2.03 s, 1.90 m, 1.73 o (J=6.8 Hz), 0.87 d (J=6.8 Hz), 0.84 d (J=6.7 Hz).

Example 99
Compound PE031

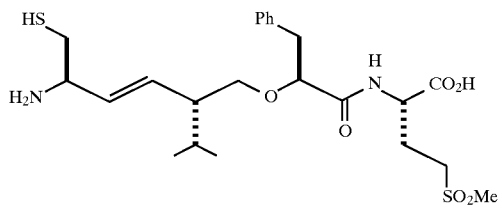

$^1$H NMR (CD$_3$OD) δ: 7.95 d (J=8.0 Hz), 7.20–7.30 m, 5.85 dd (J=9.2, 15.6 Hz), 5.47 dd (J=7.8, 15.4 Hz), 4.56 m, 4.04 dd (J=4.2, 7.0 Hz), 3.82 q (J=6.6 Hz), 3.63 dd (J=4.7, 9.3 Hz), 3.47 dd (J=7.0, 9.3 Hz), 3.09 dd (J=4.1, 14.1 Hz), 2.96 m, 2.93 s, 2.76–2.84 m, 2.70 dd (J=6.3, 14.1 Hz), 2.32 m, 2.11 m, 1.73 o (J=5.8 Hz), 0.87 d (J=6.9 Hz), 0.84 d (J=6.7 Hz).

Example 100
Compound P2041

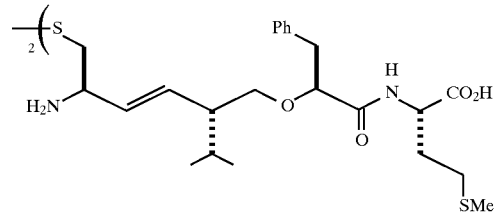

A small sample of PE201 (3.0 mg, 0.0051 mmol) in CD$_3$OD was left on the bench at room temp and oxidized by ambient oxygen. The solution was evaporated and purified by preparative reverse phase HPLC to afford analog PE041 (1.18 mg, 40%).

$^1$H NMR (CD$_3$OD) δ: 7.18–7.28 m, 5.94 dd (J=9.1, 15.5 Hz), 5.53 dd (J=7.6, 15.6 Hz), 4.51 dd (J=4.6, 8.0 Hz), 4.05 q (J=7.1 Hz), 3.98 dd (J=4.0, 7.2 Hz), 3.56 dd (J=4.4, 9.4 Hz), 3.50 dd (J=5.8, 9.3 Hz), 3.06 m, 2.91 dd (J=7.2, 14.0 Hz), 2.30 ddd (J=5.3, 8.6, 13.9 Hz), 2.22 dd (J=8.0, 13.2 Hz), 2.06 m, 2.03 s, 1.91 m, 1.76 o (J=6.8 Hz), 0.86 d (J=6.8 Hz), 0.81 d (J=6.7 Hz).

MS (FAB; M/Z, relative intensity): 937 (P+1, 100).

Example 101
Compound PE051

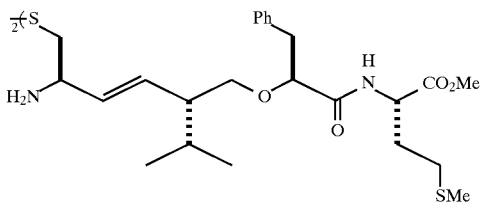

$^1$H NMR (CD$_3$OD) δ: 8.12 d (J=8.1 Hz), 7.19–7.29 m, 5.71 dd (J=9.2, 15.6 Hz), 5.45 dd (J=7.7, 15.6 Hz), 4.61 m, 4.00 dd (J=4.7, 7.3 Hz), 3.81 q (J=6.7 Hz), 3.71 s, 3.52 dd (J=7.7, 15.6 Hz), 3.44 dd (J=5.5, 9.1 Hz), 3.04 dd (J=4.5, 13.9 Hz), 2.91 dd (J=7.4, 13.9 Hz), 2.81 dd (J=7.0, 14.2 Hz), 2.76 dd (J=7.2, 13.2 Hz), 2.29 m, 2.04 s, 1.92 m, 1.77 o (J=6.5 Hz), 0.91 d (J=6.8 Hz), 0.81 d (J=6.8 Hz).

Example 102
Compound PE061

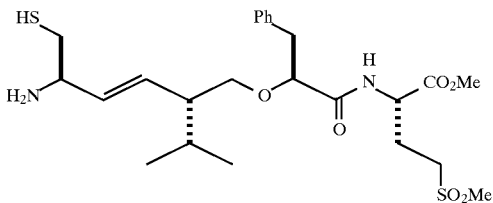

$^1$H NMR (CD$_3$OD) δ: 8.07 d (J=8.1 Hz), 7.20–7.30 m, 5.84 dd (J=9.2, 15.5 Hz), 5.47 dd (J=7.8, 15.5 Hz), 4.59 m, 4.04 dd (J=4.4, 7.0 Hz), 3.82 q (J=6.6 Hz), 3.74 s, 3.63 dd (J=4.8, 9.3 Hz), 3.46 dd (J=6.9, 9.2 Hz), 3.08 dd (J=4.3, 14.1 Hz), 2.93 s, 2.77–2.84 m, 2.71 dd (J=6.1, 14.0 Hz), 2.30 m, ~2.1 m, 1.74 o (J=6.7 Hz), 0.87 d (J=6.9 Hz), 0.84 d (J=6.8 Hz).

Example 103
Bromide R001T

Triphenylphosphine (2.30 g, 8.78 mmol) was added to a solution of carbon tetrabromide (2.96 g, 8.92 mmol) in CH$_2$Cl$_2$ (25 mL) at 5° C. The reaction was stirred for 10 min during which time it became dark yellow. A solution of alcohol R019D (1.281 g, 3.89 mmol) in CH$_2$Cl$_2$ (15 mL) was then added dropwise whereupon the reaction mixture became much lighter in color. The reaction was stirred at room temp for an additional 30 min, at which time TLC (eluting with 30% ethyl acetate:hexanes) indicated incomplete conversion to product. Additional quantities of triphenylphospine (1.08 g, 4.12 mmol) and carbon tetrabromide (1.41 g, 4.25 mmol) were added to ensure complete conversion and the color of the mixture returned to dark yellow. After stirring overnight, the reaction mixture was washed with water, dried over MgSO$_4$, filtered, concentrated in vacuo, and purified by FC, (eluting with 5% ethyl acetate:hexanes) to afford bromide R001T (1.438 mg, 92%) as a colorless oil.
$^1$H NMR (CDCl$_3$) δ: 5.69 dd (J=7.2, 15.2 Hz), 5.48 bs, 4.84 bs, 3.47 dd (J=5.3, 9.9 Hz), 3.40 dd (J=7.1, 9.9 Hz), 3.29 dd (J=6.0, 11.7 Hz), 2.60 d (J=11.7 Hz), 2.14 m, 1.82 m, 1.46 s, 0.92 d (J=6.7 Hz), 0.88 d (J=6.7 Hz).

Example 104
Thioacetate R002T

Potassium thioacetate (146 mg, 1.28 mmol) was added to a solution of bromide R001T (251 mg, 0.64 mmol) in DMF (1 mL). After stirring at room temp for 1 h, complete conversion to product was observed by TLC (eluting with 30% ethyl acetate:hexanes). The reaction was concentrated in vacuo and purified by FC (eluting with 5% ethyl acetate:hexanes), to afford thioacetate R002T (272 mg, 100%) as a yellow oil.
$^1$H NMR (CDCl$_3$) δ: 5.62 dd (J=6.8, 14.0 Hz), 5.38 bs, 4.8 bs, 3.26 dd (J=5.7, 12.0 Hz), 3.09 dd (J=5.3, 13.4 Hz), 2.78 dd (J=9.6, 13.9 Hz), 2.56 d (J=13.4 Hz), 2.30 s, 1.98 m, 1.76 s, 1.44 s, 0.91 d (J=6.7 Hz), 0.87 d (J=6.7 Hz).

Example 105
Thiol R003T

Flame-dried potassium carbonate (170 mg, 0.6 mmol) was added to a solution of thioacetate R002T (124 mg, 0.3 mmol) in methanol degassed with argon (2 mL) and the reaction was stirred at room temp for 10 min. The reaction was acidified to pH 2.0 with 0.1N HCl and extracted with ethyl acetate. TLC (eluting with 20% ethyl acetate-hexanes) exhibited no disulfide formation. The combined organic extracts were washed with brine, dried over Na$_2$SO$_4$ and concentrated in vacuo. The crude product was purified by FC (eluting with 2% ethyl acetate:hexanes) to give the free thiol R003T (79 mg, 72%) as a colorless oil.
$^1$H NMR (CDCl$_3$) δ: 5.66 dd (J=6.8, 15.3 Hz), 5.37 bm, 4.86 bs, 3.29 dd (J=6.1, 11.7 Hz), 2.60 d (J=11.4 Hz), 2.51 m, 1.95 m, 1.76 s, 1.45 s, 0.90 d (J=6.7 Hz), 0.86 d (J=6.7 Hz).

Example 106
Mesylate R008T

Triethylamine (0.616 ml, 4.42 mmol) was added to a solution of methyl 2-(S)-hydroxy-3-phenylpropionate (0.5 g, 2.76 mmol) in CH$_2$Cl$_2$ (10 mL) at 0° C., followed by dropwise addition of mesyl chloride (0.32 mL, 4.14 mmol). After 10 min, the reaction was warmed to room temp. TLC (eluting with 10% diethyl ether:CH$_2$Cl$_2$) indicated complete conversion to product. The reaction was partitioned between saturated aq NH$_4$Cl (100 mL) and CH$_2$Cl$_2$ (100 ml) and then extracted with CH$_2$Cl$_2$. The combined organic extracts were washed with brine, dried over Na$_2$SO$_4$ and concentrated in vacuo. The crude product was purified by FC (eluting with 10% ethyl acetate-hexanes) to afford desired mesylate R008T (614 mg, 86%) as a colorless oil.
$^1$H NMR (CDCl$_3$) δ: 7.2~7.4 m, 5.17 dd (J=4.2, 8.9 Hz), 3.80 s, 3.30 dd (J=4.1, 14.4 Hz), 3.13 dd (J=8.9, 14.4 Hz), 2.77 S.

Example 107
Methyl ester R004T

Flame-dried potassium carbonate (138 mg, 1.0 mmol) was added to a solution of thiol R003T (168 mg, 0.502 mmol) and mesylate R008T (260 mg, 1.0 mmol) in argon degassed methanol (5 mL) and the reaction was stirred at room temp for 0.5 h. TLC (eluting with 30% ethyl acetate:hexanes) showed complete disappearance of starting thiol R003T. The reaction was quenched by addition of 0.1N HCl solution and extracted with ethyl acetate. The combined organic extracts were washed with brine, dried over Na$_2$SO$_4$ and concentrated in vacuo. The resulting crude product was purified by FC (eluting with 5% ethyl acetate:hexanes), to afford methyl ester R004T (96 mg, 39%) as a colorless oil.
$^1$H NMR (CDCl$_3$) 6: 7.18–7.30 m, 5.63 dd (J=6.8, 15.2 Hz), 5.38 bs, 4.79 bs, 3.67 s, 3.66 s, 3.48 m, 3.25 m, 3.18 m, 2.94 m, 2.71 m, 2.57 m, 2.0 m, 1.58 s, 1.44 s, 0.85 m.

Example 108
Acid R005T

A solution of lithium hydroxide (45 mg, 1.89 mmol) in water (1 mL) was added to a solution of methyl ester R004T (96 mg, 0.189 mmol) in dioxane (1 mL) and the reaction was stirred vigorously overnight. TLC (eluting with 30% ethyl acetate:hexanes) indicated complete disappearance of starting methyl ester R004T. The reaction was acidified to pH 2.0 with 0.1N HCl and extracted with ethyl acetate. The combined organic extracts were dried over $Na_2SO_4$ and concentrated in vacuo to give acid R005T (98 mg, 100%) as a clear oil. The crude product was used in the next reaction directly without further purification.

$^1$H NMR (CDCl$_3$) δ: 7.20–7.30 m, 5.55 dd (J=6.3, 15.2 Hz), 5.35 bm, 4.87 bm, 3.45 m, 3.23 m, 3.18 m, 2.92 m, 2.68 m, 2.56 m, 1.97 bm, 1.76 s, 1.65 m, 1.45 s, 0.86 d (J=6.7Hz), 0.83 d (J=6.8 Hz).

Example 109
Methyl ester R006T

A solution of acid R005T (98 mg, 198 μmol), methionine methyl ester hydrochloride (48 mg, 238 μmol), EDC (57 mg, 297 μmol), HOBT (28 mg, 208 μmol) and NMM (23 μL, 208 μmol) in DMF (2 mL) was stirred at room temp overnight. The reaction mixture was diluted with ethyl acetate (50 mL), washed twice with water (50 mL), pH 7.2 phosphate buffer (50 mL) and brine (50 mL). The combined organic extracts were dried over $Na_2SO_4$ and concentrated in vacuo to afford methyl ester R006T (106 mg, 78%) as a colorless oil. The crude product was used in the next reaction directly without further purification.

$^1$H NMR (CDCl$_3$) δ: 7.18–7.30 m, 7.20 m, 5.6 m, 5.34 bm, 4.8 bs, 4.66 m, 3.73 s, 3.72 s, 3.55 m, 3.43 t (J=7 Hz), 3.23 m, 3.02 dd (J=7.5 Hz), 2.92 m, 2.66 td (J=13.5, 5 Hz), 2.54 m, 2.46 m, 2.32 m, 2.05 s, 2.03 s, 1.76 s, 1.44 s, 0.83 m.

Example 110
Disulfide R007T

Methoxycarbonylsulfenyl chloride (8.4 μL, 93.56 μmol) was added dropwise to a solution of thiazolidine R006T (61 mg, 95.47 μmol) in acetic acid (1 mL), DMF (0.1 mL) and water (0.05 mL) at 0° C. After stirring at 0° C. for 25 min and room temp for 5 min, reverse phase HPLC (eluting with 0.15% TFA in 5% acetonitrile-water to 0.15% TFA in acetonitrile over 30 min) indicated complete disappearance of starting material R006T. The reaction was concentrated in vacuo and purified by preparative reverse phase HPLC. Disulfide R007T (59 mg, 90%) was obtained as a colorless oil.

$^1$H NMR (CDCl$_3$) δ: 7.20–7.28 m, 5.44 m, 5.38 bm, 5.17 bm, 4.66 m, 4.39 bm, 3.90 s, 3.73 s, 3.55 q (J=6.5 Hz), 3.42 t (J=10 Hz), 3.26 m, 3.02 m, 2.91 q (J=8 Hz), 2.67 m, 2.49 m, 2.33 m, 2.05 s, 2.03 s, 1.93 m, 1.67 m, 1.45 s, 0.854 d (J=6.7 Hz), 0.847 d (J=6.7 Hz), 0.812 d (J=6.7 Hz), 0.802 d (J=6.8 Hz).

Example 111
Compound PT011

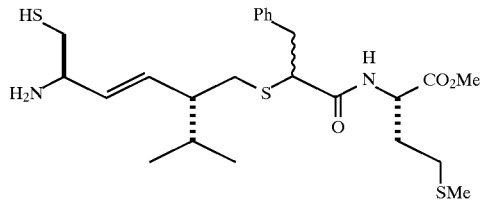

Tri-n-butylphosphine (0.107 mL, 0.428 mmol) was added to a solution of disulfide R007T (59 mg, 85.63 μmol) in THF (2 mL) and water (0.1 mL) and the reaction stirred at room temp for 0.5 h. Reverse phase HPLC (eluting with 0.15% TFA in 5% acetonitrile-water to 0.15% TFA in acetonitrile over 30 min) indicated complete conversion to product. The reaction was concentrated in vacuo and the crude product was dissolved in Et$_3$SiH (1 mL). TFA (3 mL) was added and the reaction stirred at room temp for 0.5 h. Reverse phase HPLC (eluting with 0.15% TFA in 5% acetonitrile-water to 0.15% TFA in acetonitrile over 30 min) indicated complete conversion to product. The reaction was concentrated in vacuo and purified by preparative reverse phase HPLC. After one chromatography, the final product still contained residual amounts of tri-n-butylphosphine and a second purification was necessary. Compound PT011 (8.1 mg, 15%) was obtained as a white solid of diastereomers after lyophilization from acetonitrile:H$_2$O (2:1).

$^1$H NMR (CD$_3$OD) δ: 7.17–7.28 m, 5.71 dd (J=9.2, 15.4 Hz), 5.43 dd (J=7.8, 15.7 Hz), 4.50 m, 3.83 q (J=6.8 Hz), 3.70 s, 3.64 s, 3.6 m, 3.16 dd (J=8.5, 13.8 Hz), 3.02 dd (J=10.6, 13.2 Hz), 2.65~2.95 m, 2.61 dd (J=9.4, 11.9 Hz), 2.47 m, 2.39 m, 2.1 m, 2.05 s, 1.97 s, 1.95 m, 1.75 m, 0.96 d (J=6.8 Hz), 0.94 d (J=6.9 Hz), 0.92 d (J=6.9 Hz), 0.89 d (J=6.8 Hz).

Example 112
Methyl ester R002M

5-Formylsalicylic acid (50.67 g, 305.0 mmol) was dissolved in MeOH (1.0 L) at room temp, concentrated H$_2$SO$_4$ (10 mL) was added, and the reaction solution was heated at reflux under nitrogen for 24 h. The solution was allowed to cool to room temp and was then concentrated to give a moist solid. To this solid was added H$_2$O (200 mL), MeOH (10 mL), and EtOAc (600 mL). The phases were separated, and the EtOAc phase was washed successively with H$_2$O (200 mL), saturated NaHCO$_3$ (3×200 mL), H$_2$O (200 mL), and saturated NaCl (2×200 mL). The EtOAc was then dried over MgSO$_4$, filtered through K$_2$CO$_3$, and concentrated to give a solid. This solid was crystallized from hot MeOH/H$_2$O (1:1, vol:vol, 1.0 L each) to give light tan needles which were collected by filtration, washed with MeOH/H$_2$O (1:1, vol:vol), and dried under vacuum to give 35.31 g (64%) of ester R002M as yellow-tan needles with a strong odor of wintergreen. (Piscopo, et al. *Farmaco.*, 1991, 46: 669–676). The following characteristic values were obtained by nuclear magnetic resonance spectroscopy:

$^1$H NMR (CDCl$_3$) δ: 11.38 s, 9.88 s, 8.38 d (J=2.2 Hz), 8.00 dd (J=2.1, 8.7 Hz), 7.10 d (J=8.6 Hz), and 4.10 s.

Example 113
Triflate R003N

Ester R002M (35.31 g, 196.0 mmol) was dissolved in dry pyridine (150 mL) at room temp under nitrogen, and the solution was cooled to 0° C. in an ice-water bath. Triflic anhydride (39.0 mL, 232 mmol) then was added over 15–20 minutes. The reaction solution was stirred at 0° C. for 3 h, the bath was removed, and the solution was stirred for an additional 3 h. The reaction solution was diluted with Et$_2$O (1000 mL) and washed successively with H$_2$O (2×200 mL), 10% HCl (3×150 mL), H$_2$O (150 mL), and saturated NaCl (2×150 mL). The combined aqueous phases were back-extracted with Et$_2$O (2×200 mL), and these Et$_2$O extracts were washed successively with 10% HCl (200 mL), H$_2$O (100 mL), and saturated NaCl (100 mL). The combined Et$_2$O phases were dried over MgSO$_4$/K$_2$CO$_3$, filtered, and concentrated to afford a brown liquid which was purified by FC (eluting with EtOAc/hexanes) to furnish 45.49 g (74%) of triflate R003M as a faintly yellow liquid which solidified on standing. The following characteristic values were obtained by nuclear magnetic resonance spectroscopy:

$^1$H NMR (CDCl$_3$) δ: 10.09 s, 8.61 d (J=2.2 Hz), 8.17 dd (J=2.3, 8.4 Hz), 7.50 d (J=8.5 Hz), and 4.02 s.

$^{19}F\{^1H\}$NMR (CDCl$_3$, CFCl$_3$=0.0 ppm) δ: −73.8 s.

Example 114
Aldehyde R004M

Triflate R003M (46.90 g, 150.2 mmol), benzeneboronic acid (40.42 g, 331.5 mmol), K$_2$CO$_3$ (31.34 g, 226.8 mmol), and Pd(CH$_2$Ph)(Cl)(PPh$_3$)$_2$ (3.4753 g, 4.5874 mmol) were dissolved in dry toluene (1000 mL) under argon at room temp. The resulting solution was heated to 100° C. for 4 h and then allowed to cool to room temp. The reaction mixture was filtered through CELITE®, and the CELITE® was rinsed with EtOAc. The filtrate was concentrated to approximately 100–200 mL, and 600 mL of EtOAc was added. This solution was washed successively with H$_2$O (200 mL), saturated NaHCO$_3$ (200 mL), 0.01N HCl (200 mL), pH 7.2 phosphate buffer (200 mL), and saturated NaCl (200 mL); dried over MgSO$_4$ with decolorizing carbon; filtered; and evaporated to give a yellow-orange sludge. Purification by FC (eluting with EtOAc/hexanes) gave 34.80 g (96%) of ester. R004M as a colorless, viscous liquid. The following characteristic values were obtained by nuclear magnetic resonance spectrosopy:

$^1$H NMR (CDCl$_3$) δ: 10.09 s, 8.33 d (J=1.8 Hz), 8.05 dd (J=1.9, 7.9 Hz), 7.57 d (J=7.9 Hz), 7.39–7.47 (m, 3H), 7.32–7.36 (m, 2H), and 3.70 (s, 3H).

Example 115
Compound R005M

A solution of 1.0M KO$^t$Bu/THF (20.0 mL, 20.0 mmol) was added via syringe to a suspension of (methoxymethyl)-triphenylphosphonium chloride (5.8071 g, 16.940 mmol) in THF (80 mL) cooled to 0° C. The resulting orange solution was stirred at 0° C. for 5 minutes, stirred at room temp for 1 h, and then cooled to 0° C. A solution of aldehyde R004M (3.2413 g, 13.491 mmol) in THF (10.0 mL) was added via syringe. The resulting yellow reaction solution was stirred overnight at room temp. The solution was diluted with EtOAc (100 mL); washed successively with pH 7.2 phosphate buffer (2×50 mL), H$_2$O (50 mL), and saturated NaCl (2×50 mL); dried over NaSO$_4$; filtered; and concentrated to give a liquid. Purification by FC gave 2.6216 g (72%) of intermediate R005M as a colorless liquid (1.4:1 trans/cis ratio). The following characteristic values were obtained by nuclear magnetic resonance spectroscopy:

$^1$H NMR (CDCl$_3$) δ: 7.96 d (J=1.9 Hz), 7.76 dd (J=1.9, 9.0 Hz), 7.67 d (J=1.9 Hz), 7.26–7.41 (m, 5H), 7.15 d (J=13.0 Hz), 6.22 d (J=7.0 Hz), 5.85 d (J=13.0 Hz), 5.27 d (J=7.0 Hz), 3.82 s (cis isomer), 3.72 s (trans isomer), 3.63 s, and 3.63 s.

Example 116
Compound R006M

Intermediate R005M, (0.582 g, 2.168 mmol) was dissolved in 1,4-dioxane (28 mL) and H$_2$O (6 mL), and p-toluenesulfonic acid (0.081 g, 0.4258 mmol) was added. The solution was heated to 65° C. for 12 h, then 75° C. for 5 h, and finally 85° C. for 8 h. The reaction solution was allowed to cool to room temp; diluted with EtOAc (150 mL); and washed successively with pH 7.2 phosphate buffer (50 mL), H$_2$O (50 mL), and saturated NaCl (50 mL). The solution then was dried over Na$_2$SO$_4$, filtered, and concentrated to give a viscous liquid which was purified by FC (eluting with EtOAc/hexanes) to give 0.376 g (68%) of intermediate R006M as a colorless, viscous liquid. The following characteristic values were obtained by nuclear magnetic resonance spectroscopy:

$^1$H NMR (CDCl$_3$ δ: 9.82 t (J=2.1 Hz), 7.70 s, 7.26–7.43 (m, 7H), 3.80 d (J=2.0 Hz), and 3.64 (s, 3H).

Example 117
Compound R008M

A solution of R007M (L-cysteine methyl ester hydrochloride) (25.7009 g, 149.7372 mmol) in H$_2$O (200 mL) was cooled to 0° C., and NaHCO$_3$ (13.01 g, 154.9 mmol) and K$_2$CO$_3$ (21.85 g, 158.1 mmol) were added. Phosgene (20 wt% in toluene, 105 mL, 203mmol) was then added dropwise. The resulting solution was stirred vigorously at 0 ° C. for approximately 2 h. The phases were separated, and the aqueous phase was evaporated to yield a white, granular solid. This solid was extracted with CH$_2$Cl$_2$ (4×100 mL). The combined CH$_2$Cl$_2$ extracts were dried over MgSO$_4$, filtered, and evaporated to give 17.6776 g (73%) of intermediate R008M as a colorless liquid which solidified on standing at −20° C. For an alternative synthesis, see E. Falb, et al., *Synth. Commun.*, 23(20) 2839-44 (1993). The following characteristic values were obtained by nuclear magnetic resonance spectroscopy:

$^1$H NMR (CDCl$_3$) δ: 6.35 br s, 4.45 ddd (J=0.7, 5.2, 8.2 Hz), 3.83 s, 3.72 dd (J=8.2, 11.4 Hz), and 3.64 dd (J=5.0, 11.4 Hz).

Example 118
Compound R009M

Intermediate ROOSM (17.6776 g, 109.68 mmol) was dissolved in dry EtOH (200 mL) at 0° C. NaBH$_4$ (6.0938 g, 161.08 mmol) was added portionwise under N$_2$. The resulting solution was stirred at 0° C. for 1.5 h and then allowed to warm to room temp. The reaction was quenched by addition of aqueous saturated NH$_4$Cl (30 mL) followed by vigorous stirring for 30 minutes. The mixture was filtered, and the filtrate was concentrated to give 17.6188 g (121%) of intermediate R009M as a syrup. The following characteristic values were obtained by nuclear magnetic resonance spectroscopy:

$^1$H NMR (CD$_3$OD) δ: 3.89–3.95 m, 3.49–3.63 m, and 3.28 dd (J=5.6, 11.1 Hz).

Example 119
Compound R010M

Intermediate R009M (17.62 g, 132.31 mmol) was combined with dry pyridine (55 mL) at 0° C., and TsCl (35.4 g, 185.7 mmol) was added portionwise under N$_2$. The resulting solution was stirred at 0° C. for 4 h and then at room temp for 2.5 h. The pyridine was removed under vacuum to leave a thick sludge which was diluted with CH$_2$Cl$_2$ (250 mL) and washed with aqueous 2N HCl (4×50 mL, 1×100 mL). The combined aqueous washings were back-extracted with CH$_2$Cl$_2$ (2×50 mL). The combined CH$_2$Cl$_2$ phases were washed with H$_2$O (100 mL) and saturated NaCl (100 mL), dried over MgSO$_4$, filtered, and evaporated to give a light brown solid. This solid was dissolved in CH$_2$Cl$_2$ (approximately 100 mL), and hexane (approximately 300 mL) was added. This solution was concentrated to approximately 100 mL, and a solid precipitated. The solid was collected by filtration, washed with hexane, and dried under vacuum to give 28.1163 g (74%, 90% from intermediate R008M) of intermediate R010M as a tan solid. The following characteristic values were obtained by nuclear magnetic resonance spectroscopy:

$^1$H NMR (CDCl$_3$) δ: 7.80 d (J=8.2 Hz), 7.39 d (J=8.2 Hz), 6.20 br S, 4.09–4.15 m, 3.98–4.03 m, 3.52–3.56 m, 3.13 d (J=4.3, 11.5 Hz), and 2.47 s.

Example 120
Compound R011M

Intermediate R010M (27.8043 g, 96.761 mmol), sodium iodide (64.0 g, 427 mmol), and NaHCO$_3$ (0.420 g, 4.99 mmol) were combined in acetone (400 mL). The resulting solution was heated at reflux under $N_2$ for 12 h. The solution was cooled to room temp and filtered. The filtrate was evaporated, and the residue was dissolved in EtOAc (300 mL) and $H_2o$ (100 mL). The phases were separated, and the EtOAc phase was washed with saturated $Na_2SO_3$ (2×75 mL) and saturated NaCl (100 mL). The combined aqueous phases were back-extracted with EtOAc (2×100 mL), and these EtOAc extracts were combined and washed with saturated NaCl (50 mL). The combined EtOAc phases were dried over $MgSO_4$ (with decolorizing carbon added), filtered, and evaporated to give a tan solid (22.8106 g, 97%), which was purified by FC (eluting with EtOAc/hexanes) to give 17.2634 g (74%) of intermediate R011M as a white, crystalline solid. The following characteristic values were obtained by nuclear magnetic resonance spectroscopy:
$^1$H NMR (CDCl$_3$) δ: 6.51 br s, 4.05–4.10 m, 3.61 dd (J=7.5, 11.4 Hz), and 3.24–3.37 m.

Example 121
Compound R012M

Intermediate R011M (16.2294 g, 66.7712 mmol), triphenylphosphine (88.27 g, 336.5 mmol), and DMF (30 mL) were combined and heated to 100° C. for 42 h. After cooling to room temp, the DMF was removed under vacuum to leave a semi-solid residue. This residue was repeatedly washed with $Et_2O$ to remove triphenylphosphine and then purified by FC (eluting with MeOH/CHCl$_3$) to give an off-white solid which was dried under vacuum at 80° C. to give 28.55 g (85%) of intermediate R012M as a tan solid. The following characteristic values were obtained by nuclear magnetic resonance spectroscopy and optical rotation:
$^1$H NMR (CD$_3$OD/D$_2$O) δ: 7.74–7.95 m, 4.81 br s, 4.39–4.46 m, 3.83–4.02 m, 3.49–3.54 m, and 2.98 dd (J=3.6, 8.1 Hz).
$^{13}$C{$^1$H} NMR (CD$_3$OD/D$_2$O) δ: 178.3, 137.5, 135.4 d (J=10.2 Hz), 132.5 d (J=12.7 Hz), 119.4 d (J=86.9 Hz), 52.0, 37.9 d (J=7.3 Hz), and 28.7 d (J=52.1 Hz).
$^{31}$P{$^1$H} NMR (CD$_3$OD/D$_2$O) δ: 24.0(s).
$[α]_{589}^{24}$=+18.39 (c=0.0255, MeOH).
$C_{22}H_{21}INOPS$
Anal. Calcd.:
C, 52.29; H, 4.19; I, 25.11; N, 2.77; S, 6.34.
Found:
C, 52.30; H, 4.20; I, 25.81; N, 2.81; S, 6.26.

Example 122
Compound R013M

Intermediate R012M (0.7720 g, 1.5277 mmol) was suspended in dry THF (7 mL) and cooled to approximately −42° C. To this solution, n-BuLi in hexane (0.600 mL, 1.52 mmol) was added via syringe, followed by LiHMDS in THF (1.52 mL, 1.52 mmol). The resulting red-orange solution was stirred at −42° C. for 1 h. A solution of intermediate R006M (0.3755 g, 1.4767 mmol) in THF (2 mL) was added via syringe, and the syringe was rinsed with THF (2×0.5 mL). The reaction mixture was stirred at −42° C. for 1 h and then at room temp for 1.75 h. The reaction was quenched with 5 mL of saturated NH$_4$Cl, and diluted with EtOAc (150 mL) and H$_2$O (50 mL). The phases were separated, and the EtOAc phase was washed successively with pH 7.2 phosphate buffer (50 mL) and saturated NaCl (2×50 mL), dried over MgSO$_4$, filtered, and concentrated to give an orange oil. Purification by FC (eluting with EtOAc/hexanes) gave 0.1589 g of intermediate R013M cis and 0.2341 g of intermediate R013M trans as colorless oils. The following characteristic values were obtained by nuclear magnetic resonance spectroscopy:

Compound R013M cis
$^1$H NMR (CDCl$_3$) δ: 7.60 s, 7.26–7.42 m, 5.92 br s, 5.87 dt (J=7.8, 10.5 Hz), 5.70 app t (J=9.9 Hz), 4.86 app q (J=8.2 Hz, 1H), 3.63 s, 3.50–3.60 m, 3.46 dd (J=7.0, 10.8 Hz), and 3.24 dd (J=8.5, 10.8 Hz).

Compound R013M trans
$^1$H NMR (CDCl$_3$) δ: 7.82 s, 7.18–7.41 m, 6.30 br s, 5.92 dt (J=7.2, 14.3 Hz), 5.59 dd (J=7.5, 15.2 Hz), 4.37 q (J=7.4 Hz), 3.61 s, 3.47 dd (J=7.3, 11.0 Hz), 3.44 br d (J=6.4 Hz), and 3.17 dd (J=7.5, 10.9 Hz).

Example 123
Compound R014M

Intermediate R013M trans (0.2341 g, 0.6623 mmol), BOC$_2$O (0.1765 g, 0.8087 mmol), and DMAP (0.0088 g, 0.072 mmol) were combined in THF (4.0 mL) and stirred for 3 h at room temp. The reaction solution was diluted with EtOAc (70 mL), washed successively with H$_2$O (2×25 mL) and saturated NaCl (2×25 mL), dried over MgSO$_4$, filtered, and evaporated to give an oil. Purification by FC (eluting with EtOAc/hexanes) gave 0.2352 g (78%) of intermediate R014M as a colorless oil. The following characteristic values were obtained by nuclear magnetic resonance spectroscopy:
$^1$H NMR (CDCl$_3$) δ: 7.62 d (J=1.6 Hz), 7.21–7.57 m, 5.94 dt (J=7.3, 14.6 Hz), 5.79 dd (J=6.9, 15.3 Hz), 4.97 t (J=7.2 Hz), 3.60–3.68 m, 3.63 s, 3.48 d (J=6.7 Hz), 2.92 dd (J=1.4, 11.0 Hz), and 1.43 s.

Example 124
Compound R015M

Intermediate R014M (1.8280 g, 4.030 mmol) was dissolved in MeOH, and CsHCO$_3$ (0.797 g, 4.110 mmol) and Cs$_2$CO$_3$ (0.2638 g, 0.810 mmol) were added. The resulting solution was stirred at room temp for 18 h. Additional Cs$_2$CO$_3$ (0.3787 g, 1.162 mmol) was added, and stirring was continued for 27 h. The reaction solution was diluted with EtOAc (350 mL); washed successively with 0.01N HCl (150 mL), H$_2$O (100 mL), pH 7.2 phosphate buffer (100 mL), and saturated NaCl (2×100 mL); dried over MgSO$_4$; filtered; and concentrated to give a viscous liquid. This liquid was diluted with THF (15 mL) and H$_2$O (5 mL), and then nBu$_3$P (2.0 mL, 8.027 mmol) was added. The resulting solution was stirred at room temp for approximately 2 h. The volatiles were removed under vacuum, and the residue was purified by FC (eluting with EtOAc/hexanes) to give 0.8216 g (48%) of intermediate R015M as an oily foam.
$^1$H NMR (CDCl$_3$) δ: 7.64 d (J=1.5 Hz), 7.26–7.41 m, 5.85 ddt (J=1.4, 6.8, 15.5 Hz), 5.47 dd (J=5.6, 15.4 Hz), 4.91 br s, 4.40 br s, 3.63 s, 3.47 d (J=6.7 Hz), 2.66–2.81 m, 1.44 s, and 1.35 dd (J=7.6, 9.4 Hz).

Example 125
Compound R016M

Intermediate R015M (0.3710 g, 0.8677 mmol) and triphenylmethanol (0.5655 g, 2.1722 mmol) were combined and dissolved in dry Et$_2$O at 0° C. BF$_3$·OEt$_2$ (0.215 mL, 1.748 mmol) was added, and the solution was stirred at 0° C. for 1 h. The solution was diluted with Et$_2$O (70 mL); washed successively with saturated NaHCO$_3$ (25 mL), H$_2$O (25 mL), and saturated NaCl (2×25 mL); dried over Na$_2$SO$_4$; filtered; and evaporated to give a solid. Purification by FC (eluting with EtOAc/hexanes) gave 0.4687 g (81%) of intermediate R016M as a solid/foam. The following characteristic values were obtained by nuclear magnetic resonance spectroscopy:
$^1$H NMR (CDCl$_3$) δ: 7.60 d (J=1.6 Hz), 7.18–7.42 m, 5.67 ddt (J=0.8, 7.2, 15.3 Hz), 5.37 dd (J=5.5, 15.3 Hz), 4.61 br s, 4.19 br s, 3.60 s, 3.39 d (J=6.7 Hz), 2.32–2.48 m, and 1.41 s.

Example 126

Compound R017M

Intermediate R016M (0.4687 g, 0.7007 mmol) was dissolved in MeOH (15.0 mL). LiOH (0.3985 g, 16.6388 mmol) and H$_2$O (3.0 mL) were added to give a milky solution. This solution was heated to 60° C. for 12 h and then allowed to cool to room temp. The reaction solution was acidified to approximately pH 2 with 1N KHSO$_4$ (25 mL), and diluted with EtOAc (70 mL) and H$_2$O (25 mL). The phases were separated, and the EtOAc phase was washed with saturated NaCl (2×30 mL), dried over MgSO$_4$, filtered, and evaporated to give an oil. Evaporation from CH$_2$Cl$_2$/hexanes gave 0.4300 g (93%) of intermediate R017M as a colorless solid. The following characteristic values were obtained by nuclear magnetic resonance spectroscopy:

$^1$H NMR (CD$_3$OD) δ: 7.56 s, 7.08–7.38 m, 5.58–5.66 m, 5.33 dd (J=6.6, 15.3 Hz, 4.80 br s, 3.94 br s, 3.37 d (J=6.7 Hz), 2.40 dd (J=7.7, 12.1 Hz), 2.17 dd (J=6.2, 12.2 Hz) and 1.41 s.

Example 127

Compound R018M

Intermediate R017M (0.0740 g, 0.1128 mmol), L-methionine PNB ester hydrochloride (0.0436 g, 0.1359 mmol), CMC (0,0823 g, 0.1943 mmol), HOBT (0.0156 g, 0.1154 mmol), NMM (0.013 mL, 0.1182 mmol), and DMF (1.0 mL) were combined, and the resulting solution was stirred at room temp for 72 h. The reaction solution was diluted with EtOAc (75 mL); washed successively with H$_2$O (2×25 mL), pH 7.2 phosphate buffer (25 mL), H$_2$O (25 mL), and saturated NaCl (2×25 mL); dried over MgSO$_4$; filtered; and evaporated to give an oil. Evaporation from CH$_2$Cl$_2$/hexanes gave 0.104 g (100%) of intermediate R018M as a solid. The following characteristic values were obtained by nuclear magnetic resonance spectroscopy:

$^1$H NMR (CD$_3$OD) δ: 8.22 d (J=8.7 Hz), 7.18–7.48 m, 5.87 d (J=7.6 Hz), 5.65 ddt (J=0.7, 7.2, 15.3 Hz), 5.38 dd (J=5.5, 15.2 Hz), 5.17 q (J=12.6 Hz), 4.63–4.73 m, 4.61 br s, 4.18 br s, 3.38 d (J=6.8 Hz), 2.30 - 2.48 m, 1.88–2.05 m, 1.96 s, 1.68–1.78 m, and 1.41 s.

Example 128

Compound R019M

Intermediate R018M (0.1040 g, 0.1128 mmol) was dissolved in THF (6.0 mL) at room temp, and a solution of Na$_2$S·9H$_2$O (0.5898 g, 2.4557 mmol) in H$_2$O (2.0 mL) was added. The resulting solution was stirred vigorously at room temp for 2.5 h, and the reaction was quenched with TFA (0.400 mL) and evaporated. The residue was dissolved in MeOH, filtered, and purified by RP HPLC to give 0.0633 g (71%) of intermediate R019M as a colorless solid. The following characteristic values were obtained by nuclear magnetic resonance spectroscopy:

$^1$H NMR (CD$_3$OD) δ: 7.17–7.44 m, 5.87 d (J=7.6 Hz), 5.61 dt (J=7.2, 14.3 Hz), 5.33 dd (J=6.5, 15.3 Hz), 4.46–4.50 m, 3.94 br s, 3.37 d (J=6.6 Hz), 2.40 dd (J=7.6, 12.22 Hz), 2.10–2.22 m, 1.92–2.06 m, 1.99 s, 1.72–1.82 m, and 1.40 s.

Example 129

Compound PM061

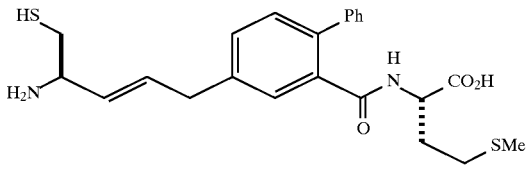

Intermediate R019M (0.0633 g, 0.08043 mmol) and triisopropylsilane (0.400 mL, 1.9525 mmol) (or triethylsilane) were combined, and TFA (1.5 mL) was added. After 2 h, the reaction mixture was evaporated to leave a solid residue which then was dissolved in MeOH, filtered, and purified by RP HPLC to give 0.371 g of compound PM061 (TFA salt). Compound PM061 was dissolved in MeOH (or CH$_3$CN) (10 mL), and 1N HCl (0.400 mL) was added. Evaporation and lyophilization from H$_2$O/CH$_3$CN gave 0.0273 g (71%) of compound PM061 (HCl salt) as a colorless solid. The following characteristic values were obtained by nuclear magnetic resonance spectroscopy:

1H NMR (CD$_3$OD) δ: 7.30–7.44 m, 6.14 dt (J=7.2, 14.4 Hz), 5.57 dd (J=8.0, 15.4 Hz), 4.46 br dd (J=3.5, 9.6 Hz), 3.87 q (J=6.8 Hz), 3.55 d (J=6.5 Hz), 2.86 dd (J=6.2, 14.2 Hz), 2.77 dd (J=6.4, 14.2 Hz), 2.04–2.12 m, 1.92–2.00 m, 1.99 s, and 1.70–1.80 m.

Example 130

Compound R020M

Intermediate R017M (0.0570 g, 0.0869 mmol), N,O-dimethylhydroxylamine hydrochloride (0.0178 g, 0.1825 mmol), CMC (0.0588 g, 0.1388 mmol), HOBT (0.0136 g, 0.1006 mmol), NMM (0.011 mL, 0.1000 mmol), and DMF (1.0 mL) were combined, and the resulting solution was stirred at room temp overnight (approximately 16 h). The reaction solution was diluted with EtOAc (70 mL); washed successively with H$_2$O (2×30 mL), pH 7.2 phosphate buffer (30 mL), H$_2$O (30 mL), and saturated NaCl (30 mL); dried over MgSO$_4$; filtered; and evaporated to give an oil. Purification by FC eluting with EtOAc/hexanes gave 0.0504 g (83%) of intermediate R020M as a white solid. (Note: this compound exhibits rotational isomerism in the $^1$H NMR at room temp.) The following characteristic values were obtained by nuclear magnetic resonance spectroscopy:

$^1$H NMR (CDCl$_3$) δ: 7.18–7.45 m, 5.64–5.72 m, 5.37 dd (J=5.4, 15.6 Hz), 4.60 br s, 4.18 br s, 3.49 br s, 3.38 d (J=6.7 Hz), 3.20 br s, 3.08 br s, 2.63 br s, 2.30–2.48 m, and 1.42 s.

Example 131

Compound R021M

Intermediate R020M (0.0504 g, 0.07211 mmol) was dissolved in Et$_2$O (4 mL) at 0° C. under argon, and LiAlH$_4$ (0.0062 g, 0.163 mmol) was added to the solution all at once. After 30 minutes, the reaction was quenched by the addition of MeOH (0.5 mL) at 0° C. To this solution, saturated aqueous sodium potassium tartrate solution (1 mL) was added, and the resulting mixture was stirred vigorously at room temp for 1 h. The mixture was filtered through CELITE®, and the filtrate was diluted with EtOAc (70 mL), washed successively with H$_2$O (2×25 mL) and saturated NaCl (2×25 mL), dried over Na$_2$SO$_4$, filtered, and concentrated to give 0.0420 g (91%) of intermediate R021M as an oil. The following characteristic values were obtained by nuclear magnetic resonance spectroscopy:

$^1$H NMR (CDCl$_3$) δ: 9.96 s, 7.81 d (J=1.7 Hz), 7.19–7.50 m, 5.67 dt (J=7.6, 15.2 Hz), 5.39 dd (J=5.6, 15.3 Hz), 4.61 br s, 4.18 br s, 3.42 d (J=6.8 Hz), 2.32–2.48 m, and 1.41 s.

Example 132
Compound R022M

Intermediate R021M (0.0420 g, 0.06564 mmol), L-methionine methyl ester hydrochloride (0.0436 g, 0.1359 mmol), EtOH (0.5 mL), and DMF (0.5 mL) were combined. To this solution was added Na(CN)BH$_3$ (0.0160 g, 0.2546 mmol), and the resulting mixture was stirred at room temp under argon for 6 h. The reaction solution was diluted with EtOAc (70 mL); washed successively with H$_2$O (2×30 mL), pH 7.2 phosphate buffer (30 mL), H$_2$O (30 mL), and saturated NaCl (2×30 mL); dried over MgSO$_4$; filtered; and evaporated to give an oil. Purification by FC (eluting with EtOAc/hexanes) gave 0.0400 g (77%) of intermediate R022M as a colorless oil. The following characteristic values were obtained by nuclear magnetic resonance spectroscopy:

$^1$H NMR (CDCl$_3$) δ: 7.09–7.43 m, 5.69 ddt (J=1.2, 7.0, 14.0 Hz), 5.39 dd (J=5.5, 15.3 Hz), 4.67 br s, 4.22 br s, 3.68 d (J=12.4 Hz), 3.60 s, 3.56 d (J=12.4 Hz), 3.37 d (J=6.9 Hz), 3.27–3.30 m, 2.45–2.58 m, 2.32–2.48 m, 2.04 s, 1.70–1.91 m, and 1.41 s.

Example 133
Compound R023M

Intermediate R022M (0.0221 g, 0.0281 mmol) was dissolved in MeOH (6.0 mL), 1,4-dioxane (1.5 mL), and H$_2$O (2.0 mL), and LiOH (0.0212 g, 0.8852 mmol) was added to the solution which then was stirred at room temp 24 h. The reaction solution was acidified with TFA (0.070 mL), and the volatiles were evaporated to give approximately 0.0249 g (100%) of intermediate R023M as a solid foam. The following characteristic values were obtained by nuclear magnetic resonance spectroscopy:

$^1$H NMR (CD$_3$OD) δ: 7.13–7.47 m, 5.58–5.62 m, 5.30 dd (J=6.4, 15.3 Hz), 4.15–4.26 m, 3.90–3.95 br m, 3.72–3.75 m, 2.35–2.47 m, 2.14–2.19 m, 1.92–2.05 m, 1.92 s, and 1.36 s.

Example 134
Compound PM121

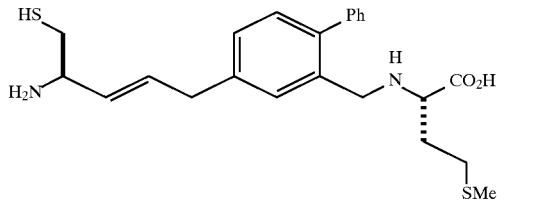

Intermediate R023M (approximately 0.0249 g, 0.02808 mmol) and triethylsilane (0.140 mL, 0.8765 mmol) were combined, and TFA (1.5 mL) was added. After 40 min, the reaction mixture was diluted with CH$_3$CN and purified by RP HPLC to give 0.0174 g of compound PM121 (2TFA salt) which then was dissolved in CH$_3$CN (10 mL) and to which 1N HCl (0.150 mL) was added. Evaporation, and lyophilization from H$_2$O/CH$_3$CN gave 0.0110 g (78%) of compound PM121 (2HCl salt) as a colorless solid. The following characteristic values were obtained by nuclear magnetic resonance spectroscopy:

$^1$H NMR (CD$_3$OD) δ: 7.59 s, 7.33–7.52 m, 6.17 dt (J=7.2, 14.4 Hz), 5.63 dd (J=8.0, 15.4 Hz), 4.34 br s, 3.87–3.92 m, 3.59 d (J=6.0 Hz), 2.89 dd (J=6.3, 14.2 Hz), 2.81 dd (J=6.4, 14.1 Hz), 2.46–2.56 m, 2.01–2.15 m, and 2.03 s.

Example 135
Compound R025M (Eq. 1)

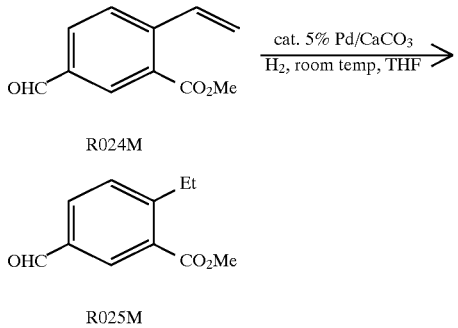

Intermediate R024M (0.465 g, 2.43 mmol) was dissolved in THF (28 mL) under argon, and 5% Pd/CaCO$_3$ (0.094 g, 0.94 mmol, ca. 0.05 mmol Pd) was added. The solution was stirred under H$_2$ at room temp for 30 min. The reaction solution was diluted with EtOAc and filtered through CELITE®. Evaporation gave 0.427 g of intermediate R025M (91%) as a colorless oil.

$^1$H NMR (CDCl$_3$) δ: 10.01 s, 8.37 d (J=1.8 Hz), 7.95 d (J=1.7, 8.0 Hz), 7.46 d (J=7.9 Hz), 3.94 s, 3.07 q (J=7.5 Hz), and 3.64 t (J=7.6 Hz).

Example 136
Compound R027M (Eq. 2)

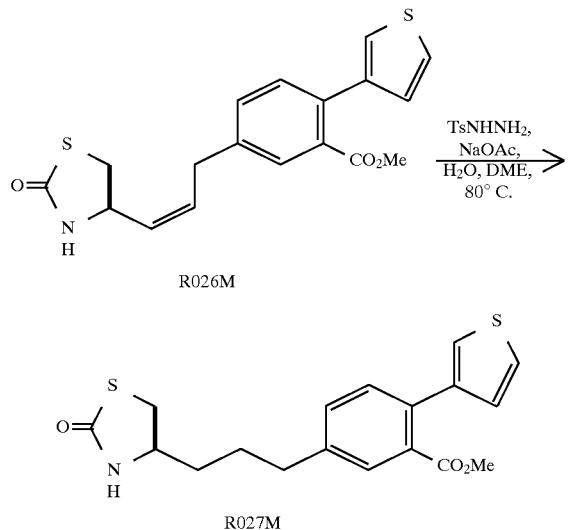

Intermediate R026M (0.827 g, 2.300 mmol) and TsNHNH$_2$ (6.521 g, 35.018 mmol) were dissolved in DME (60 mL) under N$_2$. The resulting solution was heated to 80° C., and a solution of NaOAc·3H$_2$O (6.293 g, 46.246 mmol) in H$_2$O (30 mL) was added dropwise over 6.5 h. The mixture was allowed to cool to room temp, diluted with H$_2$O (70 mL), and extracted with CH$_2$Cl$_2$ (3×60 mL). The combined CH$_2$Cl$_2$ layers were washed with saturated NaCl (50 mL), dried over Na$_2$SO$_4$, filtered, and concentrated to give an oil. Purification by FC (eluting with ethyl acetate/hexanes) gave 0.538 (65%) of R027M as a colorless oil.

$^1$H NMR (CDCl$_3$) δ: 7.56–7.58 m, 7.22–7.37 m, 7.07 dd (J=1.4, 4.9 Hz), 5.74 br s 1H, 3.85–3.91 m, 3.72 s, 3.47 dd (J=7.1, 10.9 Hz), 3.11 dd (J=7.2, 10.9 Hz), 2.72 br t (J=6.8 Hz), and 1.66–1.73 m.

Example 137
Iodoolefin R028M

Freshly distilled THF (10 mL) was added to CrCl$_2$ (300 mg, 2.43 mmol) under argon at 0° C. A solution of aldehyde R004M (97.3 mg, 0.405 mmol) and iodoform (322.5 mg, 0.819 mmol) in freshly distilled THF (5 mL) was added dropwise to the CrCl$_2$ solution and the resulting mixture stirred for 3.5 h at 0° C. TLC indicated complete loss of starting material and conversion to a new, less polar product. pH 7.0 phosphate buffer concentrate (10 mL) was added and the mixture allowed to warm to room temp. Saturated aq NH$_4$Cl (10 mL) was added and the mixture allowed to stir for 10 min. The resulting suspension was filtered through CELITE®, and the filter cake was washed well with several rinses of ethyl acetate. The resulting mixture was diluted further with ethyl acetate, shaken, and the aqueous phase decanted. The organic phase was washed further with water, dried with brine, dried with MgSO$_{41}$ filtered, and concentrated to a brown residue (200.3 mg). After purification by FC (eluting with 15% ethyl acetate-hexanes), pure iodoolefin R028M was obtained as a pale yellow solid (145.8 mg, 99%).
$^1$H NMR (CDCl$_3$) δ: 7.75 d (J=1.7 Hz), 7.48 d (J=15.1 Hz), 7.3–7.4 m, 6.98 d (J=15.0 Hz), 3.54 s.

Example 138
Alcohols R029M

CrCl$_2$ (240 mg, 1.953 mmol) was added all at once to a solution of aldehyde R015D (252.7 mg, 1.03 mmol) and iodoolefin R028M (119.1 mg, 0.327 mmol) stirring in DMSO (3 mL) in a dry box. Next, Ni(COD)$_2$ (3 mg, 0.011 mmol) was added to the above mixture and the resulting suspension stirred for 6 h at ambient temperature. The reaction was removed from the dry box and quenched by addition of saturated aq NH$_4$Cl (30 mL), CH$_2$Cl$_2$ (50 mL) was added, and the two phase mixture stirred at high speed for 15 min. The resulting two homogenous phases were transferred to a separatory funnel and separated. The aqueous layer was extracted twice with CH$_2$Cl$_2$ and the combined organic extracts washed twice with water, dried with MgSO$_4$, filtered, and concentrated to a yellow oil (345.5 mg). After purification by preparative TLC (eluting with 20% ethyl acetate:hexanes), the desired diastereomeric mixture of alcohols R029M was obtained as a transparent oil (67.2 mg, 47%). NMR data for alcohols R029M is complicated by extensive rotational isomerism on the NMR time scale.
$^1$H NMR (CDCl$_3$) δ: 7.83 d (J=9.3 Hz), 7.82 d (J=8.7 Hz), 7.54 d (J=8.0 Hz), 7.54 d (J=7.9 Hz), 7.26–7.39 m, 6.70 d (J=15.8 Hz), 6.67 (J=15.5 Hz), 6.40 b dd (J=2.3, 13.7 Hz), 6.33 dd (J=7.4, 15.9 Hz), 3.63 s, 3.18 m, 3.03 d (J=12.1 Hz), 2.81 d (J=12.2 Hz), 1.84 m, 1.80 s, 1.78 s, 1.52 s, 1.42 s.

Example 139
Trifluoroacetates R030M

An excess of triethylamine (0.189 mL, 1.356 mmol) and trifluoroacetic anhydride (0.096 mL, 0.680 mmol) was added to a solution of alcohols R029M (65.5 mg, 0.135 mmol) in freshly distilled CH$_2$Cl$_2$ (5.0 mL). After 20 min, the reaction mixture was diluted with ether, and washed twice with pH 7.0 phosphate buffer concentrate, once with 0.1N HCl, dried with MgSO$_4$, filtered, and concentrated to a crude oil (65.1 mg). Purification by preparative TLC (eluting with 20% ethyl acetate:hexanes) afforded impure trifluoroacetates R030M (R$_f$=0.54, 39.6 mg, 50%) along with recovered R029M (R$_f$=0.12, 18.1 mg, 27%).

Example 140
Ester R031M

A 2M solution of iPrMgCl in THF (0.332 mL, 0.663 mmol) was dripped slowly into a suspension of CuCN (29.7 mg, 0.332 mmol) in freshly distilled THF (3.0 mL) stirring rapidly at −40° C. After the addition had been completed the mixture was allowed to warm to 0° C. and stir for 40 min. The resulting dark solution was then recooled to −78° C. An impure solution of trifluoroacetates R030M containing some hydrolyzed alcohol (39 mg, ~0.067 mmol) in THF (1 mL) was added dropwise at −78° C. to the dark solution prepared above. The resulting mixture was stirred for 30 min and then quenched by addition of saturated aq NH$_4$Cl, (2 mL) warmed to room temp, NH$_4$OH (1 mL) and ether (20 mL). After stirring for 15 min, two homogeneous phases developed. The organic phase was decanted and washed with water, washed with pH 7.0 phosphate buffer concentrate, dried with MgSO$_4$, filtered, and concentrated to a clear oil (32.5 mg). After purification by preparative TLC (eluting with 10% ethyl acetate:hexanes, the pure ester R031M (9.9 mg, 29%) was obtained.

NMR data for alcohols R029M is complicated by extensive rotational isomerism on the NMR time scale. The rotational isomers (i, ii) are clearly distinguishable at −60° C.

$^1$H NMR (CDCl$_3$), −60° C. δ: 7.63 s & 7.57 s, 7.26–7.43 m, 5.87 dd (i, J=10.2, 14.7 Hz), 5.74 dd (i, J=8.9, 14.9 Hz), 5.68 dd (ii, J=7.2, 15.0 Hz), 5.61 dd (ii, J=9.6, 14.5 Hz), 4.83 (i, m), 4.67 (ii, m), 3.69 s, 3.66, 3.24 t (ii, J=6.0 Hz), 3.19 t (i, J=5.9 Hz), 2.85 t (ii, J=9.6 Hz), 2.79 t (i, J=10.1 Hz), 2.52 d (J=11.7 Hz), 1.92 br m, 1.82 s, 1.73 s, 1.70 s, 1.46 s, 1.35 s, 0.99 d (J=5.8 Hz), 0.90 d (J=5.9 Hz), 0.72 d (J=6.0 Hz), 0.68 d (J=6.0 Hz).

Example 141
Compound PM011

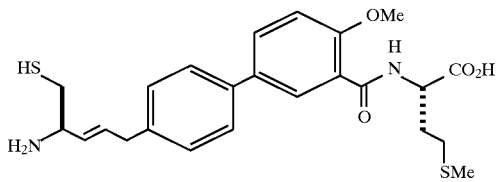

Compound PM011 was prepared in the same manner as that described in Scheme VIII, but 4-methoxybenzeneboronic acid and DMF were used in place of benzeneboronic acid and toluene in step 3, and L-methionine methyl ester hydrochloride was used in step 11 in place of L-methionine PNB ester hydrochloride, and the subsequent Na$_2$S·9H$_2$O step was replaced with a LiOH/MeOH/H$_2$O hydrolysis. The following characteristic values were obtained by nuclear magnetic resonance spectroscopy:

$^1$H NMR (CD$_3$OD) δ: 7.34–7.41 m, 6.98 d (J=8.7 Hz), 6.16 dt (J=7.1, 14.2 Hz), 5.59 dd (J=8.0, 15.4 Hz), 4.49–4.52 m, 3.89 q (J=7.0 Hz), 3.85 s, 3.56 d (J=6.9 Hz), 2.88 dd (J=6.2, 14.1 Hz), 2.79 dd (J=6.4, 14.2 Hz), 2.06–2.19 m, 1.94–2.01 m, 2.01 s, and 1.72–1.84 m.

Example 142

Compound PM012

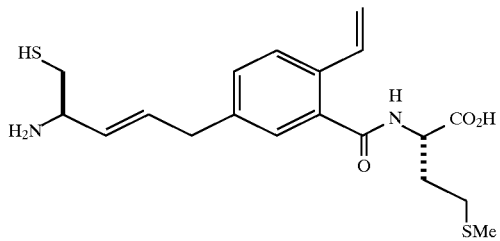

Compound PM012 was prepared in the same manner as that described in Scheme VIII, but tetravinyltin (with LiCl in DMF) was used in place of benzeneboronic acid in step 3, and L-methionine t-butyl ester hydrochloride was used in step 11 in place of L-methionine PNB ester hydrochloride, and the subsequent $Na_2S \cdot 9H_2O$ step was omitted.

$^1$H NMR (CD$_3$OD) δ: 8.66 d (J=7.6 Hz), 7.61–7.64 m, 7.14–7.36 m, 7.01 dd (J=11.0, 17.5 Hz), 6.07–6.12 m, 5.77 d (J=17.4 Hz), 5.49–5.55 m, 5.29 d (J=11.7 Hz), 4.71–4.75 m, 3.85 q (J=7.3 Hz), 3.49–3.59 m, 2.51–2.90 m, 2.13–2.24 m, 2.11 s, and 1.98–2.11 m.

Example 143

Compound PM021

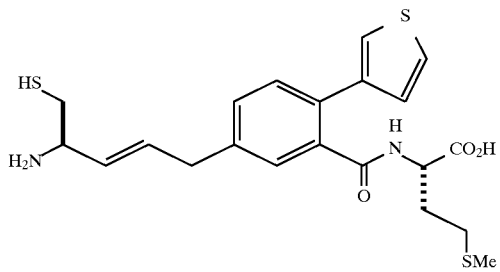

Compound PM021 was prepared in the same manner as that described in Scheme VIII, but 3-thiopheneboronic acid was used in place of benzeneboronic acid in step 3, and L-methionine t-butyl ester hydrochloride was used in step 11 in place of L-methionine PNB ester hydorchloride, and the subsequent $Na_2S \cdot 9H_2O$ step was omitted. The following chracteristic values were obtained by nuclear magnetic resonance spectorscopy:

$^1$H NMR (CD$_3$OD) δ: 7.45–7.53 m, 7.37–7.39 m, 7.24 d (J=4.8 Hz), 6.15 dt (J=7.2, 14.4 Hz), 5.58 dd (J=8.0, 15.4 Hz), 4.59 br dd (J=4.0, 9.5 Hz), 3.88 q (J=6.8 J Hz), 3.56 d (J=6.5 Hz), 2.87 dd (J=6.0, 13.8 Hz), 2.79 dd (J=6.2, 14.1 Hz), 2.29–2.35 m, 2.18–2.25 m, 2.03–2.12 m, 2.06 s, and 1.82–1.91 m.

Example 144

Compound PM022

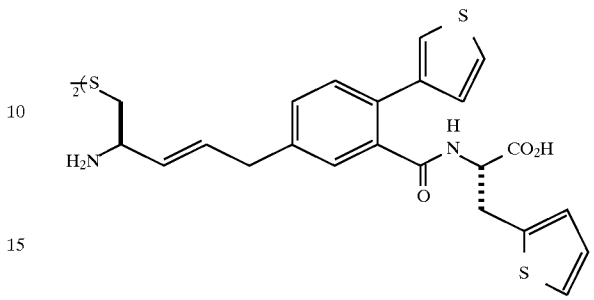

Compound PM022 was prepared from compound PM152 by exposure to air and was purified by RP HPLC.

$^1$H NMR (CD$_3$OD) δ: 7.21–7.43 m, 7.11 dd (J=1.3, 4.0 Hz), 6.94 dd (J=3.4, 5.1 Hz), 6.82 d (J=2.9 Hz), 5.99 dt (J=7.2, 14.4 Hz), 5.48 dd (J=8.3, 15.4 Hz), 4.75 dd (J=4.7, 9.1 Hz), 3.99 q (J=7.3 Hz), 3.44 d (J=5.7 Hz), 3.39–3.50 m, 3.22 dd (J=9.2, 14.9 Hz), and 3.01 d (J=6.5 Hz).

Example 145

Compound PM031

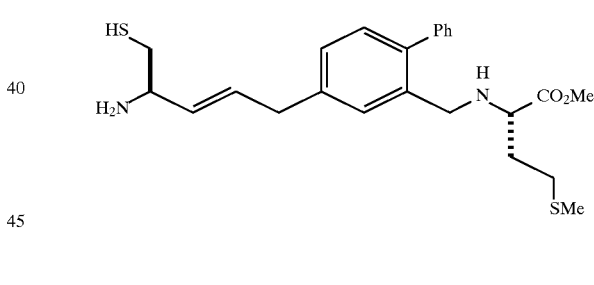

Intermediate R022M (approximately 0.0176 g, 0.02236 mmol) and triethylsilane (0.050 mL, 0.3130 mmol) were combined, and TFA (1.0 mL) was added at 0° C. After approximately 2 h, the reaction mixture was diluted with CH$_3$CN and purified by RP HPLC to give 0.0156 g of compound PM031 (2TFA salt). Compound PM031 was dissolved in CH$_3$CN (10 mL), and 1N HCl (0.150 mL) was added to the solution. Evaporation and lyophilization from H$_2$O/CH$_3$CN gave 0.0114 g (98%) of compound PM031 (2HCl salt) as a colorless solid. The following characteristic values were obtained by nuclear magnetic resonance spectroscopy:

$^1$H NMR (CD$_3$OD) δ: 7.69 s, 7.34–7.65 m, 6.20 dt, (J=7.3, 14.6 Hz), 5.66 dd (J=8.0, 15.4 Hz), 4.33 m, 3.96 t (J=6.3 Hz), 3.87 q (J=6.9 Hz), 3.64 s, 3.57 d (J=6.7 Hz), 2.86 dd (J=6.3, 14.1 Hz), 2.78 dd (J =6.4, 14.1 Hz), 2.41–2.51 m, 2.05 q (J=6.9 Hz), and 1.99 S.

Example 146

Compound PM032

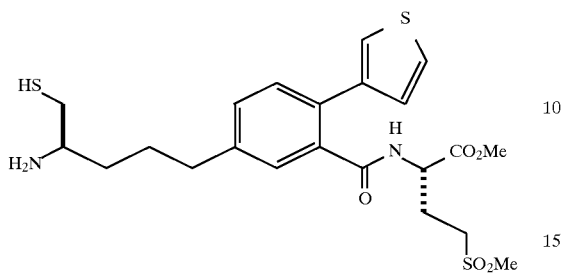

Compound PM032 was prepared in the same manner as that described in Scheme VIII, but 3-thiopheneboronic acid was used in place of benzeneboronic acid in step 3, and L-methionine sulfone methyl ester hydrochloride was used in Step 11 in place of L-methionine PNB ester hydrochloride, and the subsequent $Na_2S \cdot 9H_2O$ step was omitted. Furthermore, between steps 6 and 7 in Scheme VIII, a diimide hydrogenation step was inserted (see Equation 2).

$^1$H NMR ($CD_3OD$) δ: 7.34–7.48 m, 7.20 dd (J=1.4, 4.9 Hz), 4.58 dd (J=4.8, 9.4, 1H), 3.74 s, 2.93 s, 2.86–2.99 m, 2.68–2.81 m, 2.25–2.34 m, 1.98–2.14 m, and 1.68–1.76 m.

Example 147

Compound PM041

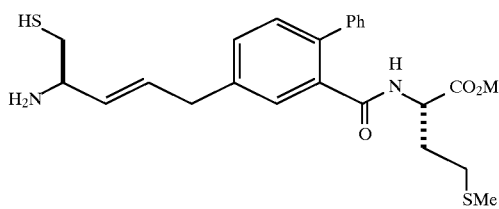

Compound PM041 was prepared in the same manner as that described in Scheme VIII, but R017M was combined with L-methionine methyl ester hydrochloride instead of L-methionine PNB ester hydrochloride, and the subsequent $Na_2S \cdot 9H_2O$ step was omitted. The following characteristic values were obtained by nuclear magnetic resonance spectroscopy:

$^1$H NMR ($CD_3OD$) δ: 8.40 d, (J=7.7 Hz), 7.32–7.42 m, 6.14 dt (J=7.2, 14.5 Hz), 5.57 dd (J=8.1, 15.4 Hz), 4.47–4.53 m, 3.87 app q (J=6.9 Hz), 3.69 s, 3.56 d (J=6.6 Hz), 2.86 dd (J=6.2, 14.2 Hz), 2.77 dd (J=6.4, 14.2 Hz), 2.05–2.15 m, 1.88–2.00 m, 1.98 s, and 1.68–180 m.

Example 148

Compound PM042

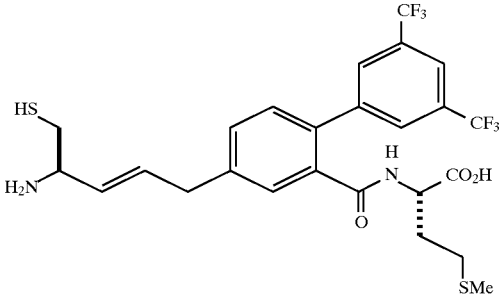

Compound PM042 was prepared in the same manner as that described in Scheme VIII but 3,5-bis(trifluoromethyl)-benzeneboronic acid was used in place of benzeneboronic acid in step 3, and L-methionine t-butyl ester hydrochloride was used in step 11 in place of L-methionine PNB ester hydrochloride, and the subsequent $Na_2S \cdot 9H_2O$ step was omitted.

$^1$H NMR ($CD_3OD$) δ: 8.59 d (J=7.5 Hz), 7.93 s, 7.42–7.48 m, 6.14 dt (J=7.2, 14.4 Hz, 5.58 dd (J=8.0, 15.4 Hz), 4.47–4.51 m, 3.87 q (J=6.9 Hz), 3.59 d (J=6.6 Hz), 2.85 dd (J=6.1, 14.0 Hz), 2.77 dd (J=6.3, 14.2 Hz), 2.06–2.24 m, 1.99 s, 1.95–2.05 m. and 1.76–1.86 m.

$^{19}$F{$^1$H} NMR ($CDCl_3$, $CFCl_3$=0.0 ppm) δ: –62.5 (s).

Example 149

Compound PM051

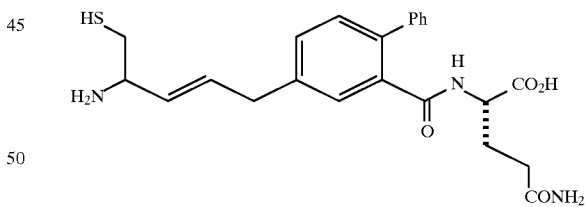

Compound PM051 was prepared in the same manner as that described in Scheme VIII, but R017M was combined with L-glutamine t-butyl ester hydrochloride instead of L-methionine PNB ester hydrochloride, and the subsequent $Na_2S \cdot 9H_2O$ step was omitted. The following characteristic values were obtained by nuclear magnetic resonance spectroscopy:

$^1$H NMR ($CD_3OD$) δ: 7.30–7.43 m, 6.13 dt (J=7.2, 14.4 Hz), 5.57 dd (J=8.1, 15.4 Hz), 4.32–4.35 m, 3.86 app q (J=6.8 Hz), 3.55 d (J=6.6 Hz), 2.85 dd (J=6.3, 14.1 Hz), 2.77 dd (J=6.3, 14.2 Hz), and 1.77–2.06 m.

Example 150
Compound PM052

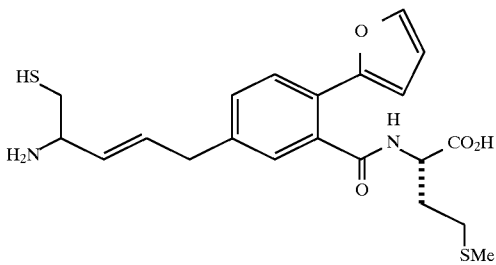

Compound PM052 was prepared in the same manner as that described in Scheme VIII, but 2-furanboronic acid was used in place of benzeneboronic acid in step 3, and L-methionine t-butyl ester hydrochloride was used in step 11 in place of L-methionine PNB ester hydrochloride, and the subsequent Na$_2$S·9H$_2$O step was omitted. 2-Furanboronic acid was obtained according to Thompson et al., *J. Org. Chem.*, 49:5237–5243 (1984).

$^1$H NMR (CD$_3$OD) δ: 8.72 d (J=7.7 Hz), 7.68 d (J=8.0 Hz), 7.55 d (J=1.5 Hz), 7.29–7.37 m, 6.73 d (J=3.3 Hz), 6.48 dd (J=1.8, 3.3 Hz), 6.11 dt (J=7.1, 14.2 Hz), 5.54 dd (J=8.2, 15.4 Hz), 4.72–4.75 m, 3.85 q (J=6.8 Hz), 3.52 d (J=6.5 Hz), 2.85 dd (J=6.2, 14.2 Hz), 2.75 dd (J=6.5, 14.3 Hz), 2.41–2.63 m, 2.16–2.21 m, 2.09 s, and 1.94–2.08 m.

Example 151
Compound PM062

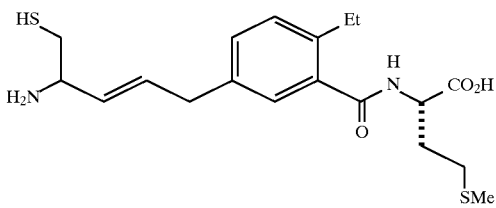

Compound PM062 was prepared in the same manner as that described for compound PM212 in Example 175, but step 12, Scheme VIII (Na$_2$S·9H$_2$O, omitted in the preparation of PM212), was replaced by a LiOH/MeOH/H$_2$O hydrolysis.

$^1$H NMR (CD$_3$OD) δ: 7.26–7.33 m, 6.12 dt (J=7.1, 14.2 Hz), 5.53 dd (J=8.1, 15.4 Hz), 4.74–4.76 m, 3.86 q (J=6.7 Hz), 3.50 d (J=6.5 Hz), 2.57–2.98 m, 2.21–2.30 m, 2.14 s, 2.01–2.14 m, and 1.22 t (J=7.6 Hz).

Example 152
Compound PM071

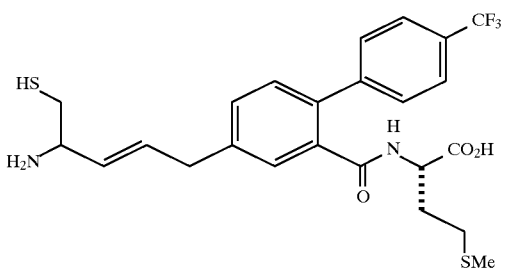

Compound PM071 was prepared in the same manner as that described in Scheme VIII, but 4-trifluoromethylbenzeneboronic acid was used in place of benzeneboronic acid in step 3, and L-methionine t-butyl ester hydrochloride was used in step 11 in place of L-methionine PNB ester hydrochloride, and the subsequent Na$_2$S·9H$_2$O step was omitted. The following characteristic values were obtained by nuclear magnetic resonance spectroscopy:

$^1$H NMR (CD$_3$OD) δ: 7.58–7.68 m, 7.38–7.45 m, 6.14 dt (J=7.1, 14.2 Hz), 5.57 dd (J=7.7, 15.0 Hz), 4.50–4.52 m, 3.82–3.90 m, 3.57 d (J=6.4 Hz), 2.85 dd (J=5.9, 13.9 Hz), 2.76 dd (J=6.1, 14.1 Hz), 2.18–2.30 m, 1.94–2.12 m, 2.00 s, and 1.78–1.86 m.

$^{19}$F{$^1$H}NMR (CDCl$_3$, CFCl$_3$=0.0 ppm) δ: −62.3 s.

Example 153
Compound PM072

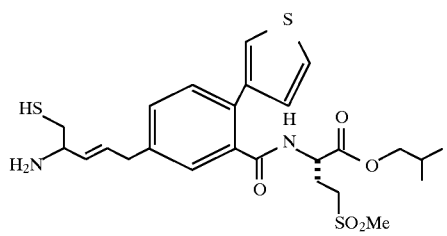

Compound PM072 was prepared in the same manner as that described in Scheme VIII, but 3-thiopheneboronic acid was used in place of benzeneboronic acid in step 3, and L-methioninesulfone isobutyl ester hydrochloride was used in step 11 in place of L-methionine PNB ester hydrochloride, and the subsequent Na$_2$S·9H$_2$O step was omitted.

$^1$H NMR (CD$_3$OD) δ: 8.65 d (J=7.8 Hz), 7.36–7.56 m, 7.24 d (J=1.3, 4.9 Hz), 6.15 dt (J=7.2, 14.5 Hz), 5.59 dd (J=8.0, 15.4 Hz), 4.58–4.63 m, 3.98 d (J=6.6 Hz), 3.89 q (J=6.9 Hz), 3.57 d (J=6.5 Hz), 2.95 s, 2.70–3.00 m, 2.29–2.37 m, 1.96–2.10 m, and 0.99 d (J=6.7 Hz).

Example 154
Compound PM081

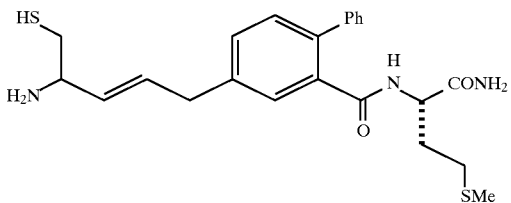

Therapeutic compound PM081 was prepared in the same manner as that described in Scheme VIII, but L-methionine amide hydrochloride was used in step 11 in place of L-methionine PNB ester hydrochloride, and the subsequent Na$_2$S·9H$_2$O step was omitted. The following characteristic values were obtained by nuclear magnetic resonance spectroscopy:

$^1$H NMR (CD$_3$OD) δ: 7.34–7.44 m, 6.16 dt (J=7.2, 14.3 Hz), 5.60 dd (J=8.0, 15.4 Hz), 4.40–4.44 m, 3.89 q (J=6.8 Hz), 3.58 d (J=7.0 Hz), 2.88 dd (J=6.3, 14.2 Hz), 2.79 dd (J=6.4, 14.2 Hz), 2.00–2.14 m, 2.03 s, 1.85–1.94 m, and 1.66–1.75 m.

Example 155

Compound PM082

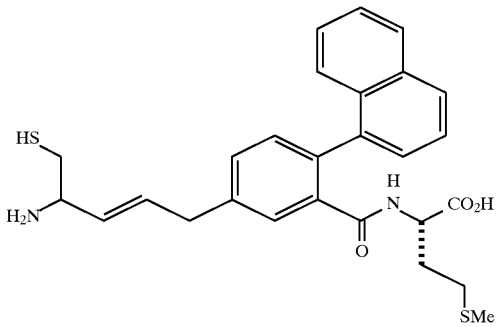

Compound PM082 was prepared in the same manner as that described in Scheme VIII, but 1-naphthaleneboronic acid was used in place of benzeneboronic acid in step 3, and L-methionine t-butyl ester hydrochloride was used in step 11 in place of L-methionine PNB ester hydrochloride, and the subsequent $Na_2S \cdot 9H_2O$ step was omitted. (Note: this compound exhibits rotational isomerism in the $^1H$ NMR at room temp.)

$^1H$ NMR ($CD_3OD$) δ: 7.85–7.92 m, 7.19–7.64 m, 6.19 dt (J=7.2, 14.5 Hz), 5.60–5.67 m, 4.24 dd (J=3.6, 8.9 Hz), 4.18 dd (J=4.1, 8.7 Hz), 3.87–3.91 m, 3.62 d (J=6.6 Hz), 2.88 dd (J=6.3, 13.8 Hz), 2.79 dd (J=6.3, 14.1 Hz), 1.81 s, 1.76 s, and 1.19–1.81 m.

Example 156

Compound PM091

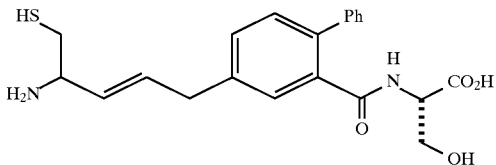

Compound PM091 was prepared in the same manner as that described in Scheme VIII, but R017M was combined with L-serine t-butyl ester t-butyl ether hydrochloride instead of L-methionine PNB ester hydrochloride, and the subsequent $Na_2S \cdot 9H_2O$ step was omitted. The following characteristic values were obtained by nuclear magnetic resonance spectroscopy:

$^1H$ NMR ($CD_3OD$) δ: 7.33–7.60 m, 6.18 dt (J=7.2, 14.5 Hz), 5.56 dd (J=8.0, 15.4 Hz), 4.49–4.51 m, 3.90 app q (J=6.9 Hz), 3.84 dd (J=4.8, 11.1 Hz), 3.67 dd (J=4.1, 11.1 Hz), 3.59 d (J=6.5 Hz), 2.89 dd (J=6.1, 14.2 Hz), and 2.79 dd (J=6.4, 14.2 Hz).

Example 157

Compound PM092

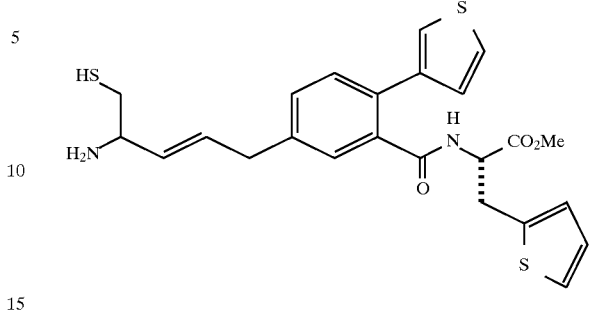

Compound PM092 was prepared in the same manner as that described in Scheme VIII, but 3-thiopheneboronic acid was used in place of benzeneboronic acid in step 3, L-3-(2-thienyl)-alanine methyl ester hydrochloride was used in step 11 in place of L-methionine PNB ester hydrochloride, and the subsequent $Na_2S \cdot 9H_2O$ step was omitted.

$^1H$ NMR ($CD_3OD$) δ: 7.30–7.47 m, 7.24 m, 7.13 dd (J=1.2, 4.9 Hz), 6.97 dd (J=3.5, 5.1 Hz), 6.83 m, 6.14 dt (J=7.2, 14.5 Hz), 5.56 dd (J=7.7, 15.4 Hz), 4.79–4.82 m, 3.88 q (J=6.7 Hz), 3.76 s, 3.54 d (J=6.2 Hz), 3.19–3.42 m, 2.88 dd (J=6.1, 14.1 Hz), and 2.78 dd (J=6.3, 14.2 Hz).

Example 158

Compound PM101

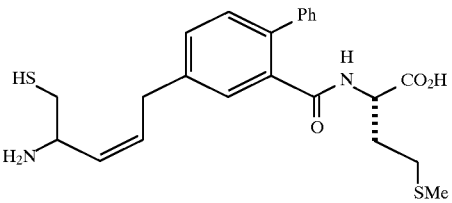

Compound PM101 was prepared according to Scheme VIII with the substitution of R013M cis for R013M trans. The following characteristic values were obtained by nuclear magnetic resonance spectroscopy:

$^1H$ NMR ($CD_3OD$) δ: 7.30–7.44 m, 6.08 dt (J=5.3, 15.3 Hz), 5.50 app tt (J=1.3, 10.3 Hz), 4.45–4.49 m, 4.35 dt (J=4.5, 13.0 Hz), 3.64 app d (J=7.5 Hz), 2.74–2.86 m, 2.04–2.12 m, 1.92–2.00 m, 1.99 s, and 1.68–1.80 m.

Example 159

Compound PM102

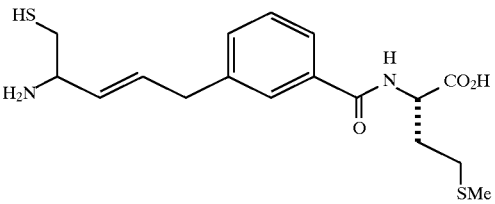

Compound PM102 was prepared in the same manner as that described in Scheme VIII, but 3-carboxybenzaldehyde was used in place of 5-formylsalicylic acid in step 1, steps 2 and 3 were omitted, L-methionine t-butyl ester hydrochloride was used in step 11 in place of L-methionine PNB ester hydrochloride, and the subsequent $Na_2S \cdot 9H_2O$ step was omitted.

¹H NMR (CD₃OD) δ: 7.73–7.76 m, 7.44–7.47 m, 6.15 dt (J=7.3, 14.6 Hz), 5.57 dd (J=8.0, 15.4 Hz), 4.80 br dd (J=4.6, 9.5 Hz), 3.89 q (J=6.8 Hz, 1H), 3.57 d (J=6.7 Hz), 2.88 dd (J=6.1, 14.2 Hz), 2.79 dd (J=6.3, 14.1 Hz), 2.53–2.74 m, 2.22–2.33 m, 2.13 s, and 2.03–2.20 m.

Example 160

Compound PM111

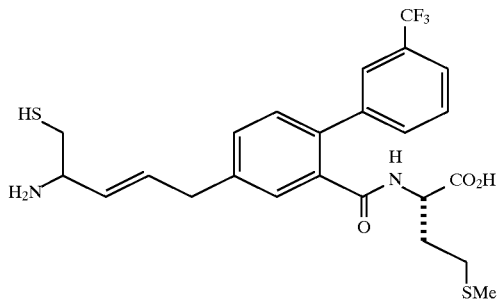

Compound PM111 was prepared in the same manner as that described in Scheme VIII, but 3-trifluoromethylbenzeneboronic acid was used in place of benzeneboronic acid in step 3, and L-methionine methyl ester hydrochloride was used in step 11 in place of L-methionine PNB ester hydrochloride, and the subsequent Na₂S·9H₂O step was replaced with a LiOH/MeOH/H₂O hydrolysis. The following characteristic values were obtained by nuclear magnetic resonance spectroscopy:

¹H NMR (CD₃OD) δ: 7.57–7.68 m, 7.39–7.45 m, 6.14 dt (J=7.7, 15.3 Hz), 5.58 dd (J=8.0, 15.4 Hz), 4.46–4.48 m, 3.87 q (J=7.4 Hz), 3.58 d (J=6.5 Hz), 2.86 dd (J=6.2, 14.2 Hz), 2.77 dd (J=6.4, 14.2 Hz), 1.92–2.18 m, 1.99 s, and 1.72–1.82 m.

Example 161

Compound PM112

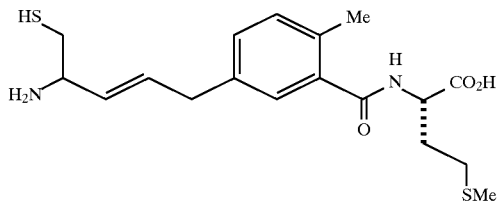

Compound PM112 was prepared in the same manner as that described in Scheme VIII, but tetramethyltin (with LiCl in DMF) was used in place of benzeneboronic acid in step 3, and L-methionine t-butyl ester hydrochloride was used in step 11 in place of L-methionine PNB ester hydrochloride, and the subsequent Na₂S·9H₂O step was omitted.

¹H NMR (CD₃OD) δ: 8.58 d (J=7.7 Hz), 7.18–7.28 m, 6.09 dt (J=7.2, 14.4 Hz), 5.50 dd (J=8.0, 15.4 Hz), 4.73 br dd (J=4.5, 9.6 Hz), 3.84 q (J=6.8 Hz), 3.47 d, (J=6.4 Hz), 2.83 dd (J=6.2, 14.2 Hz), 2.74 dd (J=6.4, 14.1 Hz), 2.48–2.69 m, 2.38 s, 2.18–2.28 m, 2.11 s, and 1.99–2.10 m.

Example 162

Compound PM122

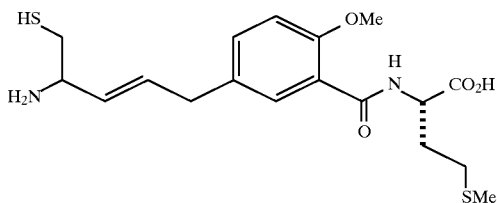

Compound PM122 was prepared in the same manner as that described in Scheme VIII, but step 2 was replaced with a dimethyl sulfate alkylation step, step 3 was omitted, L-methionine t-butyl ester hydrochloride was used in step 11 in place of L-methionine PNB ester hydrochloride, and the subsequent Na₂S·9H₂O step was omitted.

¹H NMR (CD₃OD) δ: 7.80 d (J=2.2 Hz), 7.41 dd (J=2.1, 8.4 Hz), 7.15 d (J=8.4 Hz), 6.12 dt (J=7.2, 14.4 Hz), 5.53 dd (J=8.0, 15.4 Hz), 4.81 dd (J=4.9, 7.6 Hz), 4.01 s, 3.85–3.96 m, 3.48 d (J=6.6 Hz), 2.87 dd (J=6.1, 14.1 Hz), 2.77 dd (J=6.4, 14.1 Hz), 2.58–2.63 m, 2.25–2.32 m, 2.12 s, and 2.10–2.20 m.

Example 163

Compound PM131

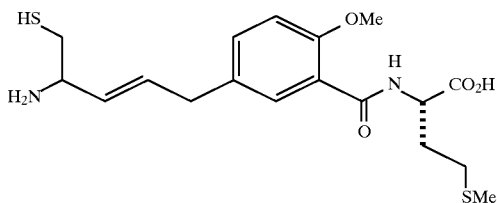

Compound PM131 was prepared in the same manner as that described in Scheme VIII, but R017M was combined with L-leucine PNB ester hydrochloride instead of L-methionine PNB ester hydrochloride, and the remaining steps were as described in Scheme VIII. The following characteristic values were obtained by nuclear magnetic resonance spectroscopy:

¹H NMR (CD₃OD) δ: 8.25 d (J=7.7 Hz), 7.31–7.41 m, 6.14 dt (J=7.0, 15.2 Hz), 5.57 dd (J=8.0, 15.4 Hz), 4.31–4.35 m, 4.15 q (J=7.1 Hz), 3.85 app q (J=5.3 Hz), 3.55 d (J=6.6 Hz), 2.86 dd (J=6.2, 14.2 Hz), 2.76 dd (J=6.4, 14.2 Hz), 1.28–1.46 m, 1.05–1.12 m, 0.79 d (J=6.6 Hz), and 0.76 d (J=6.5 Hz).

Example 164

Compound PM132

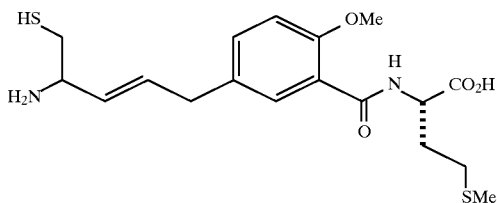

Compound PM132 was prepared in the same manner as that described in Scheme VIII, but 3-thiopheneboronic acid was used in place of benzeneboronic acid in step 3, L-methionine methyl ester hydrochloride was used in step 11 in place of L-methionine PNB ester hydrochloride, and the subsequent Na$_2$S·9H$_2$O step was omitted. Furthermore, between steps 6 and 7 in Scheme VIII, a diimide hydrogenation step was inserted (see Equation 2).

$^1$H NMR (CD$_3$OD) δ: 7.25–7.45 m, 7.19 dd (J=1.6, 4.8 Hz), 4.59 dd (J=4.4, 9.6, 1H), 2.89 dd (J=4.6, 14.7 Hz), 2.72–2.75 m, 2.71 dd (J=6.4, 14.7 Hz), 2.25–2.32 m, 2.14–2.22 m, 2.03 s, 1.97–2.06 m, and 1.69–1.87 m.

Example 165
Compound PM141

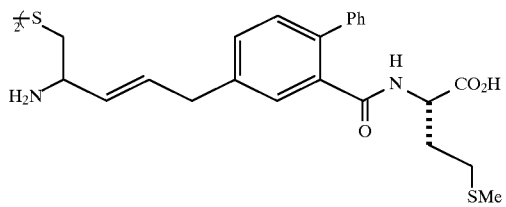

Compound PM041 hydrochloride (0.0320 g, 0.06464 mmol) was dissolved in MeOH (16 mL) and H$_2$O (6 mL), and LiOH (0.0312 g, 1.3027 mmol) was added. The resulting solution was stirred for 24 h at room temp, quenched with TFA (0.110 mL), and evaporated. The residue was purified by RP HPLC to give 0.0276 g (78%) of therapeutic compound PM141 (2 TFA salt). The following characteristic values were obtained by nuclear magnetic resonance spectroscopy:

$^1$H NMR (CD$_{3lOD}$) δ: 7.31–7.41 m, 6.09 dt (J=7.2, 14.4 Hz), 5.55 dd (J=8.3, 15.4 Hz), 4.46–4.49 m, 4.06 q (J=7.3 Hz), 3.50 d (J=6.7 Hz), 3.06 d (J=7.2 Hz), 2.07–2.15 m, 1.92–2.00 m, 1.98 s, and 1.71–1.79 m.

Example 166
Compound PM142

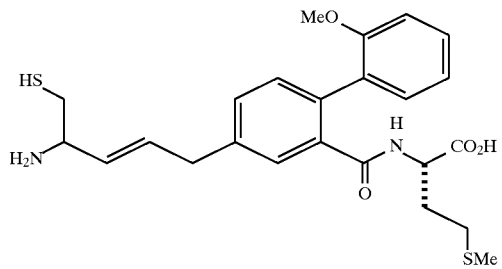

Compound PM142 was prepared in the same manner as that described in Scheme VIII, but 2-methoxybenzeneboronic acid was used in place of benzeneboronic acid in step 3, and L-methionine t-butyl ester hydrochloride was used in step 11 in place of L-methionine PNB ester hydrochloride, and the subsequent Na$_2$S·9H$_2$O step was omitted. 2-Methoxybenzene-boronic acid was obtained according to Thompson et al., *J. Org. Chem.*, 49:5237–5243 (1984), and Eggers et al., *Inorg. Chem.*, 6:160–161 (1967).

$^1$H NMR (CD$_3$OD) δ: 7.44–7.48 m, 7.32–7.39 m, 7.20–7.24 m, 6.08–7.03 m, 6.14 dt (J=7.2, 14.4 Hz), 5.58 dd (J=8.1, 15.4 Hz), 4.43–4.47 m, 3.87 q (J=6.6 Hz), 3.74 s, 3.55 d (J=6.4 Hz), 2.86 dd (J=6.1, 14.2 Hz), 2.76 dd (J=6.4, 14.0 Hz), 1.99 s, 1.98–2.16 m, 1.89–1.94 m, and 1.65–1.70 m.

Example 167

Compound PM151

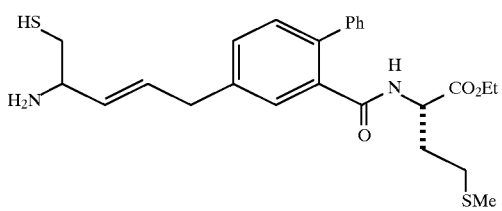

Compound PM041 was prepared in the same manner as that described in Scheme VIII, but R017M was combined with L-methionine ethyl ester hydrochloride instead of L-methionine PNB ester hydrochloride, and the subsequent Na$_2$S·9H$_2$O step was omitted. The following characteristic values were obtained by nuclear magnetic resonance spectroscopy:

$^1$H NMR (CD$_3$OD) δ: 8.39 d (J=7.7 Hz), 7.31–7.41 m, 6.13 dt (J=7.2, 15.2 Hz), 5.57 dd (J=8.0, 15.4 Hz), 4.45–4.50 m, 4.15 q, (J=7.1 Hz), 3.86 app q, (J=6.8 Hz), 3.55 d (J=6.7 Hz), 2.85 dd (J=6.3, 14.1 Hz), 2.77 dd (J=6.3, 14.1 Hz), 2.05–2.15 m, 1.88–2.00 m, 1.98 s, 1.69–1.81 m, and 1.25 t (J=7.1 Hz).

Example 168

Compound PM152

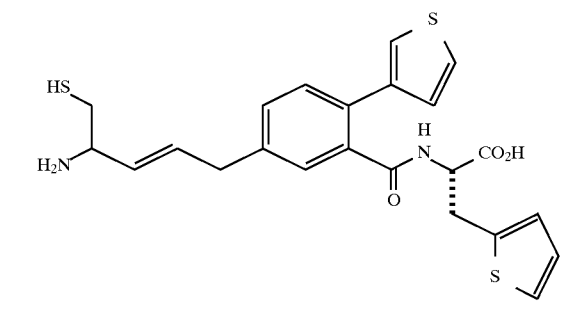

Compound PM152 was prepared in the same manner as that described in Scheme VIII, but 3-thiopheneboronic acid was used in place of benzeneboronic acid in step 3, L-3-(2-thienyl)-alanine methyl ester hydrochloride was used in step 11 in place of L-methionine PNB ester hydrochloride, and the subsequent Na$_2$S·9H$_2$O step was replaced by a LiOH/MeOH/H$_2$O hydrolysis.

$^1$H NMR (CD$_3$OD) δ: 7.25–7.46 m, 7.12 dd (J=1.8, 4.5 Hz), 6.97 dd, (J=3.5, 5.1 Hz), 6.86 d (J=2.7 Hz), 6.15 dt (J=7.2, 14.4 Hz), 5.56 dd (J=7.9, 15.4 Hz), 4.79 dd (J=4.6, 9.2 Hz), 3.89 q (J=6.8 Hz), 3.53 d (J=6.5 Hz), 3.45 dd (J=4.7, 15.0 Hz), 3.25 dd (J=9.2, 14.9 Hz), 2.88 dd (J=6.1, 14.2 Hz), and 2.79 dd (J=6.4, 14.1 Hz).

Example 169
Compound PM161

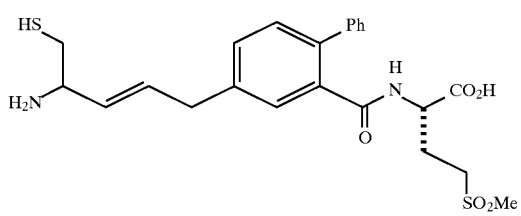

Compound PM161 was prepared in the same manner as that described in Scheme VIII, but R017M was combined with L-methioninesulfone methyl ester hydrochloride in step 11 in place of L-methionine PNB ester hydrochloride, and the subsequent $Na_2S \cdot 9H_2O$ step was replaced with a $LiOH/MeOH/H_2O$ hydrolysis. The following characteristic values were obtained by nuclear magnetic resonance spectroscopy:

$^1H$ NMR ($CD_3OD$) δ: 7.37–7.46 m, 6.16 dt (J=7.2, 14.4 Hz), 5.61 dd (J=8.1, 15.4 Hz), 4.49 br dd (J=4.5, 9.5 Hz), 3.89 q (J=6.8 Hz), 3.58 d (J=6.7 Hz), 2.90 s, 2.74–2.90 m, 2.52–2.59 m, 2.23–2.32 m, and 1.95–2.03 m.

Example 170
Compound PM162

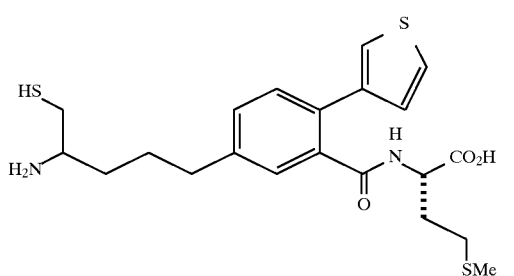

Compound PM162 was prepared in the same manner as that described in Scheme VIII, but 3-thiopheneboronic acid was used in place of benzeneboronic acid in step 3, and L-methionine t-butyl ester hydrochloride was used in step 11 in place of L-methionine PNB ester hydrochloride, and the subsequent $Na_2S \cdot 9H_2O$ step was omitted. Furthermore, between steps 6 and 7 in Scheme VIII, a diimide hydrogenation step was inserted (see Equation 2).

$^1H$ NMR ($CD_3OD$) δ: 8.47 d (J=7.7 Hz), 7.37–7.47 m, 7.23 dd (J=1.9, 4.3 Hz), 4.57–4.62 m, 2.91 dd (J=4.5, 14.7 Hz), 2.71–2.86 m, 2.28–2.35 m, 2.17–2.25 m, 2.06 s, 2.04–2.12 m, and 1.70–1.91 m.

Example 171
Compound PM172

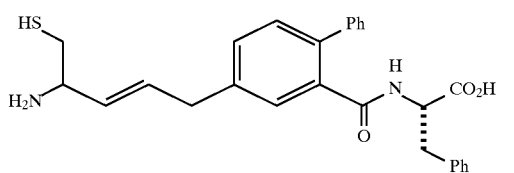

Compound PM172 was prepared in the same manner as that described in Scheme VIII, but L-phenylalanine t-butyl ester hydrochloride was used in step 11 in place of L-methionine PNB ester hydrochloride, and the subsequent $Na_2S \cdot 9H_2O$ step was omitted.

$^1H$ NMR ($CD_3OD$) δ: 8.41 d (J=7.9 Hz), 7.17–7.48 m, 6.14 dt (J=7.1, 14.2 Hz), 5.58 dd (J=8.0, 15.4 Hz), 4.72 br dd (J=5.1, 9.4 Hz), 3.88 q (J=6.8 Hz, 1H), 3.54 d (J=6.5 Hz), 3.17 dd (J=5.0, 13.9 Hz), 2.86–2.95 m, and 2.79 dd (J=6.4, 14.2 Hz).

Example 172
Compound PM182

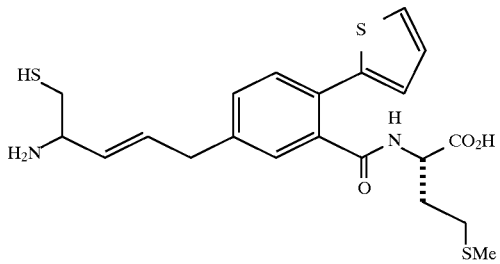

Compound PM182 was prepared in the same manner as that described in Scheme VIII, but 2-thiopheneboronic acid was used in place of benzeneboronic acid in step 3, and L-methionine t-butyl ester hydrochloride was used in step 11 in place of L-methionine PNB ester hydrochloride, and the subsequent $Na_2S \cdot 9H_2O$ step was omitted.

$^1H$ NMR ($CD_3OD$) δ: 7.30–7.50 m, 7.21 d (J=2.6 Hz), 7.08 d (J=3.6, 5.0 Hz), 6.15 dt (J=7.2, 14.3 Hz), 5.58 dd (J=8.0, 15.4 Hz), 4.61 br m, 3.89 q (J=6.9 Hz), 3.56 d (J=6.4 Hz), 2.88 dd (J=6.2, 14.2 Hz), 2.79 dd (J=6.4, 14.2 Hz), 2.29–2.36 m, 2.17–2.25 m, 2.06 s, 2.05–2.14 m, and 1.79–1.90 m.

Example 173
Compound PM192

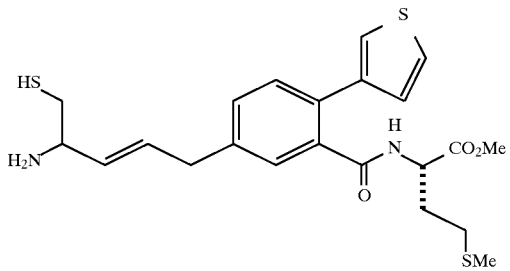

Compound PM192 was prepared in the same manner as that described in Scheme VIII, but 3-thiopheneboronic acid was used in place of benzeneboronic acid in step 3, and L-methionine methyl ester hydrochloride was used in step 11 in place of L-methionine PNB ester hydrochloride, and the subsequent $Na_2S \cdot 9H_2O$ step was omitted.

$^1H$ NMR ($CD_3OD$) δ: 7.33–7.48 m, 7.22 dd (J=2.0, 4.4 Hz) 6.16 dt (J=7.2, 15.4 Hz), 5.59 dd (J=8.1, 15.4 Hz), 4.59–4.65 m, 3.89 q (J=6.9 Hz), 3.75 s, 3.57 d, (J=6.3 Hz), 2.88 dd (J=6.7, 13.8 Hz), 2.80 dd (J=6.3, 14.1 Hz), 2.28–2.35 m, 2.18–2.25 m, 2.06 s, 2.00–2.11 m, and 1.81–1.90 m.

Example 174
Compound PM202

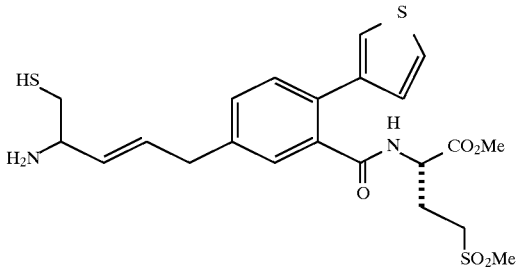

Compound PM202 was prepared in the same manner as that described in Scheme VIII, but 3-thiopheneboronic acid was used in place of benzeneboronic acid in step 3, and L-methioninesulfone methyl ester hydrochloride was used in step 11 in place of L-methionine PNB ester hydrochloride, and the subsequent $Na_2S \cdot 9H_2)O$ step was omitted.
$^1$H NMR ($CD_3OD$) δ: 7.35–7.50 m, 7.23 dd (J=1.1, 4.8 Hz), 6.15 dt (J=7.2, 14.3 Hz), 5.59 dd (J=8.0, 15.4 Hz), 4.61 br dd (J=4.7, 9.4 Hz), 3.89 br q (J=6.6, 13.6 Hz), 3.77 s, 3.56 d (J=6.5 Hz) 2.95 s, 2.76–3.01 m, 2.28–2.37 m, and 2.01–2.11 m.

Example 175
Compound PM212

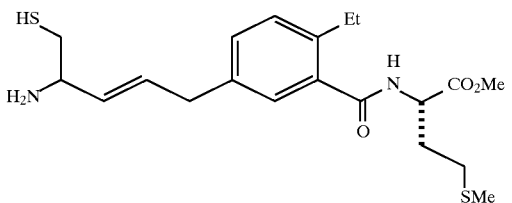

Compound PM212 was prepared in the same manner as that described in Scheme VIII, but tetravinyltin (with LiCl in DMF) was used in place of benzeneboronic acid in step 3, followed by a catalytic hydrogenation step (see Equation 1), and L-methionine methyl ester hydrochloride was used in step 11 in place of L-methionine PNB ester hydrochloride, and the subsequent $Na_2S \cdot 9H_2O$ step was omitted.
$^1$H NMR ($CD_3OD$) δ: 8.76 d (J=7.5 Hz), 7.24–7.36 m, 6.13 dt (J=7.1, 14.3 Hz), 5.54 dd (J=8.1, 15.4 Hz), 4.76 - 4.81 m, 3.87 q (J=6.8 Hz), 3.79 s, 3.50 d (J=6.3 Hz), 2.56–2.89 m, 2.18–2.26 m, 2.13 s, 2.01–2.13 m, and 1.22 t (J=7.6 Hz).

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:
1. A compound having the formula:

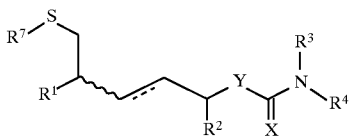

(I)

wherein $R^1$ is H, $NHR^8$, or, $NR^3R^9$ wherein $R^1$ is H, $C_{1-6}$ alkyl, $C_{1-6}$ acyl, $C_{2-14}$ alkyloxycarbonyl or any other amino-protecting group, and $R^9$ is $C_{1-6}$ alkyl, $C_{1-6}$ acyl, or $C_{2-14}$ alkyloxycarbonyl; or, when taken together with $R^7$, a bifunctional thiol-protecting group;

$R^2$ is H, $C_{1-8}$ alkyl, ($C_{6-40}$ aryl)($C_{0-6}$ alkyl), or ($C_{3-10}$ heteroaryl)($C_{0-6}$ alkyl);

$R^3$ is H, $C_{1-6}$ alkyl, or ($C_{6-40}$ aryl)($C_{0-6}$ alkyl);

$R^4$ is $C_{3-16}$ cycloalkyl, ($C_{3-16}$ heterocyclic radical)-($C_{0-6}$ alkyl), ($C_{6-12}$ aryl)($C_{0-6}$ alkyl), ($C_{3-16}$ heteroaryl)($C_{0-6}$ alkyl), $R^5(CH-)(C=O)R^6$, $R^5(CH-)(C=S)R^1$, $R^5(CH-)(CH_2)R^6$, or $R^5(CH_2-)$, wherein $R^5$ is $C_{1-6}$ alkyl, ($C_{3-10}$ heterocyclic radical)-($C_{0-6}$ alkyl), ($C_{3-10}$ heteroaryl)($C_{1-6}$ alkyl), hydroxymethyl, —$(CH_2)_n$—A—$(CH_2)_m$—$CH_3$, —$(CH_2)_n(C=O)NH_2$, or —$(CH_2)$, (C=O)NH($CH_2)_m CH_3$ (wherein A is O, S, SO, or $SO_2$, n is 0, 1, 2 or 3, and m is 0, 1, or 2), or a side chain of a naturally occurring amino acid selected from glycine, alanine, valine, leucine, isoleucine, serine, threonine, aspartic acid, asparagine, lysine, glutamic acid, glutamine, arginine, histidine, phenylalanine, cysteine, tryptophan, tyrosine, methionine, and proline; and $R^6$ is H, $NH_2$, NHOH, $C_{3-16}$ heterocyclic radical, $C_{3-16}$ heteroaryl, $NHR^{10}$, $NR^{10}R^{11}$, $OR^{12}$, $NR^{10}OR^{11}$, $NHOR^{13}$, or any other carboxyl-protecting group, wherein each of $R^{10}$ and $R^{11}$ independently, is $C_{1-6}$, alkyl. ($C_{3-16}$ heterocyclic radical)($C_{0-6}$ alkyl), or ($C_{3-16}$ heteroaryl)-($C_{0-6}$ alkyl), $R^{12}$ is H, $C_{1-6}$ alkyl, ($C_{1-12}$ acyl)oxy($C_{1-12}$ alkyl), ($C_{1-12}$ alkyl)oxy($C_{1-12}$ alkyl), or $C_{2-14}$ alkyloxy-carbonyl, and $R^{13}$ is H, $C_{1-6}$ alkyl, or ($C_{6-40}$ aryl)($C_{0-6}$ alkyl);

X is =O, =S, or two singly-bonded H;

Y is selected from the following five formulae:

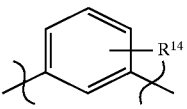

(i)

wherein $R^{14}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

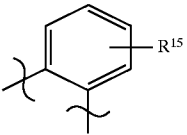

(ii)

wherein $R^1$ is H, halide, hydroxy, $C_{1-6}$ alkyl, $C_{2-6}$ alkynyl, $C_{1-12}$ alkoxy, $C_{1-6}$ acyloxy $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

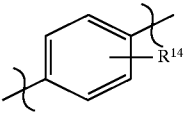

(iii)

wherein $R^6$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

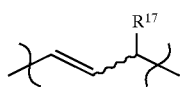

(iv)

wherein $R^{17}$ is H, $C_{1-8}$ alkyl, $(C_{6-40}$ aryl)$(C_{0-6}$ alkyl), $(C_{3-10}$ heteroaryl)$(C_{0-6}$ alkyl), or $(C_{3-10}$ heterocyclic radical)-$(C_{0-6}$ alkyl); and

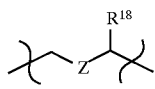

(v)

wherein $R^{18}$ is H, $C_{1-8}$ alkyl, $(C_{6-40}$ aryl)$(C_{0-6}$ alkyl),$(C_{3-10}$ heterocyclic radical)$(C_{0-6}$ alkyl), or $(C_{3-10}$ heteroaryl)$(C_{1-6}$ alkyl), and Z is O, S, SO, $SO_2$, or $NR^{19}$ wherein $R^{19}$ is H, $C_{1-6}$ alkyl, $C_{1-6}$ acyl, $(C_{6-40}$ aryl)$(C_{0-6}$ alkyl), $C_{3-10}$ heterocyclic radical, $C_{3-10}$ heteroaryl, $(C_{3-10}$ heteroaryl)$(C_{0-6}$ alkyl), or $C_{2-14}$ alkyloxycarbonyl; or wherein $R^{18}$ and $NR^{19}$ taken together form a bifunctional $C_{6-40}$ aryl, a bifunctional $C_{3-12}$ heterocyclic radical, or a bifunctional $C_{3-12}$ heteroaryl; and $R^7$ is H, a thiol-protecting group, or a moiety set forth in the above generic formula (1) wherein $R^7$ is deleted, said compound being a symmetrical disulfide dimer or an asymmetrical disulfide or, when taken together with $R^1$, a bifunctional thiol-protecting group;

or a pharmaceutically acceptable salt thereof.

2. A compound of claim 1, having the formula:

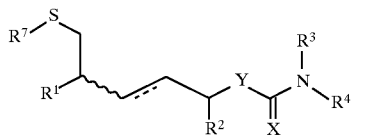

(II)

wherein $R^1$ is H, $NHR^8$, or $NR^8R^9$, wherein $R^8$ is H, $C_{1-6}$ alkyl, $C_{1-6}$ acyl, $C_{2-14}$ alkyloxycarbonyl or any other amino-protecting group, and $R^9$ is $C_{1-6}$ alkyl, $C_{1-6}$ acyl, $C_{2-14}$ alkyloxycarbonyl or, when taken together with $R^7$, a bifunctional thiol-protecting group; and $R^7$ is H; a thiol protecting group or, when taken together with $R^1$ a bifunctional thiol-protecting group; or a moiety set forth in the above generic formula (II) wherein $R^7$ is deleted, said compound being a symmetrical disulfide dimer or an asymmetrical disulfide;

or a pharmaceutically acceptable salt thereof.

3. A compound of claim 2, having the following formula:

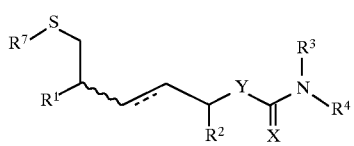

(III)

wherein $R^1$ is NHR8 or $NR^8R^9$, wherein $R^8$ is $C_{1-6}$ alkyl, $C_{1-6}$ acyl, $C_{2-14}$ alkyloxycarbonyl, or any other amino-protecting group, and $R^9$ is $C_{1-6}$ alkyl, $C_{1-6}$ acyl, $C_{2-14}$ alkyloxycarbonyl or, when taken together with $R^7$, a bifunctional thiol-protecting group;

$R^6$ is H, $NH_2$, NHOH, $C_{3-10}$ heterocyclic radical, $C_{3-10}$ heteroaryl, $NHR^{10}$, $NR^{10}R^{11}$, $OR^{12}$, $NR^{10}OR^{11}$, $NHOR^{13}$, or any other carboxyl-protecting group (wherein each of $R^{10}$ and $R^{11}$, independently, is $C_{1-6}$ alkyl, $(C_{3-16}$ heterocyclic radical)-$(C_{0-6}$ alkyl), $C_{2-14}$ alkyloxycarbonyl, or (C3-16 heteroaryl)-$(C_{1-6}$ alkyl)), $R^{12}$ is $C_{1-6}$ alkyl, $(C_{1-12}$ acyl)oxy$(C_{1-12}$ alkyl), $(C_{1-12}$ alkyl)oxy$(C_{1-12}$ alkyl), or $C_{2-14}$ alkyloxycarbonyl, and $R^{13}$ is H, $C_{1-6}$ alkyl, or $(C_{6-40}$ aryl) $(C_{0-6}$ alkyl);

$R^7$ is a thiol-protecting group, or, when taken together with $R^9$, a bifunctional thiol-protecting group; or a moiety set forth in the above generic formula (III) wherein $R^7$ is deleted, said compound being a symmetrical disulfide dimer or an asymmetrical disulfide.

4. A compound having the following formula:

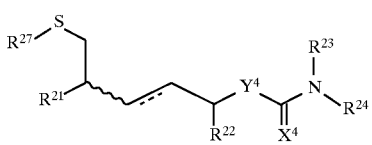

(IV)

wherein $R^{21}$ is H, $NH_2$, $NHR^{28}$, or $NR^{28}R^{29}$, wherein each $R^{28}$ and $R^{29}$, independently, is $C_{1-6}$ alkyl, $C_{1-6}$ acyl, or $C_{2-14}$ alkyloxycarbonyl;

$R^{22}$ is H, $C_{1-8}$ alkyl, $(C_{6-40}$ aryl)$(C_{0-6}$ alkyl), or $(C_{3-10}$ heteroaryl)$(C_{0-6}$ alkyl);

$R^{23}$ is H, $C_{1-8}$ alkyl, or $(C_{6-40}$ aryl)$(C_{0-6}$ alkyl);

$R^{24}$ is $C_{3-16}$ cycloalkyl, $(C_{6-12}$ aryl)$(C_{0-6}$ alkyl), $(C_{3-16}$ heterocyclic radical)-$(C_{1-6}$ alkyl), $(C_{3-10}$ heteroaryl)$(C_{0-6}$ alkyl), $R^{25}$(CH—)(C=O)$R^{26}$, $R^{25}$(CH—)(C=S)$R^{26}$, $R^{25}$(CH—)(CH$_2$)$R^{26}$, or $R^{25}$(CH$_2$—), wherein $R^{25}$ is $C_{1-6}$ alkyl, $(C_{6-12}$ aryl)$(C_{0-6}$ alkyl), $(C_{3-10}$ heterocyclic radical)$(C_{0-6}$ alkyl), $(C_{3-10}$ heteroaryl)$(C_{0-6}$ alkyl), hydroxymethyl, —(CH$_2$)$_n$—A$^4$—(CH$_2$)$_m$—CH$_3$, —(CH$_2$)$_n$(C=O)NH$_2$, or —(CH$_2$)$_n$(C=O)NH—(CH$_2$)$_m$ CH$_3$ (wherein A$^4$ is O, S, SO, or SO$_2$, n is 0, 1, 2 or 3, and m is 0, 1, or 2), or a side chain of a naturally occurring amino acid selected from glycine, alanine, valine, leucine, isoleucine, serine, threonine, aspartic acid, asparagine, lysine, glutamic acid, glutamine, arginine, histidine, phenylalanine, cysteine, tryptophan, tyrosine, methionine, and proline; and $R^{26}$ is H, $NH_2$, NHOH, $C_{6-12}$ aryl, $C_{3-16}$ heterocyclic radical, $C_{3-16}$, heteroaryl, $NHR^{30}$, $NR^{30}R^{31}$, $OR^{32}$, $NR^{30}OR^{31}$, or $NHOR^{33}$, wherein each of $R^{30}$ and $R^{31}$, independently, is $C_{1-6}$ alkyl, $(C_{6-12}$ aryl)$(C_{0-6}$ alkyl), $(C_{3-16}$ heterocyclic radical)$(C_{0-6}$ alkyl), or $(C_{3-16}$ heteroaryl)$(C_{0-6}$ alkyl), $R^{32}$ is H, $C_{1-6}$ alkyl, $(C_{1-12}$ acyl)oxy$(C_{1-12}$ alkyl), $(C_{1-12}$ alkyl)oxy$(C_{1-12}$ alkyl), or $C_{2-14}$ alkyloxycarbonyl, and $R^{33}$ is H, $C_{1-6}$ alkyl, or $(C_{6-40}$ aryl)$(C_{0-6}$ alkyl);

$X^4$ is =O, =S, or two singly-bonded H;

$Y^4$ is selected from the following five formulae:

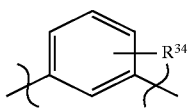

(vi)

wherein $R^{34}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

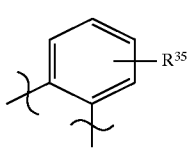

(vii)

wherein $R^{35}$ is H, halide hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

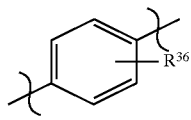
(viii)

wherein $R^{36}$ is H, halide, hydroxy, $C_{1-6}$ alkyl, $C_{2-6}$ alkenyl, $C_{2-6}$ alkynyl, $C_{1-12}$ alkoxy, $C_{1-6}$ acyloxy, $C_{1-6}$ acyl, $C_{6-41}$ aryl, $C_{3-40}$ heterocyclic radical, $C_{3-40}$ heteroaryl, $C_{1-12}$ alkylsulfonyloxy, $C_{1-12}$ haloalkylsulfonyloxy, $C_{6-40}$ arylsulfonyloxy, or $C_{6-41}$ aryloxy;

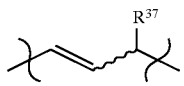
(ix)

wherein $R^{37}$ is H, $C_{1-8}$ alkyl, $(C_{6-40}$ aryl$)(C_{0-6}$ alkyl$)$, or $(C_{3-10}$ heteroaryl$)(C_{0-6}$ alkyl$)$, $(C_{3-10}$ heterocyclic radical$)(C_{0-6}$ alkyl$)$; and

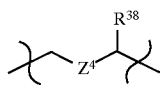
(x)

wherein $R^{38}$ is H, $C_{1-8}$ alkyl, $(C_{6-40}$ aryl$)(C_{0-6}$ alkyl$)$, $(C_{3-10}$ heterocyclic radical$)(C_{0-6}$ alkyl$)$, or $(C_{3-10}$ heteroaryl$)(C_{0-6}$ alkyl$)$; and $Z^4$ is O, S, SO, $SO_2$, or $NR^{39}$ wherein $R^{39}$ is H, $C_{1-6}$ alkyl, $C_{1-6}$ acyl, $(C_{6-40}$ aryl$)(C_{0-6}$ alkyl$)$, $(C_{3-12}$ heterocyclic radical$)(C_{0-6}$ alkyl$)$, $(C_{3-10}$ heteroaryl$)(C_{0-6}$ alkyl$)$, or $C_{2-14}$ alkyloxycarbonyl; or wherein $R^{38}$ and $NR^{39}$ taken together form a bifunctional $C_{6-40}$ aryl, a bifunctional $C_{3-12}$ heterocyclic radical, or a bifunctional $C_{3-12}$ heteroaryl; and $R^{27}$ is H; a thiol protecting group; or a moiety set forth in the above generic formula (IV) wherein $R^{27}$ is deleted, said compound being a symmetrical disulfide dimer or an asymmetrical disulfide;

or a pharmaceutically acceptable salt thereof.

5. A compound of claim 4, having the following formula:

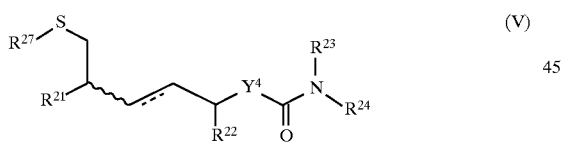
(V)

wherein $R^{21}$ is H, $NH_2$, or $NHR^{28}$, $R^{28}$ being $C_{1-6}$ alkyl, $C_{1-6}$ acyl, or $C_{2-14}$ alkyloxycarbonyl;

$R^{23}$ is H or methyl;

$R^{24}$ is $R^{25}(CH-)(C=O)R^{26}$, $R^{25}(CH-)(C=S)R^{26}$, or $R^{25}(CH_2-)$; and $Y^4$ is selected from the following three formulae:

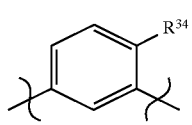
(xi)

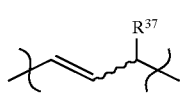
(xii)

and

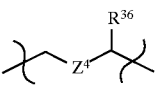
(xiii)

wherein $Z^4$ is O, S, or $NR^{39}$, wherein $R^{39}$ is H, $C_{1-6}$ alkyl, or $C_{1-6}$ acyl; or wherein $R^{38}$ and $NR^{39}$ taken together form a bifunctional $C_{6-40}$ aryl, a bifunctional $C_{3-12}$ heterocyclic radical, or a bifunctional $C_{3-12}$ heteroaryl.

6. A compound of claim 4, having the following formula:

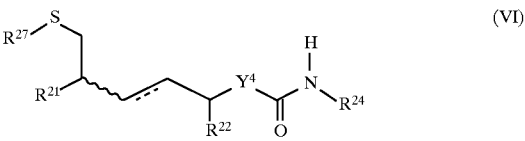
(VI)

wherein $R^{21}$ is $NH_2$ or $NHR^{28}$, $R^{28}$ being $C_{1-6}$ alkyl, $C_{1-6}$ acyl, or $C_{2-14}$ alkyloxycarbonyl;

$R^{22}$ is H or $C_{1-8}$ alkyl;

$R^{24}$ is $C_{3-16}$ heterocyclic radical, $C_{3-16}$ heteroaryl, $R^{25}(CH-)(C=O)R^{26}$, or $R^{25}(CH-)(C=S)R^{26}$, wherein $R^{25}$ is $C_{1-6}$ alkyl, hydroxymethyl, $-(CH_2)_n-A^4-(CH_2)_m-CH_3$, $-(CH_2)_n(C=O)NH_2$, or $-(CH_2)_n(C=O)NH(CH_2)_mCH_3$ (wherein $A^4$ is O, S, SO, or $SO_2$, n is 0, 1, or 2, and m is 0 or 1), or a side chain of a naturally occurring amino acid selected from glycine, alanine, valine, leucine, isoleucine, serine, threonine, aspartic acid, asparagine, lysine, glutamic acid, glutamine, arginine, histidine, phenylalanine, cysteine, tryptophan tyrosine, methionine, and proline, and $R^{32}$ is H, $C_{1-6}$ alkyl, or $(C_{1-12}$ acyl$)$oxy$(C_{1-12}$ alkyl$)$; and $Y^4$ is selected from the following three formulae:

(xiv)

(xv)

and

(xvi)

wherein $Z^4$ is O, S, or $NR^{39}$, wherein $R^{39}$ is H, $C_{1-6}$ alkyl, or $C_{1-6}$ acyl; or wherein $R^{38}$ and $NR^{39}$ taken together form a bifunctional $C_{6-40}$ aryl, a bifunctional $C_{3-12}$ heterocyclic radical, or a bifunctional $C_{3-12}$ heteroaryl.

7. A compound of claim 4, wherein $R^{21}$ is $NH_2$; $R^{22}$ is H or $C_{1-6}$ alkyl; and $R^{23}$ is H.

8. A compound of claim 7, wherein $R^{24}$ is $R^{25}(CH)(C=O)R^{26}$.

9. A compound of claim 8, wherein $R^{25}$ is a side chain of glutamine, serine leucine, methionine, or phenylalanine.

10. A compound of claim 8, wherein $R^{26}$ is $OR^{32}$.

11. A compound of claim 10, wherein $R^{32}$ is H or $C_{1-6}$ alkyl.

12. A compound of claim 7, wherein $R^{27}$ is H and $X^4$ is =O.

13. A compound of claim 7, wherein $Y^4$ is formula (vi), and $R^{34}$ is $C_{1-6}$ alkyl, $C_{2-6}$ alkenyl, or $C_{1-6}$ alkoxy.

14. A compound of claim 13, wherein $R^{34}$ is $C_{1-6}$ alkyl.

15. A compound of claim 4, wherein $R^{21}$ is $NH_2$; $R^{28}$ is $C_{1-6}$ alkyl $R^{22}$ is H or $C_{1-6}$ alkyl; $R^{23}$ is H; $R^{24}$ is $R^{25}$(CH)(C=O)$R^{26}$; $R^{25}$ is a side chain of glutamine, serine, leucine, methionine, or phenylalanine; $R^{26}$ is $OR^{32}$ and $R^{32}$ is H or $C_{1-6}$ alkyl; $R^{27}$ is H; $X^4$ is =O; and $Y^4$ is formula (vi), and $R^{34}$ is $C_{1-6}$ alkyl, $C_{2-6}$ alkenyl, or $C_{1-6}$ alkoxy.

16. A compound of claim 15, wherein $R^{25}$ is a side chain of methionine.

17. A compound of claim 16, wherein $R^{22}$ is H and $R^{34}$ is $C_{1-6}$ alkyl.

18. A compound of claim 15, wherein the carbon atoms on either side of the dashed line are $sp^3$ carbon atoms.

19. A compound of claim 16, wherein the carbon atoms on either side of the dashed line are $sp^2$ carbon atoms, the double bond having trans geometry.

\* \* \* \* \*